United States Patent [19]
Linsley et al.

[11] Patent Number: 5,885,796
[45] Date of Patent: Mar. 23, 1999

[54] CTLA4 RECEPTOR AND USES THEREOF

[75] Inventors: Peter S. Linsley; Jeffrey A. Ledbetter, both of Seattle, Wash.; Nitin K. Damle, Hopewell, N.J.; William Brady, Bothell, Wash.

[73] Assignee: Bristol-Myers Squibb Company, Princeton, N.J.

[21] Appl. No.: 465,078

[22] Filed: Jun. 5, 1995

Related U.S. Application Data

[60] Division of Ser. No. 375,390, Jan. 18, 1995, which is a continuation-in-part of Ser. No. 228,208, Apr. 15, 1994, which is a continuation-in-part of Ser. No. 8,898, Jan. 22, 1993, which is a continuation-in-part of Ser. No. 723,617, Jun. 27, 1991, abandoned.

[51] Int. Cl.$^6$ .......................... C12N 21/02; C12N 15/00; C07H 21/00; C07K 1/00

[52] U.S. Cl. .................. 435/69.1; 435/172.1; 435/320.1; 435/325; 530/350; 536/23.1; 536/23.4; 536/23.5

[58] Field of Search ..................... 530/350, 325, 530/387.3, 388.22; 435/6, 69.1, 172.1, 172.3, 240.1, 240.2, 320.1; 536/23.1, 23.4, 23.5

[56] References Cited

U.S. PATENT DOCUMENTS

| | | | |
|---|---|---|---|
| 4,399,216 | 8/1983 | Axel | 435/6 |
| 4,683,195 | 7/1987 | Mullis et al. | 435/6 |
| 4,683,202 | 7/1987 | Mullis | 435/91.2 |
| 5,116,964 | 5/1992 | Capon et al. | 536/23.5 |
| 5,225,538 | 7/1993 | Capon et al. | 530/387.3 |

FOREIGN PATENT DOCUMENTS

WO 95/33770  12/1995  WIPO.

OTHER PUBLICATIONS

Linsley, et al., "CTLA–4 is a Second Receptor for the B–cell Activation Antigen B7," *J. Exp. Med.* 174:561–569 (1991).

SIGMA, Biochemical Organic Compounds Catalogue: 1114–1115 (1990).

Janeway, "Approaching the Asymptote? Evolution and Revolution in Immunology", *Cold Spring Harbor Symp. Quant. Biol.* LIV:1–13 (1989).

Shaw and Shimuzu, "Two Molecular Pathways of Human T Cell Adhesion; Establishment of Receptor–Ligand Relationship", *Current Opinion in Immunology*, Eds. Kindt and Long, 1:92–97 (1988).

Hemler, "Adhesive Protein Receptors on Hematopoietic Cells", *Immunology Today* 9:109–113 (1988).

Kakiuchi et al., "B Cells as Antigen–Presenting Cells: The Requirement for B Cell Activation", *J. Immunol.* 131:109–114 (1983).

Krieger et al., "Antigen Presentation by Splenic B Cells: Resting B Cells are Ineffective, Whereas Activated B Cells are Effective Accessory Cells for T Cell Responses", *J. Immunol.* 135:2937–2945 (1985).

McKenzie, "Alloantigen Presentation by B Cells—Requirement for IL–1 and IL–6", *J. Immunol.* 141:2907–2911 (1988).

Hawrylowicz and Unanue, "Regulation of Antigen–Presentation–I IFN–γInduces Antigen–Presenting Properties on B Cells", *J. Immunol.* 141:4083–4088 (1988).

Springer et al., "The Lymphocyte Function–Associated LFA–1, CD2,and LFA–3 Molecules: Cell Adhesion Receptors of the Immune System", *A. Rev. Immunol.* 5:223–252 (1987).

Dinarello and Mier, "Current Concepts—Lymphokines", *New Engl. Jour. Med.* 317:940–945 (1987).

Weiss et al., "The Role of the T3/Antigen Receptor Complex in T–Cell Activation", *Ann. Rev. Immunol.* 4:593–619 (1986).

McMichael, Ed., "Non–Lineage, LFA–1 Family, and Leucocyte Common Antigens: New and Previously Defined Clusters", *Leukocyte Typing III*, Oxford Univ. Press, Oxford, UK (1987).

Moingeon et al., "CD2–mediated Adhesion Facilitates T Lymphocyte Antigen Recognition Function", *Nature* 339:312–314 (1988).

Makgoba et al., ICAM–1 A Ligand for LFA–1–Dependent Adhesion of B, T and Myeloid Cells, *Nature* 331:86–88 (1988).

Staunton et al., "Functional Cloning of ICAM–2, A Cell Adhesion Ligand for LFA–1 Homologous to ICAM–1", *Nature* 339:61–64 (1989).

Norment et al., "Cell–Cell Adhesion Mediated by CD8 and MHC Class I Molecules", *Nature* 336:79–81 (1988).

Doyle and Strominger, "Interactions Between CD4 and Class II MHC Molecules Mediates Cell Adhesion", *Nature* 330:256–259 (1987).

Stoolman, "Adhesion Molecules Controlling Lymphocyte Migration", *Cell* 56:907–910 (1989).

Brescher and Cohn, "A Theory of Self–Nonself Discrimination", *Science* 169:1042–1049 (1970).

Freeman et al., "B7, A New Member of the Ig Superfamily with Unique Expression on Activated and Neoplastic B Cells", *J. Immunol.* 143 (8) :2714–2722 (1989).

Freedman et al., "B7, A B Cell–Restricted Antigen that Identifies Preactivated B Cells", *J. Immunol.* 138:3260–3267 (1987).

Clark et al., "Polypeptides on Human B Lymphocytes Associated with Cell Activation", *Human Immunol.* 16:100–113 (1986).

(List continued on next page.)

*Primary Examiner*—Nancy Degen
*Assistant Examiner*—Sean McGarry
*Attorney, Agent, or Firm*—Joseph M. Sorrentino

[57] ABSTRACT

The invention identifies the CTLA4 receptor as a ligand for the B7 antigen. The complete amino acid sequence encoding human CTLA4 receptor gene is provided. Methods are provided for expressing CTLA4 as an immunoglobulin fusion protein, for preparing hybrid CTLA4 fusion proteins, and for using the soluble fusion proteins, fragments and derivatives thereof, including monoclonal antibodies reactive with B7 and CTLA4, to regulate T cell interactions and immune responses mediated by such interactions.

12 Claims, 37 Drawing Sheets4

OTHER PUBLICATIONS

Yokochi et al., "B Lymphoblast Antigen (BB–1) Expressed on Epstein–Barr Virus–Activated B Cells Blasts, B Lymphoblastoid Cell Lines, and Burkitt's Lymphomas", *J. Immunol.* 128:823–827 (1981).

Weiss, "Structure and Function of the T Cell Antigen Receptor", *J. Clin. Invest.* 86:1015–1022 (1990).

Allen, "Antigen Processing at the Molecular Level", *Immunol. Today* 8:270–273 (1987).

Schwartz, "A Cell Culture Model for T Lymphocyte Clonal Anergy", *Science* 248:1349–1356 (1990).

Weaver and Unanue, "The Costimulatory Function of Antigen–Presenting Cells", *Immunol. Today* 11:49–55 (1990).

Aruffo and Seed, "Molecular Cloning of a CD28 cDNA by a High–Efficiency COS Cell Expression System", *Proc. Natl. Acad. Sci.* 84:8573–8577 (1987).

Damle et al., "Alloantigen–Specific Cytotoxic and Suppressor T Lymphocytes are Derived from Phenotypically Distinct Precursors", *J. Immunol.* 131:2296–2300 (1983).

June et al. "T–Cell Proliferation Involving the CD28 Pathway is Associated with Cyclosporine–Resistant Interleukin 2 Gene Expression", *Mol. Cell. Biol.* 7:4472–4481 (1987).

Thompson et al., "CD28 Activation Pathway Regulates the Production of Multiple T–Cell–Derived Lymphokines/Cytokines", *Proc. Natl. Acad. Sci.* 86:1333–1337 (1989).

Lindsten et al., "Regulation of Lymphokine Messenger RNA Stability by a Surface–Mediated T Cell Activation Pathway", *Science* 244:339–343 (1989).

Damle et al., "Monoclonal Antibody Analysis of Human T Lymphocyte Subpopulations Exhibiting Autologous Mixed Lymphocyte Reaction", *Proc. Natl. Acad. Sci.* 78:5096–5098 (1981).

Lesslauer et al., "T90/44 (9.3 Antigen). A Cell Surface Molecule with a Function in Human T Cell Activation", *Eur. J. Immunol.* 16:1289–1296 (1986).

Linsley et al., "T–Cell Antigen CD28 Mediates Adhesion with B Cells by Interacting with Activation Antigen B7–BB–1", *Proc. Natl. Acad. Sci. USA* 87:5031–5035 (1990).

Linsley et al., "Binding of the B Cell Activation Antigen B7 to CD28 Costimulates T Cell Proliferation and Interleukin 2 mRNA Accumulation", *J. Exp. Med.* 173:721–730 (1991).

Kohno et al., CD28 Molecule as a Receptor–Like Function for Accessory Signals in Cell–Mediated Augmentation of IL–2 Production, *Cell. Immunol.* 131:1–10 (1990).

Brunet et al., "A New Member of the Immunoglobulin Superfamily—CTLA–4", *Nature* 328–267–270 (1987).

Brunet et al., "A Differential Molecular Biology Search for Genes Preferentially Expressed in Functional T Lymphocytes: The CTLA Genes", *Immunol. Rev.* 103:21–36 (1988).

Dariavach et al., "Human Ig Superfamily CTLA–4 Gene: Chromosomal Localization and Identity of Protein Sequence Between Murine and Human CTLA–4 Cytoplasmic Domains", *Eur. J. Immunol.* 18:1901–1905 (1988).

Lafage–Pochitaloff et al., "Human CD28 and CTLA–4 Ig Superfamily Genes are Located on Chromosome 2 at Bands q33–q34", *Immunogenetics* 31:198–201 (1990).

Capon et al., "Designing CD4 Immunoadhesins for AIDS Therapy", *Nature* 337:525–531 (1989).

Malik et al., "Molecular Cloning, Sequence Analysis, and Functional Expression of a Novel Growth Regulator, Oncostatin M", *Molec. and Cell. Biol.* 9:2847–2853 (1989).

Storb, "Marrow Transplantation for Severe Aplastic Anemia: Methotrexate Alone Compared with a Combination of Methotrexate and Cyclosporine for Preventation of Acute Graft–Versus–Host Disease", *Blood* 56:119–125 (1986).

Storb and Thomas, "Graft–Versus Host Disease in Dog and Man: The Seattle Experience", *Immunol. Rev.* 88:215–238 (1985).

Aruffo et al., "CD44 is the Principal Cell Surface Receptor for Hyaluronate", *Cell* 61:1303–1313 (1990).

Seed and Aruffo, "Molecular Cloning of the CD2 antigen, the T–cell Erythrocyte Receptor, by a Rapid Immunoselection Procedure", *Proc. Natl. Acad. Sci.* 84:3365–3369 (1987).

Aruffo and Seed, "Molecular Cloning of Two CD7 (T–Cell Leukemia Antigen) cDNAs by a COS Cell Expression System", *EMBO Hour.* 6:3313–3316 (1987).

Ledbetter et al., "Crosslinking of Surface Antigens Causes Mobilization of Intracellular Ionized Calcium in T Lymphocytes", *Proc. Natl. Acad. Sci.* 84:1384–1388 (1987).

Ledbetter et al., "CD28 Ligation in T–Cell Activation: Evidence for Two Signal Transduction Pathways", *Blood* 75:1531–1539 (1990).

Damle et al., "Immunoregulatory T Lymphocytes in Man", *J. Immunol.* 139:1501–1508 (1987).

Wysocki and Sato,"'Panning' for Lymphocytes: A Method for Cell Selection", *Proc. Natl. Acad. Sci.* 75:2844–2848 (1978).

Damle et al., "Differential Regulatory Signals Delivered by Antibody Binding to the DC28 (Tp44) Molecule During the Activation of Human T Lymphocytes", *J. Immunol.* 140:1753–1761 (1988).

Schneck et al., "Inhibition of an Allospecific T Cell Hybridoma by Soluble Class I Proteins and Peptides: Estimation of the Affinity of a T Cell Receptor for MHC", *Cell* 54:47–55 (1989).

Recny et al., "Structural and Functional Characterization of the CD2 Immunoadhesion Domain", *J. Biol. Chem.* 265:8542–8549 (1990).

Clayton et al., "Identification of Human CD4 Residues Affecting Class II MHC Versis HIV–1 gp120 Binding", *Nature* 339:548–551 (1989).

Alzari et al. "Three–Dimensional Structure of Antibodies", *Ann. Rev. Immuno.* 6:555–580 (1988).

Hautanen et al., "Effects of Modifications of the RGD Sequence and Its Context on Recognition by the Fibronectin Receptor", *J. Biol. Chem.* 264:1437–1442 (1989).

DiMinno et al., Exposure of Platelet Fibrinogen–Binding Sites by Collagen, Arachidonic Acid, and ADP: Inhibition by a Monoclonal Antibody to the Glycoprotein IIb–IIIa Complex, *Blood* 61:140–148 (1983).

Thiagarajan and Kelley, "Exposure of Binding Sites for Vitronectin on Platelets Following Stimulation", *J. Biol. Chem.* 263:3035–3038 (1988).

June et al., "Role of the CD28 Receptor in T–Cell Activation", *Immunology Today* 11:211–2316 (1989).

Hathcock et al., "Identification of an Alternative CTLA–4 Ligand Costimulatory for T Cell Activation", *Science* 262:905–907 (1993).

Nelson et al., "Medullary Thymic Epithelium Expresses a Ligand for CTLA4 in Situ and in Vitro", *Journal of Immunology* 151:2453–2461 (1993).

Lin, et al., "Long–Term Acceptance of Major Histocompatability Complex Mismatched Cardiac Allografts Induced by CTLA4Ig Plus Donor–specific Transfusion", *J. Exp. Med.* 178:1801–1806 (1993).

Lenschow, et al., "Long–Term Survival of Xenographic Pancreatic Islet Grafts Induced by CTLA4Ig", *Science* 257:789–792 (1992).

Zhou, et al., "T Cells of Staphylococcal Enterotoxin B–Tolerized Autoimmune MRL–1pr/1pr Mice Require Co–Stimulation Through the B7–CD28/CTLA–4 Pathway for Activation and Can Be Reanergized in Vivo by Stimulation of the T Cell Receptor in the Absence of this Co–Stimulatory Signal", *European Journal of Immunology* 24:1019–1025 (1994).

Nishikawa, et al., "Effect of CTLA–4 Chimeric Protein on Rat Autoimmune Anti–glomerular Basement Membrane Glomerulonephritis", *European Journal of Immunology* 24:1249–1254 (1994).

Blazar, et al., "In Vivo Blockade of CD28/CTLA4: Br/BB1 Interaction With CTLA4–Ig Reduces Lethal Murine Graft–Versus–Host Disease Across the Major Histocompatibility Complex Barrier in Mice", *Blood* 83:3815–3825 (1994).

Milich, et al., "Soluble CTLA–4 Can Suppress Autoantibody Production and Elicit Long Term Unresponsiveness in a Novel Transgenic Model", *The Journal of Immunology* 153:429–435 (1994).

Pearson, et al., "Transplantation Tolerance Induced by CTLA4–Ig", *Transplantation* 57:1701–1706 (1994).

Verwilghen, et al., "Expression of Functional B7 and CTLA4 on Rheumatoid Synovial T Cells", *The Journal of Immunology* 153:1378–1385 (1994).

Finck, et al., "Treatment of Murine Lupus with CTLA4IG", *Science* 265:1225–1227 (1994).

FIG. 3

```
ONCOSTATIN M SIGNAL PEPTIDE
-25                   -20
 M   G   V   L   L   T   Q   R   T   L   L   S   L   V   L
ATG GGT GTA CTG CTC ACA CAG AGG ACG CTG CTC AGT CTG GTC CTT   45

-10                              -1 +1
 A   L   L   F   P   S   M   A   S   M   A   M   H   V   A
GCA CTC CTG TTT CCA AGC ATG GCG AGC ATG GCA ATG CAC GTG GCC   90

+10                              +20
 Q   P   A   V   V   L   A   S   S   R   G   I   A   S   F
CAG CCT GCT GTG GTA CTG GCC AGC AGC CGA GGC ATC GCC AGC TTT   135

+30
 V   C   E   Y   A   S   P   G   K   A   T   E   V   R   V
GTG TGT GAG TAT GCA TCT CCA GGC AAA GCC ACT GAG GTC CGG GTG   180

+40                              +50
 T   V   L   R   Q   A   D   S   Q   V   T   E   V   C   A
ACA GTG CTT CGG CAG GCT GAC AGC CAG GTG ACT GAA GTC TGT GCG   225

+60
 A   T   Y   M   M   G   N   E   L   T   F   L   D   D   S
GCA ACC TAC ATG ATG GGG AAT GAG TTG ACC TTC CTA GAT GAT TCC   270

+70                              +80
 I   C   T   G   T   S   S   G   N   Q   V   N   L   T   I
ATC TGC ACG GGC ACC TCC AGT GGA AAT CAA GTG AAC CTC ACT ATC   315

+90
 Q   G   L   R   A   M   D   T   G   L   Y   I   C   K   V
CAA GGA CTG AGG GCC ATG GAC ACG GGA CTC TAC ATC TGC AAG GTG   360

GLYCOSYLATION SITE
            +100                         +110
 E   L   M   Y   P   P   P   Y   Y   L   G   I   G   N   G
GAG CTC ATG TAC CCA CCG CCA TAC TAC CTG GGC ATA GGC AAC GGA   405

+120
 T   Q   I   Y   V   I   D   P   E   P   C   P   D   S   D
ACC CAG ATT TAT GTA ATT GAT CCA GAA CCG TGC CCA GAT TCT GAC   450

+130
 F   L   L   W   I   L   A   A   V   S   S   G   L   F   F
TTC CTC CTC TGG ATC CTT GCA GCA GTT AGT TCG GGG TTG TTT TTT   495

+140                              +150
 Y   S   F   L   L   T   A   V   S   L   S   K   M   L   K
TAT AGC TTT CTC CTC ACA GCT GTT TCT TTG AGC AAA ATG CTA AAG   540

+160
 K   R   S   P   L   T   T   G   V   Y   V   K   M   P   P
AAA AGA AGC CCT CTT ACA ACA GGG GTC TAT GTG AAA ATG CCC CCA   585

+170                              +180
 T   E   P   E   C   E   K   Q   F   Q   P   Y   F   I   P
ACA GAG CCA GAA TGT GAA AAG CAA TTT CAG CCT TAT TTT ATT CCC   630

+187
 I   N
ATC AAT                                                        636
```

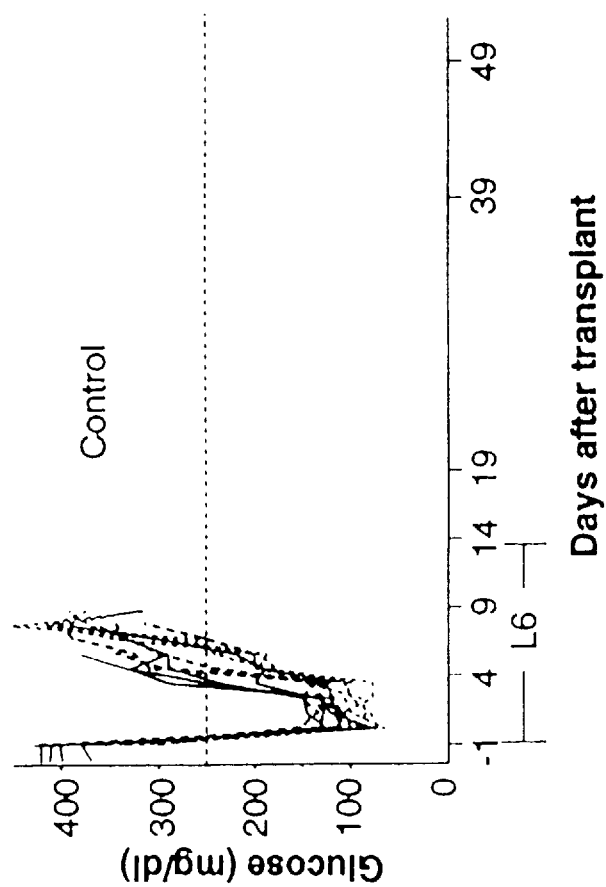

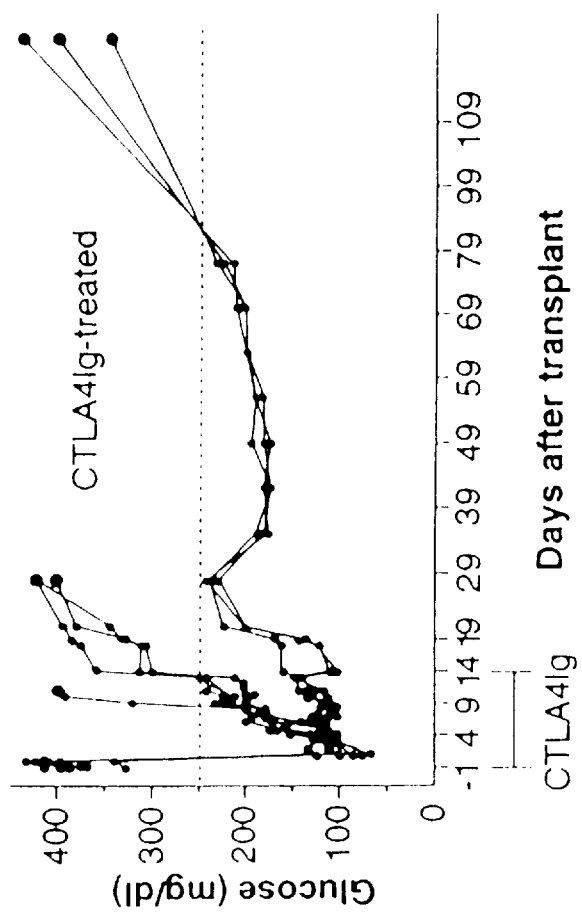

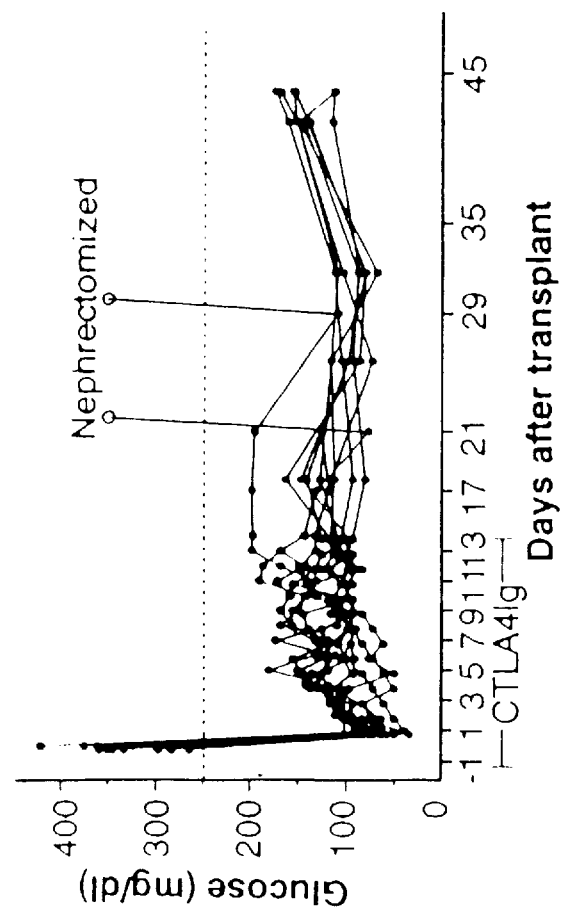

CD5 LEADER

ATGCCCATGGGGTCTCTGCAACCGTCGGCCACCTTGTACCTGCTCCCCATCCTCCTCGCTTCCTGCCTCGGACTAGT

CAGCAATGCACGTGCCCAGCCTGCTGTGTACTGGCCAGCAGCGGA

CTLA4

GGCATCAGCTTTGTGTGTGAGTATGCATCTCCAGGCAAAGCCACT

GAGGTCCGGGTGACAGTGCTTCGGCAGGCTGACAGCCAGGTGACT

GAAGTCTGTGCGGCAACCTACATGATGGGGAATGAGTTGACCTTC

CTAGATGATTCCATCTGCACGGGCACCTCCAGTGGAAATCAAGTG

AACCTCACTATCCAAGGACTGAGGGCCATGGACACGGGACTCTAC

ATCTGCAAGGTGGAGCTCATGTACCCACCGCCATACTACCTGGGC

ATAGGCAACGGAGCCCAGATTTATGTAATTGATCCAGAACCGTGC

CCAGTATCT

GGATCCAGAGTGACTGAGCAAGAAAGCAAACCTGTGCAGATGATGTACCAGATTGGTTTATTTA

GAGTGGCATCAATGGCTTCTGAGAAATGAAGATCCTGGAGCTTCCATTTGCCAGTGGGA

CAATGAGCATGTGTTGCTGTTGCCTGATGAAGCTCAGCCCTGAGCAGTTGAGAGTA

TAATCAACTTTGAAAAAACTGACTGAAGTGCCAGTTCTAATGTTTATGGAAGAGAGAAGA

TCAAAGTGTACTTACCTCGACGTGTTTAGCTCTTCAGCCAATCTGTCTGGCATCTCCTCAG

TGGCTATGGGCATTACTGACGTGTTTAGCTCTTCAGCCAATCTGTCTGGCATCTCCTCAG

CAGAGAGCCTGAAGATATCTCAAGCTGTCCATGCAGCACATGCAGAAATCAATGAAGCAG

GCAGAGAGGTGGTAGGGTCAGCAGAGGCTGGAGTGATGCTGCAAGCGTCTCTGAAGAAT

OVALBUMIN

TTAGGGCTGACCATCCATTCCTTCTGTATCAAGCACATCGCAACCAACGCCGTTCTCT

TCTTTGGCAGATGTGTTTGATAGAAGGTT

FIG. 27

CD5 LEADER

ATGCCCATGGGGTCTCTGCAACCGCTGGCCACCTTG

TACCTGCTCCCCATCCTCCTGCTTCCTGCCTCGGACTAGT

CAGCAATGCACGTGGCCCAGCCTGCTGTGGTACTGGCCAGCAGCCGA

GGCATCAGCTTTGTGTGTGAGTATGCATCTCCAGGCAAAGCCACT

CTLA

GAGGTCCGGGTGACAGTGCTTCGGCAGCTGACAGCCAGGTGACT

GAAGTCTGTGCGGCAACCTACATGATGGGGAATGAGTTGACCTTC

CTAGATGATTCCATCTGCACGGCACCTCCAGTGGAAATCAAGTG

AACCTCACTATCCAAGGACTGAGGGCCATGACGGGACTCTAC

ATCTGCAAGGTGGAGCTCATGTACCCACCGCCATACTACCTGGGG

ATAGGCAACGGAGCCCAGATTTATGTAATTGATCCAGAACCGTGC

CCAGTATCT

ENV GP120

GGATCCCTGTTGAATGGCAGTCTAGCAGAAGAGAGGTAGTAATTAGATCTGCCA

ATTCACAGACAATGCTAAAACCATAATAGTACAGCTGAACCAATCTGTAGAAATTAATT

GTACAAGACCCAACAACAATACAAGAAAAAGTATCCGTATCCAGAGGGGACCAGGAGAG

CATTTGTTACAATAGGAAAAATATGGAAATATGAGACAAGCACATTGTAACATTAGTAGAG

CAAAATGGAATGCCACTTTAAACAGATAGCTAGCAAATTAAGAGAACAATTTGGAAATA

ATAAAACAATAATCTTTAAGCAATCCTGAGGAAAGCTT

FACS CTLA4-OVA    FIG. 28
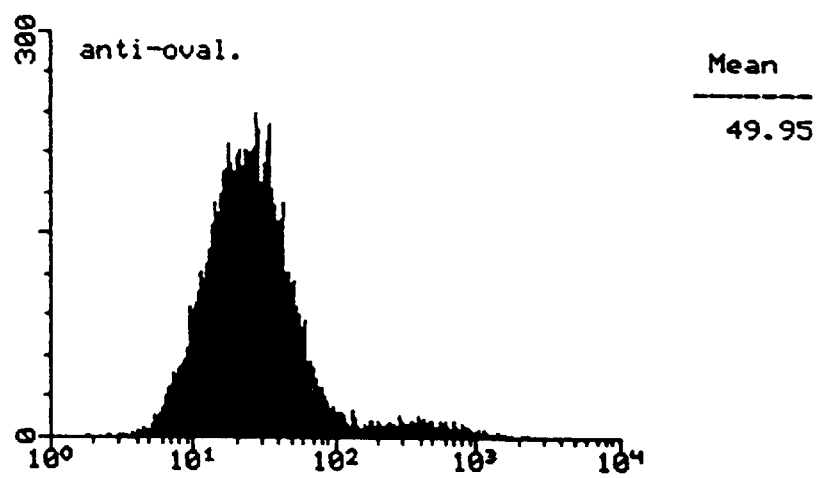
anti-oval.
Mean
49.95
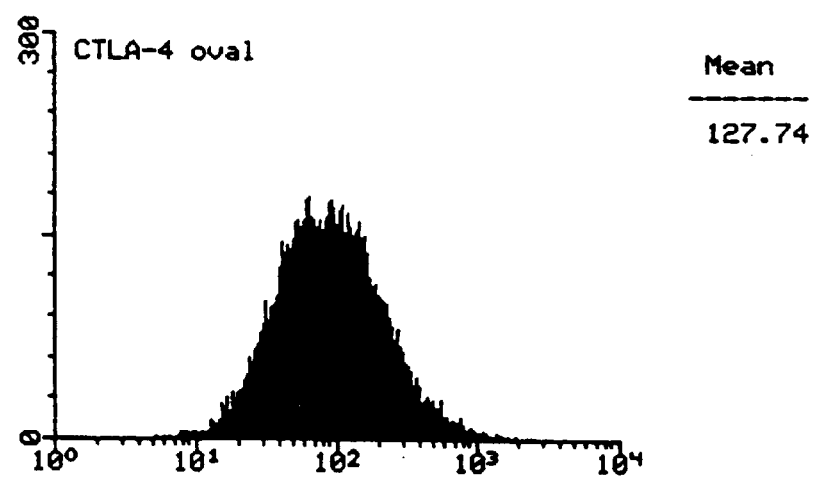
CTLA-4 oval
Mean
127.74
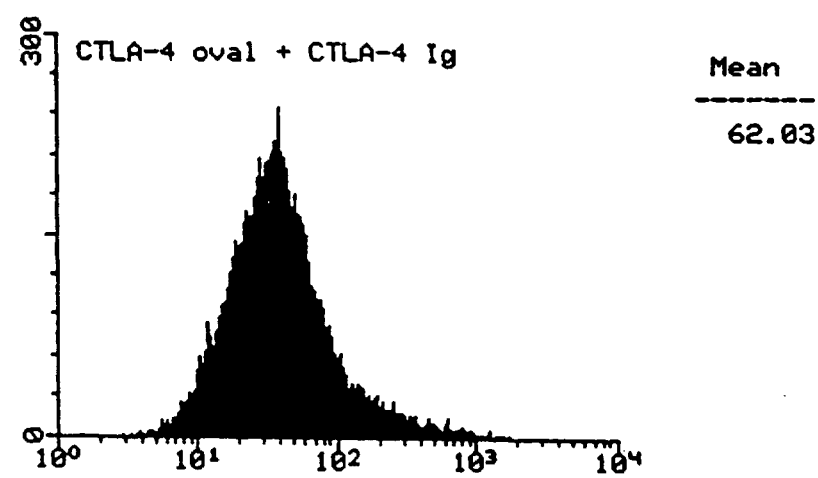
CTLA-4 oval + CTLA-4 Ig
Mean
62.03

FIG. 29    FACS CTLA4-E7
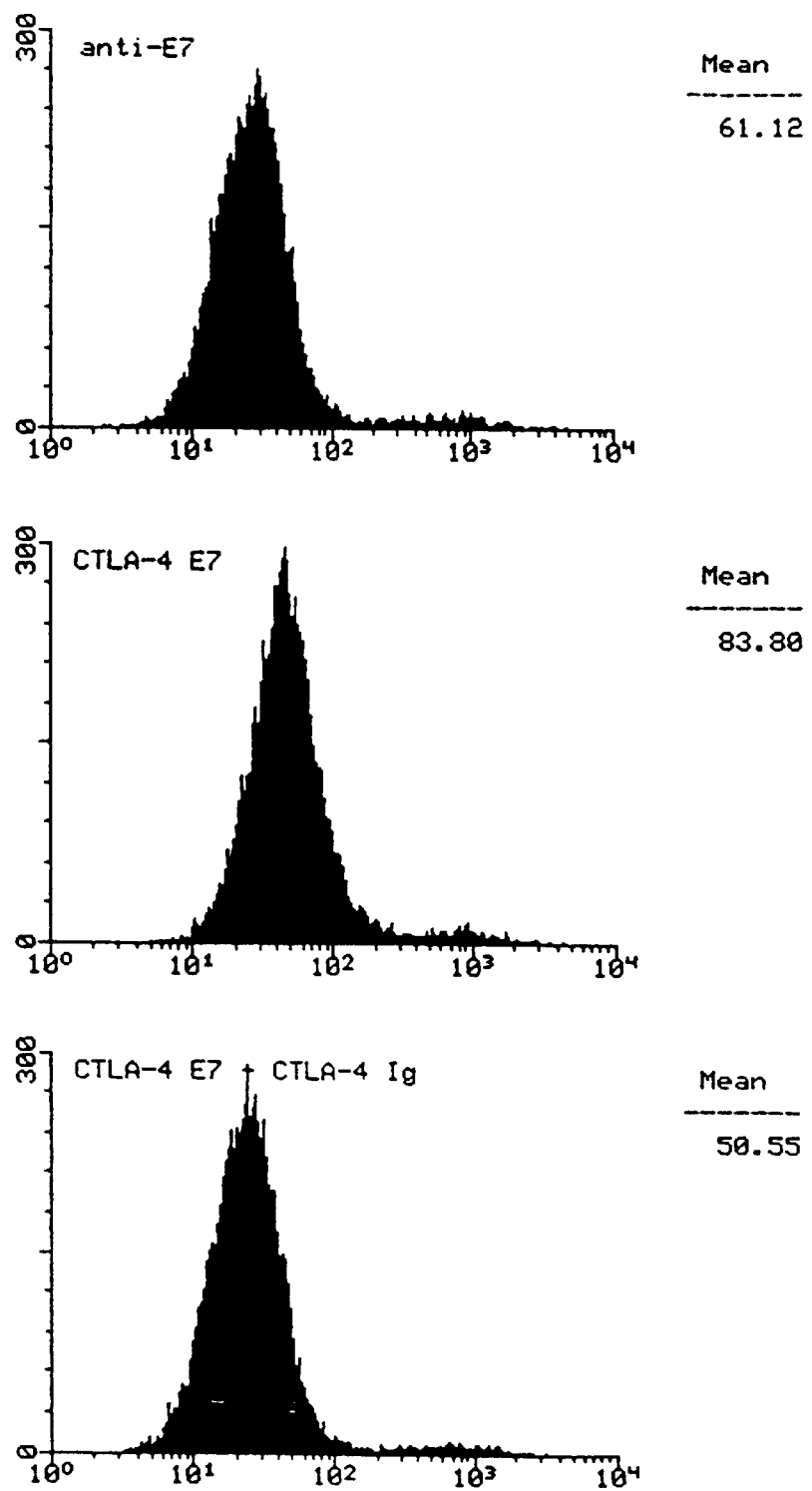

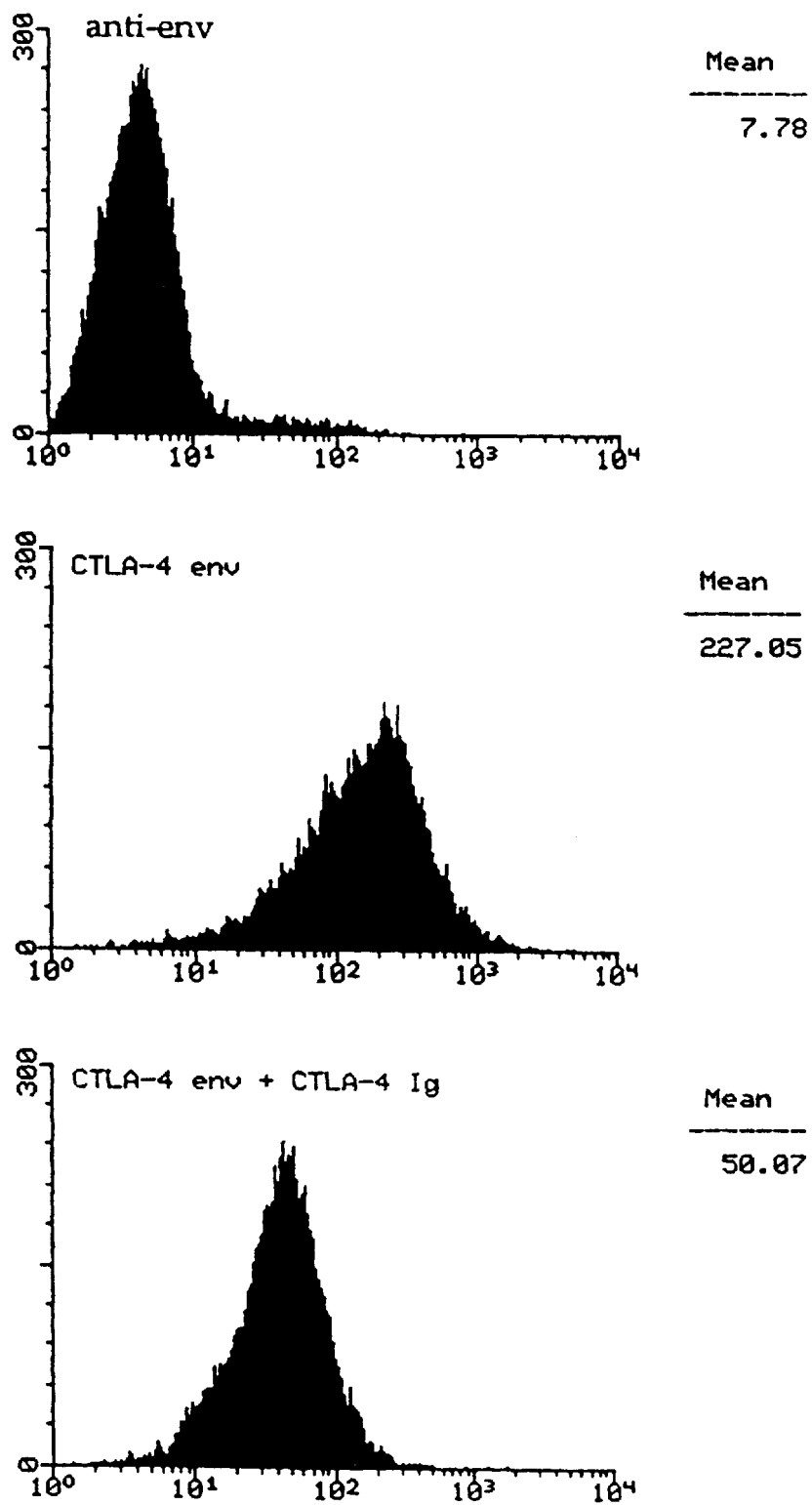
FACS CTLA4-ENV  FIG. 30

FACS CTLA4-p97      FIG. 31
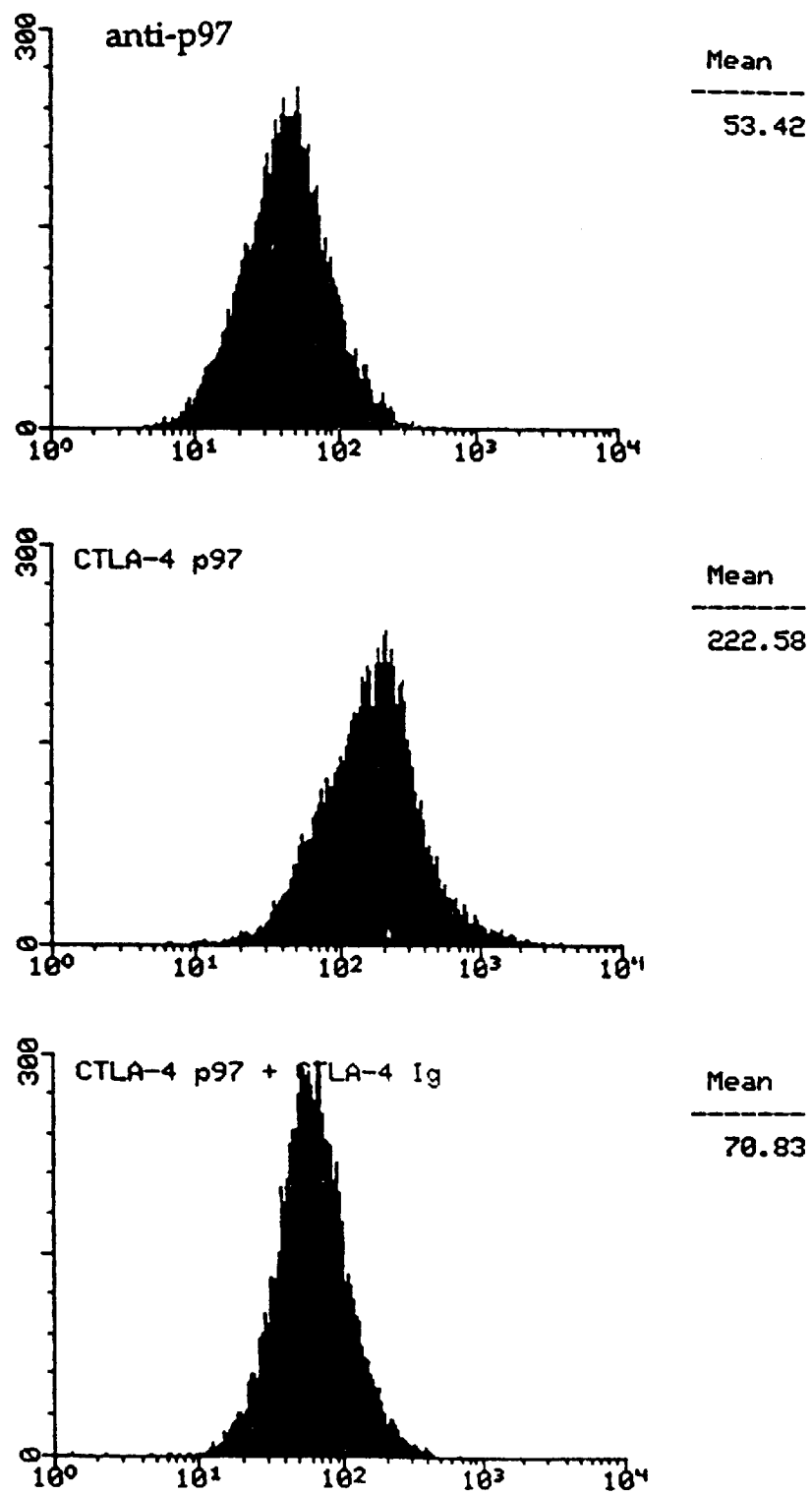

BI-FUNCTIONAL ELISA OF CTLA4-EVN GP 120 FUSION PROTEIN

```
                   ├─────── leader ─→        ├─ CTLA-4 EC ─→
  1      QASPMGVLLT QRTLLSLVLA LLFPSMASMA MHVAQPAVVL ASSRGIASFV

51      CEYASPGKAT EVRVTVLRQA DSQVTEVCAA TYMMGNELTF LDDSICTGTS

101      SGNQVNLTIQ LRAMDTGLYI CKVELMYPPP YYLGIGNGTQ IYVIDPEPCP
                  ├─ P97 ─→
151      DSRDPGMEVR WCATSDPEQH KCGNMSEAFR EAGIQPSLLC VRGTSADHCV

201      QLIAAQEADA ITLDGGAIYE AGKEHGLKPV VGEVYDQEVG TSYYAVAVVR

251      RSSHVTIDTL KGVKSCHTGI NRTVGWNVPV GYLVESGRLS VMGCDVLKAV

301      SDYFGGSCVP GAGETSYSES LCRLCRGDSS GEGVCDKSPL ERYYDYSGAF

351      RCLAEGAGDV AFVKHSTVLE NTDGKTLPSW GQALLSQDFE LLCRDGSRAD

401      VTEWRQCHLA RVPAHAVVVR ADTDGGLIFR LLNEGQRLFS HEGSSFQMFS

451      SEAYGQKDLL FKDSTSELVP IATQTYEAWL GHEYLHAMKG LLCDPNRLPP

```
            |————leader—→      |—CTLA-4 EC—›
  1   QASPMGVLLT QRTLLSLVLA LLFPSMASMA MHVAQPAVVL ASSRGIASFV

51   CEYASPGKAT EVRVTVLRQA DSQVTEVCAA TYMMGNELTF LDDSICTGTS

101   SGNQVNLTIQ LRAMDTGLYI CKVELMYPPP YYLGIGNGTQ IYVIDPEPCP
                 |—E7—›
151   DSRDPMHGDT PTLHEYMLDL QPETTDLYCY EQLNDSSEEE DEIDGPAGQA

201   EPDRAHYNIV TFCCKCDSTL RLCVQSTHVD IRTLEDLLMG TLGIVCPICS

251   QKP*SR
```

CTLA4 RECEPTOR AND USES THEREOF

This application is a divisional of U.S. Ser. No. 08/375,390, filed Jan. 18, 1995, which is a continuation-in-part of U.S. Ser. No. 08/228,208, filed Apr. 15, 1994, which is a continuation-in-part of U.S. Ser. No. 08/008,898, filed Jan. 22, 1993, which is a continuation-in-part of U.S. Ser. No. 723,617 filed Jun. 27, 1991, now abandoned, the contents of all of which are incorporated by reference into the present application.

Throughout this application various publications are referenced. The disclosures of these publications in their entireties are hereby incorporated by reference into this application in order to more fully describe the state of the art to which this invention pertains.

The present invention relates to expression of CTLA4 hybrid fusion proteins, the CTLA4 receptor gene, identification of the interaction between the CTLA4 receptor and cells expressing B7 antigen, and to methods for regulating cellular interactions involving the CTLA4 receptor and the B7 antigen.

BACKGROUND OF THE INVENTION

The hallmark of a vertebrate immune system is the ability to discriminate "self" from "non-self" (foreign). This property has led to the evolution of a system requiring multiple signals to achieve optimal immune activation (Janeway, *Cold Spring Harbor Symp. Quant. Biol.* 54:1–14 (1989)). T cell-B cell interactions are essential to the immune response. Levels of many cohesive molecules found on T cells and B cells increase during an immune response (Springer et al., *A. Rev. Immunol.* 5:223–252 (1987); Shaw and Shimuzu, *Current Opinion in Immunology*, Eds. Kindt and Long, 1:92–97 (1988)); and Hemler *Immunology Today* 9:109–113 (1988)). Increased levels of these molecules may help explain why activated B cells are more effective at stimulating antigen-specific T cell proliferation than are resting B cells (Kaiuchi et al., *J. Immunol.* 131:109–114 (1983); Kreiger et al., *J. Immunol.* 135:2937–2945 (1985); McKenzie, *J. Immunol.* 141:2907–2911 (1988); and Hawrylowicz and Unanue, *J. Immunol.* 141:4083–4088 (1988)).

The generation of a T lymphocyte ("T cell") immune response is a complex process involving cell-cell interactions (Springer et al., *A. Rev. Immunol.* 5:223–252 (1987)), particularly between T and accessory cells such as B cells, and production of soluble immune mediators (cytokines or lymphokines) (Dinarello and Mier, *New Engl. Jour. Med* 317:940–945 (1987)). This response is regulated by several T-cell surface receptors, including the T-cell receptor complex (Weiss et al., *Ann. Rev. Immunol.* 4:593–619 (1986)) and other "accessory" surface molecules (Springer et al., (1987) supra). Many of these accessory molecules are naturally occurring cell surface differentiation (CD) antigens defined by the reactivity of monoclonal antibodies on the surface of cells (McMichael, Ed., *Leukocyte Typing III*, Oxford Univ. Press, Oxford, N.Y. (1987)).

Antigen-independent intercellular interactions involving lymphocyte accessory molecules are essential for an immune response (Springer et al., (1987), supra). For example, binding of the T cell-associated protein, CD2, to its ligand LFA-3, a widely expressed glycoprotein (reviewed in Shaw and Shimuzu, supra), is important for optimizing antigen-specific T cell activation (Moingeon et al., *Nature* 339:314 (1988)).

An important adhesion system involves binding of the LFA-1 glycoprotein found on lymphocytes, macrophages, and granulocytes (Springer et al., (1987), supra; Shaw and Shimuzu (1988), supra) to its ligands ICAM-1 (Makgoba et al., *Nature* 331:86–88 (1988)) and ICAM-2 (Staunton et al., *Nature* 339:61–64 (1989)). The T cell accessory molecules CD8 and CD4 strengthen T cell adhesion by interaction with MHC class I (Norment et al., *Nature* 336:79–81 (1988)) and class II (Doyle and Strominger, *Nature* 330:256–259 (1987)) molecules, respectively. "Homing receptors" are important for control of lymphocyte migration (Stoolman, *Cell* 56:907–910 (1989)).

The VLA glycoproteins are integrins which appear to mediate lymphocyte functions requiring adhesion to extracellular matrix components (Hemler, supra). The CD2/LFA-3, LFA-1/ICAM-1 and ICAM-2, and VLA adhesion systems are distributed on a wide variety of cell types (Springer et al., (1987), supra; Shaw and Shimuzu, (1988,) supra and Hemler, (1988), supra).

Numerous in vitro studies have demonstrated that cytokines are involved in the generation of alloreactive effector cells. For example, membrane bound IL-4 and soluble IL-4 receptor were administered separately to mice and were shown to augment the lymphoproliferative response (William C. Fanslow et al. "Regulation of Alloreactivity in vivo by IL-4 and the soluble Il-4 receptor" J. Immunol. 147:535–540 (1991)). Specifically, administration of IL-4 to BALB\c mice resulted in slight augmentation of the lymphoproliferative response. In contrast, the soluble IL-4 receptor suppressed this response to allogeneic cells in a dose dependent manner. Moreover, a neutralizing antibody against IL-4 and another against soluble IL-4 receptor were effective inhibitors of the lymphoproliferative response.

It was proposed many years ago that B lymphocyte activation requires two signals (Bretscher and Cohn, *Science* 169:1042–1049 (1970)) and now it is believed that all lymphocytes require two signals for their optimal activation, an antigen specific or clonal signal, as well as a second, antigen non-specific signal (Janeway, supra). Freeman et al. (*J. Immunol.* 143(8):2714–2722 (1989)) isolated and sequenced a cDNA clone encoding a B cell activation antigen recognized by mAb B7 (Freeman et al., *J. Immunol.* 138:3260 (1987)). COS cells transfected with this cDNA have been shown to stain by both labeled mAb B7 and mAb BB-1 (Clark et al., *Human Immunol.* 16:100–113 (1986); Yokochi et al., *J. Immunol.* 128:823 (1981)); Freeman et al., (1989) supra; and Freedman et al., (1987), supra)). In addition, expression of this antigen has been detected on cells of other lineages, such as monocytes (Freeman et al., supra).

The signals required for a T helper cell ($T_h$) antigenic response are provided by antigen-presenting cells (APC). The first signal is initiated by interaction of the T cell receptor complex (Weiss, *J. Clin. Invest.* 86:1015 (1990)) with antigen presented in the context of class II major histocompatibility complex (MHC) molecules on the APC (Allen, *Immunol. Today* 8:270 (1987)). This antigen-specific signal is not sufficient to generate a full response, and in the absence of a second signal may actually lead to clonal inactivation or anergy (Schwartz, *Science* 248:1349 (1990)). The requirement for a second "costimulatory" signal provided by the MHC has been demonstrated in a number of experimental systems (Schwartz, supra; Weaver and Unanue, *Immunol. Today* 11:49 (1990)). The molecular nature of this second signal(s) is not completely understood, although it is clear in some cases that both soluble molecules such as interleukin (IL)-1 (Weaver and Unanue, supra) and membrane receptors involved in intercellular adhesion (Springer, *Nature* 346:425 (1990)) can provide costimulatory signals.

CD28 antigen, a homodimeric glycoprotein of the immunoglobulin superfamily (Aruffo and Seed, *Proc. Natl. Acad. Sci.* 84:8573–8577 (1987)), is an accessory molecule found on most mature human T cells (Damle et al., *J. Immunol.* 131:2296–2300 (1983)). Current evidence suggests that this molecule functions in an alternative T cell activation pathway distinct from that initiated by the T-cell receptor complex (June et al., *Mol. Cell. Biol.* 7:4472–4481 (1987)). Monoclonal antibodies (mabs) reactive with CD28 antigen can augment T cell responses initiated by various polyclonal stimuli (reviewed by June et al., supra). These stimulatory effects may result from mAb-induced cytokine production (Thompson et al., *Proc. Natl. Acad. Sci* 86:1333–1337 (1989); and Lindsten et al., *Science* 244:339–343 (1989)) as a consequence of increased mRNA stabilization (Lindsten et al., (1989), supra). Anti-CD28 mAbs can also have inhibitory effects, i.e., they can block autologous mixed lymphocyte reactions (Damle et al., *Proc. Natl. Acad. Sci.* 78:5096–6001 (1981)) and activation of antigen-specific T cell clones (Lesslauer et al., *Eur. J. Immunol.* 16:1289–1296 (1986)).

Studies have shown that CD28 is a counter-receptor for the B cell activation antigen, B7/BB-1 (Linsley et al, *Proc. Natl. Acad. Sci. USA* 87:5031–5035 (1990)). For convenience the B7/BB-1 antigen is hereafter referred to as the "B7 antigen". The B7 ligands are also members of the immunoglobulin superfamily but have, in contrast to CD28 and CTLA4, two Ig domains in their extracellular region, an N-terminal variable (V)-like domain followed by a constant (C)-like domain.

An important non-specific costimulatory signal is delivered to the T cell when there are at least two homologous B7 family members found on APC's, B7-1 (also called B7 or CD80) and B7-2 (also called CD86), both of which can deliver costimulatory signals to T cells via either CD28 or CTLA4. Costimulation through CD28 or CTLA4 is essential for T cell activation since a soluble Ig fusion protein of CTLA4 (CTLA4Ig) has successfully been used to block T cell activation events in vitro and in vivo. Failure to deliver this second signal may lead to clonal inactivation or T cell anergy.

Interactions between CD28 and B7 antigen have been characterized using genetic fusions of the extracellular portions of B7 antigen and CD28 receptor, and Immunoglobulin (Ig) Cγ1 (constant region heavy chains) (Linsley et al, *J. Exp. Med.* 173:721–730 (1991)). Immobilized B7Ig fusion protein, as well as B7 positive CHO cells, have been shown to costimulate T cell proliferation.

T cell stimulation with B7 positive CHO cells also specifically stimulates increased levels of transcripts for IL-2. Additional studies have shown that anti-CD28 mAb inhibited IL-2 production induced in certain T cell leukemia cell lines by cellular interactions with a B cell leukemia line (Kohno et al., *Cell. Immunol.* 131-1-10 (1990)).

CD28 has a single extracellular variable region (V)-like domain (Aruffo and Seed, supra). A homologous molecule, CTLA4 has been identified by differential screening of a murine cytolytic-T cell cDNA library (Brunet et al., *Nature* 328:267–270 (1987)).

Transcripts of the CTLA4 molecule have been found in T cell populations having cytotoxic activity, suggesting that CTLA4 might function in the cytolytic response (Brunet et al., supra; and Brunet et al., *Immunol. Rev.* 103–21–36 (1988)). Researchers have reported the cloning and mapping of a gene for the human counterpart of CTLA4 (Dariavach et al., *Eur. J. Immunol.* 18:1901–1905 (1988)) to the same chromosomal region (2q33–34) as CD28 (Lafage-Pochitaloff et al., *Immunogenetics* 31:198–201 (1990)). An Ig fusion of CTLA4 binds to B7-1 with ≈20 fold higher avidity than a corresponding Ig fusion of CD28.

Sequence comparison between this human CTLA4 DNA and that encoding CD28 proteins reveals significant homology of sequence, with the greatest degree of homology in the juxtamembrane and cytoplasmic regions (Brunet et al., 1988, supra; Dariavach et al., 1988, supra).

The high degree of homology between CD28 and CTLA4, together with the co-localization of their genes, raises questions as to whether these molecules are also functionally related. However, since the protein product of CTLA4 has not yet been successfully expressed, these questions remain unanswered.

Expression of soluble derivatives of cell-surface glycoproteins in the immunoglobulin gene superfamily has been achieved for CD4, the receptor for HIV-1, and CD28 and B7 receptors, using hybrid fusion molecules consisting of DNA sequences encoding amino acids corresponding to portions of the extracellular domain of CD4 receptor fused to antibody domains (immunoglobulin γ1 (Capon et al., *Nature* 337:525–531 (1989) (CD4) and Linsley et al., *J. Exp. Med.*, supra (CD28 and B7)).

There is a need for molecules which can identify in vitro B7 positive B cells, i.e., activated B cells, for leukocyte typing and FAC sorting. Further, there is a need for molecules which may be used to prevent the rejection of organ transplants and inhibit the symptoms associated with lupus erythematosus and other autoimmune diseases. In the past, major therapies relied on panimmunosuppressive drugs, such as cyclosporine A or monoclonal antibodies (MAbs) to CD3 to prevent organ transplants or inhibit symptoms of lupus. Unfortunately, these drugs must frequently be taken for the life of the individual, depress the entire immune system, and often produce secondary health ailments such as increased frequency of infections and cancer.

SUMMARY OF THE INVENTION

Accordingly, the present invention provides the complete and correct DNA sequence encoding the amino acid sequence corresponding to the human CTLA4 receptor protein, and identifies B7 antigen (e.g. B7-1 and B7-2 antigens) and CD11a/18 (LFA1) as natural ligands for the CTLA4 receptor.

The invention also provides a method for expressing the DNA as a CTLA4 immunoglobulin (Ig) fusion protein product. Embodiments of the invention include CTLA4Ig fusion protein, and hybrid (chimeric) fusion proteins including CD28/CTLA4Ig fusion proteins (which is also referred to herein as the CTLA4/CD28Ig fusion protein). Also provided are methods for using the CTLA4 fusion protein, B7Ig fusion protein, hybrid fusion proteins, and fragments and/or derivatives thereof, such as monoclonal antibodies reactive with CTLA4 and the B7 antigen, to regulate cellular interactions and immune responses.

The human CTLA receptor protein of the invention is encoded by 187 amino acids and includes a newly identified N-linked glycosylation site.

The CTLA4Ig fusion protein of the invention binds the B7 antigen expressed on activated B cells, and cells of other lineages, a ligand for CD28 receptor on T cells. The CTLA4Ig binds B7 antigen with significantly higher affinity than B7 binding to the CD28 receptor. The CTLA4Ig construct has a first amino acid sequence corresponding to the extracellular domain of the CTLA4 receptor fused to a second amino acid sequence corresponding to the human Ig Cγ1 domain. The first amino acid sequence contains amino acid residues from about position 1 to about position 125 of the amino acid sequence corresponding to the extracellular domain of CTLA4 joined to a second amino acid sequence containing amino acid residues corresponding to the hinge, CH2 and CH3 regions of human IgCγ1. The fusion protein is preferably produced in dimeric form. Soluble CTLA4Ig is a potent inhibitor in vitro of T and B lymphocyte responses.

Also contemplated in the invention are soluble CTLA4 and hybrid fusion proteins thereof, e.g., soluble hybrid fusion proteins, such as CD28/CTLA4Ig fusion proteins. The extracellular domain of CTLA4 is an example of a soluble CTLA4 molecule. Alternatively, a molecule having the extracellular domain of CTLA4 joined to a polypeptide tag is another example of a soluble CTLA4 molecule. Other soluble CTLA4 molecules include those having the extracellular domain of CTLA4 fused or joined with a portion of a biologically or chemically active protein such as the papillomavirus E7 gene product (CTLA4-E7), melanoma-associated antigen p97 (CTLA4-p97), and HIV env protein (CTLA4-env gp120).

As an example of a soluble hybrid fusion protein, the present invention provides CD28/CTLA4Ig fusion proteins having a first amino acid sequence corresponding to fragments of the extracellular domain of CD28 joined to a second amino acid sequence corresponding to fragments of the extracellular domain of CTLA4Ig and a third amino acid sequence corresponding to the hinge, CH2 and CH3 regions of human IgCγ1. One embodiment of the hybrid fusion proteins is a CD28/CTLA4Ig fusion construct having a first amino acid sequence containing amino acid residues from about position 1 to about position 94 of the amino acid sequence corresponding to the extracellular domain of CD28, joined to a second amino acid sequence containing amino acid residues from about position 94 to about position 125 of the amino acid sequence corresponding to the extracellular domain of CTLA4, joined to a third amino acid sequence containing amino acids residues corresponding to the hinge, CH2 and CH3 regions of human IgCγ1. Other embodiments of the hybrid fusion proteins of the invention are described in Tables I and II and Example 6.

Also included in the invention is a method for regulating T cell interactions with other cells by inhibiting the interaction of CTLA4-positive T cells with B7 positive cells by reacting the T cells with ligands for the CTLA4 receptor. The ligands include B7Ig fusion protein, a monoclonal antibody reactive with CTLA4 receptor, and antibody fragments.

The invention also provides a method for regulating T cell interactions with B7 positive cells, using a ligand for the B7 antigen. Such a ligand is soluble CTLA4 fusion protein, e.g., CTLA4Ig fusion protein, of the invention, its fragments or derivatives, soluble CD28/CTLA4 hybrid fusion protein, e.g., the CD28/CTLA4Ig hybrid fusion protein, or a monoclonal antibody reactive with the B7 antigen.

The invention further includes a method for treating immune system diseases mediated by T cell interactions with B7 positive cells by administering a ligand reactive with B7 antigen to regulate T cell interactions with B7 positive cells. The ligand is the CTLA4Ig fusion protein, or the CD28/CTLA4Ig fusion protein hybrid, or a monoclonal antibody reactive with B7 antigen.

A monoclonal antibody reactive with soluble CTLA4 fusion protein and a monoclonal antibody reactive with soluble CD28/CTLA4 fusion protein are described for use in regulating cellular interactions.

A novel Chinese Hamster Ovary cell line stably expressing the CTLA4Ig fusion protein is also disclosed.

BRIEF DESCRIPTION OF THE FIGURES

FIG. 3 depicts the complete amino acid sequence encoding human CTLA4 receptor (SEQ ID NOs: 13 and 14) fused to the oncostatin M signal peptide (position −25 to −1), and including the newly identified N-linked glycosylation site (position 109–111), as described in Example 3, infra.

FIGS. 11A, 11B, and 11C are line graphs showing the survival of human pancreatic islet xenografts.

FIG. 15 is a graph showing the sequencing alignment of CD28 and CTLA4 family members. Sequences of human (H) (SEQ ID NO:25), mouse (M) (SEQ ID NO:23), rat (R) (SEQ ID NO:24), and chicken (Ch) (SEQ ID NO:26) CD28 are aligned with human (SEQ ID NO:21) and mouse (SEQ ID NO:22) CTLA4. Residues are numbered from the mature protein N-terminus with the signal peptides and transmembrane domains underlined and the CDR-analogous regions noted. Dark shaded areas highlight complete conservation of residues while light shaded areas highlight conservative amino acid substitutions in all family members.

FIG. 26 is a nucleic acid sequence encoding the CTLA4-ova fusion protein containing an amino terminal CTLA4 domain and an ovalbumin carboxy-terminal domain (SEQ ID NO:17).

FIG. 27 is a nucleic acid acid sequence encoding the CTLA4-env gp120 fusion protein containing an amino terminal CTLA4 domain (SEQ ID NO:18) and an env gp120 carboxy-terminal domain.

FIG. 28 is a FACS analysis showing that CTLA4-ova binds immobilized B7. The antibody in the ELISA assay recognizes and binds the ovalbumin portion of soluble CTLA4-ova.

FIG. 29 is a FACS analysis showing that CTLA4-E7 binds immobilized B7. The antibody in the FACS assay recognizes and binds the E7 portion of soluble CTLA4-E7.

FIG. 30 is a FACS analysis showing that CTLA4-env gp120 binds immobilized B7. The antibody in the FACS assay reconizes and binds the V3 loop of env gp120 portion of soluble CTLA4-env gp120.

FIG. 31 is a FACS analysis showing that CTLA4-p97 binds immobilized B7. The antibody in the FACS assay recognizes and binds the p97 portion of soluble CTLA4-p97.

FIG. 33 is a line graph showing that soluble CTLA4-env gp120 (closed circle) binds immobilized B7 in an ELISA assay. The antibody in the ELISA assay recognizes and binds the V3 loop of env gp120 portion of soluble CTLA4-env gp120.

FIG. 36 is the amino acid sequence of the CTLA4/p97 fusion protein containing an amino terminal CTLA4 domain and a p97 carboxy-terminal domain (SEQ ID NO:19).

FIG. 37 is the amino acid sequence of the CTLA4-E7 fusion protein containing an amino terminal CTLA4 domain and an E7 carboxy-terminal domain (SEQ ID NO:20).

DETAILED DESCRIPTION OF THE INVENTION

Definition

Figure 1:
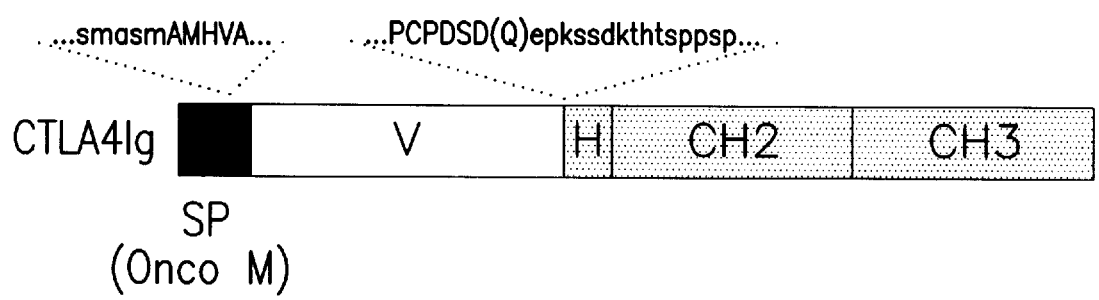
FIG. 1 is a diagrammatic representation of CTLA4Ig fusion constructs as described in Example 2, infra.

As used in this application, the following words or phrases have the meanings specified.

As used herein "blocking B7 interaction" means to interfere with the binding of the B7 antigen to its ligands such as CD28 and/or CTLA4 thereby obstructing T cell and B cell interaction.

As used herein a "B7-binding molecule" means any molecule which will bind the B7 antigen.

As used herein a "CTLA4 mutant" means a molecule having amino acids which are similar to the amino acid sequence of the extracellular domain of CTLA4 so that the molecule recognizes and binds a B7 antigen.

As used herein a "CD28 mutant" means a molecule having amino acids which are similar to the amino acid sequence of the extracellular domain of CD28 so that the molecule recognizes and binds a B7 antigen.

As used herein a "CTLA4/CD28 hybrid fusion protein" is a molecule having at least portions of the extracellular domains of both CTLA4 and CD28 so that the molecule recognizes and binds a B7 antigen.

As used herein a "non-CTLA4 protein sequence" means any molecule which does not bind B7 and does not interfere with the binding of CTLA4 to its B7 antigen target.

As used herein "the extracellular domain of CTLA4" is any portion of CTLA4 which recognizes and binds the B7 antigen. For example, an extracellular domain of CTLA4 is that portion which is encoded by amino acid residues from about position 1 to about position 125 of the amino acid sequence corresponding to the extracellular domain of CTLA4 (FIG. 3).

As used herein "reactive with" means recognizes and binds its target.

As used herein a "fragment of CTLA4" is the extracellular domain of CTLA4 or portion thereof that recognizes and binds its target, e.g., the B7 antigen.

As used herein a "derivative of CTLA4" is a molecule that shares at least 7% sequence homology with CTLA4 and functions like CTLA4, i.e., it recognizes and binds the B7 antigen.

As used herein "blocks T cell proliferation" means to bind the B7 antigen on the B cell surface so that T cell proliferation is detectably inhibited by an art recognized test such as by nucleotide incorporation into DNA or clonogenic assay.

As used herein "regulating functional CTLA4 positive T cell interaction" means to suppress an immune response directly or indirectly.

As used herein "at least a portion" means any part of the molecule which recognizes and binds its target, e.g., the B7 antigen.

As used herein "anti-BB1 monoclonal antibody" is an antibody which specifically recognizes and binds the BB1 antigen (also known as the B7 antigen).

As used herein "corresponding" means to share sequence identity.

As used herein "immunoproliferative disease" means any disease mediated by T cell interactions with B7 positive cells including but not limited to graft versus host disease (GVHD); psoriasis; immune disorders associated with graft transplantation rejection; T cell lymphoma; T cell acute lymphoblastic leukemia; testicular angiocentric T cell lymphoma; benign lymphocytic angiitis; and autoimmune diseases such as lupus erythematosus, Hashimoto's thyroiditis, primary myxedema, Graves' disease, pernicious anemia, autoimmune atrophic gastritis, Addison's disease, insulin dependent diabetes mellitus, good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatoid arthritis, polymyositis, scleroderma, and mixed connective tissue disease.

As used herein "functional" means to be able to carry out normal activities, such as to recognize and bind a target.

As used herein "soluble CTLA4" means circulating CTLA4 including but not limited to CTLA4Ig, CTLA4-env gp120, CTLA4-p97, CTLA4-ova, CTLA4-E7, the extracellular domain of CTLA4, or the extracellular domain of CTLA4 fused (genetically or chemically) to a biologically or chemically active molecule.

As used herein "joined" means to combine using genetic engineering techniques.

In order that the invention herein described may be more fully understood, the following description is set forth.

Compositions of the Invention

This invention is directed to the isolation and expression of the human CTLA4 receptor found on T cell surfaces, which binds to the B7 antigen expressed on activated B cells, and cells of other lineages, and to expression of soluble fusion protein products of the CTLA4 receptor gene. The invention also provides methods for using the expressed CTLA4 receptor to regulate cellular interactions, including T cell interactions with B7 positive cells.

The present invention provides the first protein product of CTLA4 transcripts in the form of a soluble fusion protein. The CTLA4Ig protein forms a disulfide-linked dimer having two subunits, each of which has an $M_r$ of approximately 50,000 indicating that native CTLA4 probably exists on the T cell surface as a disulfide-linked homodimer.

B7 antigen has been shown to be a ligand for CD28 receptor on T cells (Linsley et al., Proc. Natl. Acad. Sci. USA, supra). The CTLA4 receptor molecule appears functionally and structurally related to the CD28 receptor; both are receptors for the B cell activation antigen, B7, while CTLA4 appears to have higher affinity for B7, among the highest yet reported for lymphoid adhesion systems. CTLA4Ig was shown to bind more strongly to B7 positive (B7$^+$) cell lines than CD28Ig. Other experiments demonstrated that CTLA4 is a higher affinity receptor for B7 antigen than CD28 receptor. Additionally, CTLA4Ig was shown to bind a single protein on lymphoblastoid cells which is similar in size to the B7 antigen. CTLA4Ig inhibited T cell proliferation and inhibited $T_h$-induced IgM production.

In another preferred embodiment, hybrid fusion proteins having amino acid sequences corresponding to fragments of different receptor proteins were constructed. For example, amino acid sequences corresponding to selected fragments of the extracellular domains of CD28 and CTLA4 were linked to form soluble CD28/CTLA4 hybrid fusion proteins, e.g. a CD28/CTLA4Ig fusion protein. This protein was obtained having a first amino acid sequence containing amino acid residues corresponding to a fragment of the extracellular domain of CD28 joined to a second amino acid sequence corresponding to a fragment of the extracellular domain of CTLA4Ig and to a third amino acid sequence corresponding to the hinge, CH2 and CH3 regions of human IgCγ1.

One embodiment of the hybrid fusion proteins is a CD28/CTLA4Ig fusion construct having a first amino acid sequence containing amino acid residues from about position 1 to about position 94 of the amino acid sequence corresponding to the extracellular domain of CD28, joined to a second amino acid sequence containing amino acid residues from about position 94 to about position 125 of the amino acid sequence corresponding to the extracellular domain of CTLA4, joined to a third amino acid sequence corresponding to the hinge, CH2 and CH3 regions of human IgCγ1.

In a preferred embodiment, the complete and correct DNA sequence encoding the amino acid sequence corresponding to human CTLA4 receptor protein of the invention is cloned using PCR. The cDNA containing the complete predicted coding sequence of CTLA4 was assembled from two PCR fragments amplified from H38 RNA, and inserted into the expression vector, CDM8 as described in detail in the Examples, infra.

Isolates were transfected into COS cells and tested for binding of B7Ig, a soluble fusion protein having an amino acid sequence corresponding to the extracellular domain of B7 and a human immunoglobulin (Ig) Cγ1 region, as described by Linsley et al., J. Exp. Med. 173:721–730 (1991).

DNA encoding the amino acid sequence corresponding to the CTLA4Ig fusion protein has been deposited with the American Type Culture Collection (ATCC) in Rockville, Md. 20852, under the provisions of the Budapest Treaty on May 31, 1991 and has been accorded ATCC accession number: 68629.

The DNA sequence of one isolate, designated as OMCTLA4, was then determined and found to correspond exactly to the predicted human CTLA4 sequence, fused at the N-terminus to the signal peptide from oncostatin M. The CTLA4 receptor is encoded by 187 amino acids (exclusive of the signal peptide and stop codons) and includes a newly identified N-linked glycosylation site at amino acid positions 109–111 (see FIG. 3, infra). The CTLA4 receptor is expressed using the oncostatin M signal peptide. Other signal peptides may be used. These include the CD5 leader sequence and any leader sequence of any extracellular protein.

In one embodiment, soluble CTLA4Ig fusion protein is encoded by a first amino acid sequence containing amino acid residues from about position 1 to about position 125 of the amino acid sequence corresponding to the extracellular domain of CTLA4 joined to a second amino acid sequence containing amino acid residues corresponding to the hinge, CH2 and CH3 regions of human IgCγ1. The fusion protein is preferably produced in dimeric form. The construct was then transfected into COS or CHO cells, and CTLA4Ig was purified and identified as a dimer.

Other soluble CTLA4 molecules include but are not limited to a molecule having the extracellular portion of CTLA4, CTLA4-p97, CTLA4-env gp120, CTLA4-ova, CTLA4-E7. Vector constructs of these soluble CTLA4 molecules are shown in FIGS. 1, 21–25.

In accordance with the practice of this invention, soluble CTLA4 molecules of the invention may have amino acid substitutions in the amino acid sequence corresponding to the external domain of CTLA4 so as to produce molecules which would retain the functional property of CTLA4, namely, the molecule having such substitutions will still bind the B7 antigen. These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

In fact, using the methodologies disclosed herein, mutants of the B7-binding molecule were produced. One mutant comprises (1) a sequence beginning with the amino acid at position 1 and ending with the amino acid at position 95 of the CD28 receptor protein; (2) a sequence beginning with the amino acid at position 95 and ending with amino acid at position 125 of the extracellular domain of CTLA4; and (3) a sequence corresponding to the human IgCγ1 domain.

The second mutant comprises (1) a sequence beginning with the amino acid at position 1 and ending with the amino acid at position 95 of the CD28 receptor protein; (2) a sequence beginning with the amino acid at position 95 and ending with amino acid at position 120 of the extracellular domain of CTLA4; and (3) a sequence corresponding to the human IgCγ1 domain.

Methods of Making Compositions of the Invention

Methods for making soluble molecules in general are well established (A. Traunecker et al. (1991) EMBO Journal 10(12):3655–3659; A. Traunecker et al. "Bispecific single chain molecules (Janusins) target cytotoxic lymphocytes on HIV infected cells, EMBO Journal 10(12):3655–3659; Neuberger et al., "Recombinant Antibodies Possessing Novel Effector Functions", Nature, 312: 604–608 (1984); and Oi et al., "Chimeric Antibodies", Biotechniques, 4 (3):214–21 (1986); Ernst Winnacker, "From Genes to Clones: Introduction to Gene Technology" Chapter 7, 1987 at pages 239–317; Senter et al., "Anti-Tumor Effects Of Antibody-Alkaline Phosphatase", Proc. Natl. Acad. Sci. USA. 85:4842–46 (1988); "Enhancement of the in vitro and in vivo Antitumor Activities of Phosphorylated Mitomycin C and Etoposide Derivatives by Monoclonal Antibody-Alkaline Phosphatase Conjugates", Cancer Research 49:5789–5792 (1989); and Senter, "Activation of Prodrugs by Antibody-Enzyme Conjugates: A New Approach to Cancer Therapy, FASEB J. 4:188–193 (1990); Ramsay et al., "Bone Marrow Purging Using Monoclonal Antibodies", J. Clin. Immunol. 8(2):81–88 (1988); Morrison, S. L., Johnson, M. J., Herzenberg, L. A., and Oi, V. T. (1984). "Chimeric human antibody molecules: Mouse antigen-binding domains with human constant region domains." Proc. Natl. Acad. Sci. USA 81, 6851–6855; Morrison, S. L. (1985). "Transfectomas provide novel chimeric antibodies." Science 229, 1202–1207; Haber et al., 1990).

The starting material can be a cDNA clone of CTLA. Using methods known in the art a restriction site can be positioned close to a start codon. The next step can be a digestion step which should cut DNA fragments asymmetrically. The mixture of DNA fragments obtained is then cloned into a vector, e.g., a pUC vector. Of course, a cleavage site must be present within the polylinker of a chosen vector. Since a wide spectrum of vectors are available, it should not be difficult to find a suitable vector containing the desired cleavage site. Once a suitable clone is identified, the cleavage site can be used for the insertion of the gene of interest, which can be obtained from the original cDNA clone.

Soluble forms of the protein product of the CTLA4 receptor gene (e.g., CTLA4Ig) may be prepared using fusion proteins having a first amino acid sequence corresponding to the extracellular domain of CTLA4 and a second amino acid sequence corresponding to an Ig domain, for example, the human IgCγ1 domain. Other soluble forms of CTLA4 may be prepared using a polypeptide tag expressed at the carboxy terminus of CTLA4.

Cloning and expression plasmids (CDM8 and πLN) were constructed containing cDNAs encoding portions of the amino acid sequence corresponding to human CTLA4 receptor based on the cDNA sequence described herein, where the cDNA encoding a first amino acid sequence corresponding to a fragment of the extracellular domain of the CTLA4 receptor gene is joined to DNA encoding a second amino acid sequence corresponding to an IgC region that permits the expression of the CTLA4 receptor gene by altering the solubility of the expressed CTLA4 protein.

The techniques for cloning and expressing DNA sequences encoding the amino acid sequences corresponding to the CTLA4 receptor protein, soluble fusion proteins and hybrid fusion proteins, e.g synthesis of oligonucleotides, PCR, transforming cells, constructing vectors, expression systems, and the like are well-established in the art, and most practitioners are familiar with the standard resource materials for specific conditions and procedures. However, the following paragraphs are provided for convenience and notation of modifications where necessary, and may serve as a guideline.

Cloning and Expression of Coding Sequences for Receptors and Fusion Proteins

Fusion protein constructs corresponding to CD28IgCγ1 and B7IgCγ1 for characterizing the CTLA4Ig of the present invention, and for preparing CD28/CTLA4 hybrid fusion proteins, were prepared as described by Linsley et al., J.

*Exp. Med.* 173:721–730 (1991), incorporated by reference herein. Alternatively, cDNA clones may be prepared from RNA obtained from cells expressing B7 antigen and CD28 receptor based on knowledge of the published sequences for these proteins (Aruffo and Seed, and Freeman, supra) using standard procedures.

CTLA4Ig fusions consisting of DNA encoding amino acid sequences corresponding to the extracellular domain of CTLA4 and the hinge, CH2 and CH3 regions of human IgCγ1 were constructed by ligation of PCR fragments. The cDNA encoding the amino acid sequences is amplified using the polymerase chain reaction ("PCR") technique (U.S. Pat. Nos. 4,683,195 and 4,683,202 to Mullis et al. and Mullis & Faloona, *Methods Enzymol.* 154:335–350 (1987)). CTLA4Ig fusion polypeptides were obtained having DNA encoding amino acid sequences containing amino acid residues from about position 1 to about position 125 of the amino acid sequence corresponding to the extracellular domain of CTLA4 and DNA encoding amino acid sequences corresponding to the hinge, CH2 and CH3 regions of Ig Cγ1.

Because the expression of CTLA4 receptor protein in human lymphoid cells has not been previously reported, it was necessary to locate a source of CTLA4 mRNA. PCR cDNA made from the total cellular RNA of several human leukemia cell lines was screened, using as primers, oligonucleotides from the published sequence of the CTLA4 gene (Dariavach et al., supra). Of the cDNA tested, H38 cells (an HTLV II-associated leukemia line) provided the best yield of PCR products having the expected size. Since a signal peptide for CTLA4 was not identified in the CTLA4 gene, the N terminus of the predicted sequence of CTLA4 was fused to the signal peptide of oncostatin M (Malik et al., *Molec. and Cell. Biol.* 9:2847 (1989)) in two steps using oligonucleotides as described in the Examples, infra. The product of the PCR reaction was ligated with cDNA encoding the amino acid sequences corresponding to the hinge, CH2 and CH3 regions of Ig Cγ1 into an expression vector, such as CDM8 or πLN.

To obtain DNA encoding full length human CTLA4, a cDNA encoding the transmembrane and cytoplasmic domains of CTLA4 was obtained by PCR from H38 cells and joined with a fragment from CTLA4Ig, obtained as described above, encoding the oncostatin M signal peptide fused to the N terminus of CTLA4, using oligonucleotide primers as described in the Examples, infra. PCR fragments were ligated into the plasmid CDM8, resulting in an expression plasmid encoding the full length CTLA4 gene, and designated OMCTLA4.

For construction of DNA encoding the amino acid sequence corresponding to hybrid fusion proteins, DNA encoding amino acids corresponding to portions of the extracellular domain of one receptor gene is joined to DNA encoding amino acids corresponding to portions of the extracellular domain of another receptor gene, and to DNA encoding the amino acid sequences corresponding to the hinge, CH2 and CH3 regions of human IgCγ1 using procedures as described above for the B7Ig, CD28Ig and CTLA4Ig constructs. Thus, for example, DNA encoding amino acid residues from about position 1 to about position 94 of the amino acid sequence corresponding to the extracellular domain of the CD28 receptor is joined to DNA encoding amino acid residues from about position 94 to about position 125 of the amino acid sequence corresponding to the extracellular domain of the CTLA4 receptor and to DNA encoding the amino acid sequences corresponding to the hinge, CH2 and CH3 regions of human IgCγ1.

To produce large quantities of cloned DNA, vectors containing DNA encoding the fusion constructs of the invention are transformed into suitable host cells, such as the bacterial cell line *E. coli* strain MC1061/p3 (Invitrogen Corp., San Diego, Calif.) using standard procedures, and colonies are screened for the appropriate plasmids.

The clones containing DNA encoding fusion constructs obtained as described above are then transfected into suitable host cells for expression. Depending on the host cell used, transfection is performed using standard techniques appropriate to such cells. For example, transfection into mammalian cells is accomplished using DEAE-dextran mediated transfection, $CaPO_4$ co-precipitation, lipofection, electroporation, or protoplast fusion, and other methods known in the art including: lysozyme fusion or erythrocyte fusion, scraping, direct uptake, osmotic or sucrose shock, direct microinjection, indirect microinjection such as via erythrocyte-mediated techniques, and/or by subjecting host cells to electric currents. The above list of transfection techniques is not considered to be exhaustive, as other procedures for introducing genetic information into cells will no doubt be developed.

Expression in eukaryotic host cell cultures derived from multicellular organisms is preferred (*Tissue Cultures*, Academic Press, Cruz and Patterson, Eds. (1973)). These systems have the additional advantage of the ability to splice out introns and thus can be used directly to express genomic fragments. Useful host cell lines include Chinese hamster ovary (CHO), monkey kidney (COS), VERO and HeLa cells. In the present invention, cell lines stably expressing the fusion constructs are preferred.

Expression vectors for such cells ordinarily include promoters and control sequences compatible with mammalian cells such as, for example, CMV promoter (CDM8 vector) and avian sarcoma virus (ASV) (πLN vector). Other commonly used early and late promoters include those from Simian Virus 40 (SV 40) (Fiers, et al., *Nature* 273:113 (1973)), or other viral promoters such as those derived from polyoma, Adenovirus 2, and bovine papilloma virus. The controllable promoter, hMTII (Karin, et al., *Nature* 299:797–802 (1982)) may also be used. General aspects of mammalian cell host system transformations have been described by Axel (U.S. Pat. No. 4,399,216 issued Aug. 16, 1983). It now appears, that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eukaryotes.

Although preferred host cells for expression of the fusion constructs include eukaryotic cells such as COS or CHO cells, other eukaryotic microbes may be used as hosts. Laboratory strains of *Saccharomyces cerevisiae*, Baker's yeast, are most used although other strains such as *Schizosaccharomyces pombe* may be used. Vectors employing, for example, the 2μ origin of replication of Broach, *Meth. Enz.* 101:307 (1983), or other yeast compatible origins of replications (for example, is Stinchcomb et al., *Nature* 282:39 (1979)); Tschempe et al., *Gene* 10:157 (1980); and Clarke et al., *Meth. Enz.* 101:300 (1983)) may be used. Control sequences for yeast vectors include promoters for the synthesis of glycolytic enzymes (Hess et al., *J. Adv. Enzyme Reg.* 7:149 (1968); Holland et al., *Biochemistry* 17:4900 (1978)). Additional promoters known in the art include the CMV promoter provided in the CDM8 vector (Toyama and Okayama, *FEBS* 268:217–221 (1990); the promoter for 3-phosphoglycerate kinase (Hitzeman et al., *J. Biol. Chem.* 255:2073 (1980)), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

Alternatively, prokaryotic cells may be used as hosts for expression. Prokaryotes most frequently are represented by various strains of E. coli; however, other microbial strains may also be used. Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al., Nature 198: 1056 (1977)), the tryptophan (trp) promoter system (Goeddel et al., Nucleic Acids Res. 8:4057 (1980)) and the lambda derived $P_L$ promoter and N-gene ribosome binding site (Shimatake et al., Nature 292:128 (1981)).

The nucleotide sequences encoding CD28Ig and CTLA4Ig proteins, and fusion hybrid proteins such as CD28/CTLA4Ig and mutants thereof, may be expressed in a variety of systems as set forth below. The cDNA may be excised by suitable restriction enzymes and ligated into suitable prokaryotic or eukaryotic expression vectors for such expression.

A stable CHO line of the invention, designated Chinese Hamster Ovary Cell Line CTLA4Ig-24, is preferred for expression of CTLA4Ig and has been deposited with the ATCC under the terms of the Budapest Treaty on May 31, 1991, and accorded ATCC accession number 10762.

Expression of the CTLA4 receptor of the invention is accomplished by transfecting a cell line such as COS cells, and detecting expression by binding of the CTLA4-transfected cells to a ligand for the CTLA4 receptor, for example by testing for binding of the cells to B7Ig fusion protein.

Sequences of the resulting constructs are confirmed by DNA sequencing using known procedures, for example as described by Sanger et al., Proc. Natl. Acad. Sci. USA 74:5463 (1977), as further described by Messing et al., Nucleic Acids Res. 9:309 (1981), or by the method of Maxam et al. Methods Enzymol. 65:499 (1980)).

Recovery of Protein Products

As noted above, CD28 and CTLA4 receptor genes are not readily expressed as mature proteins using direct expression of DNA encoding the truncated protein. To enable homodimer formation, DNA encoding the amino acid sequence corresponding to the extracellular domains of CD28 and CTLA4, and including the codons for a signal sequence such as that of oncostatin M in cells capable of appropriate processing, is fused with DNA encoding the amino acid sequence corresponding to the Fc domain of a naturally dimeric protein. Purification of these fusion protein products after secretion from the cells is thus facilitated using antibodies reactive with the anti-immunoglobulin portion of the fusion proteins. When secreted into the medium, the fusion protein product is recovered using standard protein purification techniques, for example by application to protein A columns.

Making Monoclonal Antibodies of the invention

Monoclonal antibodies reactive with CTLA4 receptor, may be produced by hybridomas prepared using known procedures, such as those introduced by Kohler and Milstein (Kohler and Milstein, Nature, 256:495–97 (1975)), and modifications thereof, to regulate cellular interactions.

These techniques involve the use of an animal which is primed to produce a particular antibody. The animal can be primed by injection of an immunogen (e.g. the B7Ig fusion protein, CTLA4Ig fusion protein or CD28/CTLA4Ig hybrid fusion protein or other functional, soluble forms thereof) to elicit the desired immune response, i.e. production of antibodies from the primed animal. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653, Sp2/0-Ag14, or HL1-653 myeloma lines. These myeloma lines are available from the ATCC, Rockville, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of the desired specificity, e.g. by immunoassay techniques using the CTLA4Ig protein that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (Zola et al., in Monoclonal Hybridoma Antibodies: Techniques and Applications, Hurell (ed.) pp. 51–52 (CRC Press, 1982)). Hybridomas produced according to these methods can be propagated in vitro or in vivo (in ascites fluid) using techniques known in the art (Fink et al., Prog. Clin. Pathol., 9:121–33 (1984), FIG. 6-1 at p. 123).

Generally, the individual cell line may be propagated in vitro, for example, in laboratory culture vessels, and the culture medium containing high concentrations of a single specific monoclonal antibody can be harvested by decantation, filtration, or centrifugation.

In addition, fragments of these antibodies containing the active binding region reactive with the extracellular domain of CTLA4 receptor, such as Fab, F(ab')$_2$ and Fv fragments may be produced. Such fragments can be produced using techniques well established in the art (e.g. Rousseaux et al., in Methods Enzymol., 121:663–69, Academic Press (1986)).

Methods for using the Compositions of the Invention

CTLA4Ig fusion protein and/or fragments of the fusion protein may be used to react with B7 positive cells, such as B cells, to regulate immune responses mediated by T cell interactions with the B7 antigen positive cells or in vitro for leukocyte typing so as to define B cell maturational stages and/or B cell associated diseases (Yokochi et al. J. Immuno. 128(2):823. Surface immunostaining of leukocytes is accomplished by immunofluorescent technology or immunoenzymatic methods but other means of detection are possible.

Soluble CTLA4 proteins and CTLA4/CD28 hybrid fusion proteins, and/or fragments and derivatives of these proteins, may also be used to react with B7 positive cells, including B cells, to regulate immune responses mediated by T cell dependent B cell responses. A fragment of the soluble CTLA4 protein that may be used is a polypeptide having an amino acid sequence corresponding to some portion of the amino acid sequence corresponding to the CTLA4 receptor used to obtain the soluble CTLA4 protein as described herein.

The B7 antigen expressed on activated B cells and cells of other lineages, and the CD28 receptor expressed on T cells, can directly bind to each other, and this interaction can mediate cell-cell interaction. Such interactions directly trigger the CD28 activation pathway in T cells, leading to cytokine production, T cell proliferation, and B cell differentiation into immunoglobulin producing cells. The activation of B cells that occurs, can cause increased expression of B7 antigen and further CD28 stimulation, leading to a state of chronic inflammation such as in autoimmune diseases, allograft rejection, graft versus host disease or chronic allergic reactions. Blocking or inhibiting this reaction may be effective in preventing T cell cytokine production and thus preventing or reversing inflammatory reactions.

Soluble CTLA4, e.g. CTLA4Ig, is shown herein to be a potent inhibitor of in vitro lymphocyte functions requiring T and B cell interaction. This indicates the importance of interactions between the B7 antigen and its counter-receptors, CTLA4 and/or CD28. The cytoplasmic domains of murine and human CTLA4 are similar (Dariavach et al., supra, 1988), suggesting that this region has important functional properties. The cytoplasmic domains of CD28 and CTLA4 also share homology.

CTLA4 is a more potent inhibitor in vitro of lymphocyte responses than either anti-BB1, or anti-CD28 mabs. CTLA4Ig does not have direct stimulatory effects on T cell proliferation to counteract its inhibitory effects. Therefore, the CTLA4 fusion proteins may perform as a better inhibitor in vivo than anti-CD28 monoclonal antibodies. The immunosuppressive effects of CTLA4 fusion proteins (e.g., CTLA4Ig) in vitro suggests its use in therapy for treatment of autoimmune disorders involving abnormal T cell activation or Ig production.

The soluble CTLA4 fusion proteins is expected to exhibit inhibitory properties in vivo (as confirmatory data see P. S. Linsley et al. "Immunosuppression in vivo by a soluble form of the CTLA4 cell activation molecule" Science (1992) 257(5071)792–795. Thus, it is expected that soluble CTLA4 will act to inhibit T cells in a manner similar to the effects observed for the anti-CD28 antibody, under similar conditions in vivo. Under conditions where T cell/B cell interactions are occurring as a result of contact between T cells and B cells, binding of introduced CTLA4Ig to react with B7 antigen positive cells, for example B cells, may interfere, i.e. inhibit, the T cell/B cell interactions resulting in regulation of immune responses (P. S. Linsley (1992), supra). Because of this exclusively inhibitory effect, CTLA4Ig is expected to be useful in vivo as an inhibitor of T cell activity, over non-specific inhibitors such as cyclosporine and glucosteroids.

In one embodiment, the CTLA4Ig fusion protein or CTLA4/CD28Ig hybrid proteins, may be introduced in a suitable pharmaceutical carrier in vivo, i.e. administered into a subject, e.g., a human subject, for treatment of pathological conditions such as immune system diseases or cancer (Examples 8 and 9, infra; for confirmatory data see P. M. Wallace et al. "CTLA4Ig Treatment Ameliorates The Lethality Of Murine Graft Versus Host Diseases Across Major Histocompatibility Barriers" Transplantation (1994) 58(5): 602–10; B. K. Finck et al. "Treatment of Murine Lupus with CTLA4Ig" Science (1994) 265(5176):1225–7; S. F. Bolling et al. "The Effect of Combination Cyclosporine and CTLA4Ig Therapy in Cardiac Allograft Survival" J. Surg. Rsch. (1994) 57(1):60–4; T. C. Pearson et al. "Transplantation Tolerance Induced by CTLA4-Ig" Transplantation (1994) 57(12):1761–6; B. R. Blazer et al. "In Vivo Blockade of CD28/CTLA4: B7/BB1 Interaction With CTLA4-Ig Reduces Lethal Murine Graft-Versus-Host Disease Across the Major Histocompatibility Barrier in Mice" Blood (1994) 83(12):3815–25; K. Nishikawa et al., "Effect of CTLA-4 Chimeric Protein on Rat Autoimmune Anti-glomular Basement Membrane glomerulonephritis," (1994) 24(1): 1249–54; H. Lin et al., "Long-term Acceptance of MHC Mismatched Cardiac Allografts Induced by CTLA4Ig Plus Donor-specific Transfusion," J. Exp. Med. (1993) 175(5): 1801–6; and D. J. Lenschow et al., "Long-Term Survival of Xenogenic Pancreatic Islet Grafts Induced by CTLA4Ig," Science (1992) 257(5071): 789–92).

Introduction of the fusion protein in vivo is expected to result in interference with T cell interactions with other cells, such as B cells, as a result of binding of the ligand to B7 positive cells. The prevention of normal T cell interactions may result in decreased T cell activity, for example, decreased T cell proliferation. In addition, administration of the fusion protein in vivo is expected to result in regulation of in vivo levels of cytokines, including, but not limited to, interleukins, e.g. interleukin ("IL")-2, IL-3, IL-4, IL-6, IL-8, growth factors including tumor growth factor ("TGF"), colony stimulating factor ("CSF"), interferons ("IFNs"), and tumor necrosis factor ("TNF") to promote desired effects in a subject. For example, when the fusion protein is introduced in vivo, it may block production of cytokines, which contribute to malignant growth, for example of tumor cells. The fusion protein may also block proliferation of viruses dependent on T cell activation, such as the virus that causes AIDS, HTLV1.

Under some circumstances, as noted above, the effect of administration of the CTLA4Ig fusion protein or its fragments in vivo is inhibitory, resulting from blocking by the fusion protein of the CTLA4 and CD28 triggering resulting from T cell/B cell contact. For example, the CTLA4Ig protein may block T cell proliferation. Introduction of the CTLA4Ig fusion protein in vivo will thus produce effects on both T and B cell-mediated immune responses. The fusion protein may also be administered to a subject in combination with the introduction of cytokines or other therapeutic reagents.

In an additional embodiment of the invention, other reagents, including derivatives reactive with the CTLA4Ig fusion protein or the CTLA4 receptor are used to regulate T cell interactions. For example, antibodies, and/or antibody fragments reactive with the CTLA4 receptor can be screened to identify those capable of inhibiting the binding of the soluble CTLA4 fusion protein to the B7 antigen. The antibodies or antibody fragments such as Fab or F(ab')$_2$ fragments, may then be used to react with the T cells, for example, to inhibit T cell proliferation.

Anti-B7 monoclonal antibodies prepared as described above can be used to bind to B7 antigen to inhibit interactions of CD28-positive or CTLA4-positive T cells with B7 positive cells. Anti-CTLA4 monoclonal antibodies can be used to bind to CTLA4 receptor to inhibit the interaction of CTLA4-positive T cells with other cells.

In another embodiment, the CTLA4Ig fusion protein may be used to identify additional compounds capable of regulating the interaction between CTLA4 and the B7 antigen. Such compounds may include small naturally occurring molecules that can be used to react with B cells and/or T cells. For example, fermentation broths may be tested for the ability to inhibit CTLA4/B7 interactions. In addition, derivatives of the CTLA4Ig fusion protein as described above may be used to regulate T cell proliferation. For example, the fragments or derivatives may be used to block T cell proliferation in graft versus host (GVH) disease which accompanies allogeneic bone marrow transplantation.

The CD28-mediated T cell proliferation pathway is cyclosporine-resistant, in contrast to proliferation driven by the CD3/Ti cell receptor complex (June et al., 1987, supra). Cyclosporine is relatively ineffective as a treatment for GVH disease (Storb, *Blood* 68:119–125 (1986)). GVH disease is thought to be mediated by T lymphocytes which express CD28 antigen (Storb and Thomas, *Immunol. Rev.* 88:215–238 (1985)). Thus, the CTLA4Ig fusion protein may be useful alone, or in combination with immunosuppressants such as cyclosporine, for blocking T cell proliferation in GVH disease.

Regulation of CTLA4-positive T cell interactions with B7 positive cells, including B cells, by the methods of the invention may thus be used to treat pathological conditions such as autoimmunity, transplantation, infectious diseases and neoplasia.

The B7-binding molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. (Quantitative Comparison of Toxicity of Anticancer Agents in Mouse, Rat, Hamster, Dog, Monkey and Man. Cancer Chemother, Rep., 50, No.4, 219–244, May 1966).

Adjustments in the dosage regimen may be made to optimize the growth inhibiting response. Doses may be divided and administered on a daily basis or the dose may be reduced proportionally depending upon the situation. For example, several divided doses may be administered daily or the dose may be proportionally reduced as indicated by the specific therapeutic situation.

In accordance with the practice of the invention an effective amount for treating a subject may be between about 0.1 and about 10 mg/kg body weight of subject. Also, the effective amount may be an amount between about 1 and about 10 mg/kg body weight of subject.

The soluble CTLA4 molecules of the invention also have in vitro clinical application. They may be useful in the enumeration of B7 positive cells in the diagnosis or prognosis of some conditions of immunodeficiency, the phenotyping of leukemias and lymphomas, and the monitoring of immunological change following organ transplantation.

Advantages of the Invention:

The subject invention overcomes the problems associated with current therapies directed to preventing the rejection of tissue or organ transplants. In contrast to present therapies, the present invention affects only immunological responses mediated by B7 interactions.

For example, the present invention affects the transplant antigen-specific T cells, thus inducing donor-specific and antigen-specific tolerance. The binding of CD28 by its ligand, B7/BB1 (B7), during T cell receptor engagement is critical for proper T cell signaling in some systems (M. K. Jenkins, P. S. Taylor, S. D. Norton, K. B. Urdahl, J. Immunol. 147:2461 (1991); C. H. June, J. A. Ledbetter, P. S. Linsley, C. B. Thompson,Immunol. Today 11:211 (1990); H. Reiser, G. J. Freeman, Z. Razi-Wolf, C. D. Gimmi, B. Benacerraf, L. M. Nadler, Proc. Natl. Acad. Sci. U.S.A. 89:271 (1992); N. K. Damle, K. Klussman, P. S. Linsley, A. Aruffo, J.Immunol. 148:1985 (1992)).

When the interaction of CD28 with its ligand is blocked, antigen-specific T cells are inappropriately induced into a state of antigen-specific T cell anergy (M. K. Jenkins, P. S. Taylor, S. D. Norton, K. B. Urdahl, J. Immunol. 147:2461 (1991); F. A. Harding, J. G. McArthur, J. A. Gross, D. H. Raulet, J. P. Allison, Nature 356:607 (1992)).

CTLA4Ig fusion protein binds to both human and murine B7 (with a 20-fold greater affinity than. CD28), blocks the binding of CD28 to B7, inhibits T cell activation, and induces T cell unresponsiveness in vitro (F. A. Harding, J. G. McArthur, J. A. Gross, D. H. Raulet, J. P. Allison, Nature 356:607 (1992); P. S. Linsley et al., J. Exp. Med. 174:561 (1991).

Moreover, the present invention would be useful to obtain expression of a soluble protein product of the heretofore unexpressed CTLA4 gene, and to identify a natural ligand for CTLA4 that is involved in functional responses of T cells. The soluble protein product could then be used to regulate T cell responses in vivo to treat pathological conditions.

In the soluble form, the CTLA4 protein product is not only easier to purify than non-soluble or cell surface bound CTLA4 but also easier to use and manipulate.

Further, the CTLA4 molecule of the invention is advantageous over naturally occurring CTLA4 because in a therapeutic or diagnostic setting one can administer or provide abundantly more soluble CTLA4 molecule than cell bound CTLA4 to a sample or subject.

The following examples are presented to illustrate the present invention and to assist one of ordinary skill in making and using the same. The examples are not intended in any way to otherwise limit the scope of the invention.

EXAMPLE 1

Preparation of B7Ig and CD28Ig Fusion Proteins

Receptor-immunoglobulin C gamma (IgCγ) fusion proteins B7Ig and CD28Ig were prepared as described by Linsley et al., in *J. Exp. Med.* 173:721–730 (1991), incorporated by reference herein. Briefly, DNA encoding amino acid sequences corresponding to the respective receptor protein (e.g. B7) was joined to DNA encoding amino acid sequences corresponding to the hinge, CH2 and CH3 regions of human IgCγ1. This was accomplished as follows.

Polymerase Chain Reaction (PCR)

For PCR, DNA fragments were amplified using primer pairs as described below for each fusion protein. PCR reactions (0.1 ml final volume) were run in Taq polymerase buffer (Stratagene, La Jolla, Calif.), containing 20 μmoles each of dNTP; 50–100 pmoles of the indicated primers; template (1 ng plasmid or cDNA synthesized from ≦1 μg total RNA using random hexamer primer, as described by Kawasaki in PCR Protocols, Academic Press, pp. 21–27 (1990), incorporated by reference herein); and Taq polymerase (Stratagene). Reactions were run on a thermocycler (Perkin Elmer Corp., Norwalk, Conn.) for 16–30 cycles (a typical cycle consisted of steps of 1 min at 94° C., 1–2 min at 50° C. and 1–3 min at 72° C.).

Plasmid Construction

Expression plasmids containing cDNA encoding CD28, as described by Aruffo and Seed, *Proc. Natl. Acad. Sci. USA* 84:8573 (1987)), were provided by Drs. Aruffo and Seed (Mass General Hospital, Boston, Mass.). Plasmids containing cDNA encoding CD5, as described by Aruffo, *Cell* 61:1303 (1990)), were provided by Dr. Aruffo. Plasmids containing cDNA encoding B7, as described by Freeman et al., *J. Immunol.* 143:2714 (1989)), were provided by Dr. Freeman (Dana Farber Cancer Institute, Boston, Mass.). For initial attempts at expression of soluble forms of CD28 and B7, constructs were made (OMCD28 and OMB7) as described by Linsley et al., *J. Exp. Med.,* supra, in which stop codons were introduced upstream of the transmembrane domains and the native signal peptides were replaced with the signal peptide from oncostatin M (Malik et al., *Mol. Cell Biol.* 9:2847 (1989)). These were made using synthetic oligonucleotides for reconstruction (OMCD28) or as primers (OMB7) for PCR. OMCD28 is a CD28 cDNA modified for more efficient expression by replacing the signal peptide with the analogous region from oncostatin M. CD28Ig and B7Ig fusion constructs were made in two parts. The 5' portions were made using OMCD28 and OMB7 as templates and the oligonucleotide, CTAGCCACTGAAGCT-TCACCATGGGTGTACTGCTCACAC (SEQ ID NO:1), (encoding the amino acid sequence corresponding to the oncostatin M signal peptide) as a forward primer, and either TGGCATGGGCTCCTGATCAGGCTTA-GAAGGTCCGGGAAA (SEQ ID NO:2), or, TTTGGGCTCCTGATCAGGAAAATGCTCT-TGCTTGGTTGT (SEQ ID NO:3) as reverse primers, respectively. Products of the PCR reactions were cleaved with restriction endonucleases (Hind III and BclI) as sites introduced in the PCR primers and gel purified.

The 3' portion of the fusion constructs corresponding to human IgCγ1 sequences was made by a coupled reverse transcriptase (from Avian myeloblastosis virus; Life Sciences Associates, Bayport, N.Y.)-PCR reaction using RNA from a myeloma cell line producing human-mouse chimeric mAb L6 (provided by Dr. P. Fell and M. Gayle, Bristol-Myers Squibb Company, Pharmaceutical Research Institute, Seattle, Wash.) as template. The oligonucleotide, AAG-CAAGAGCATTTTCCTGATCAGGAGC-CCAAATCTTCTGACAAAACTCACACATC-CCCACCGTCCCCAGCACCTGAACTCCTG (SEQ ID NO:4), was used as forward primer, and CTTCGAC-CAGTCTAGAAGCATCCTCGTGCGACCGCGAGAGC (SEQ ID NO:5) as reverse primer. Reaction products were cleaved with BclI and XbaI and gel purified. Final constructs were assembled by ligating HindIII/BclI cleaved fragments containing CD28 or B7 sequences together with BclI/XbaI cleaved fragment containing IgCγ1 sequences into HindIII/XbaI cleaved CDM8. Ligation products were transformed into MC1061/p3 *E. coli* cells and colonies were screened for the appropriate plasmids. Sequences of the resulting constructs were confirmed by DNA sequencing.

The construct encoding B7 contained DNA encoding amino acids corresponding to amino acid residues from approximately position 1 to approximately position 215 of the extracellular domain of B7. The construct encoding CD28 contained DNA encoding amino acids corresponding to amino acid residues from approximately position 1 to approximately position 134 of the extracellular domain of CD28.

CD5Ig was constructed in identical fashion, using CAT-TGCACAGTCAAGCTTCCATGC-CCATGGGTTCTCTGGCCACCTTG (SEQ ID NO:6), as forward primer and ATCCACAGTGCAGTGATCATTTG-GATCCTGGCATGTGAC (SEQ ID NO:7) as reverse primer. The PCR product was restriction endonuclease digested and ligated with the IgCγ1 fragment as described above. The resulting construct (CD5IG) encoded a mature protein having an amino acid sequence containing amino acid residues from position 1 to position 347 of the sequence corresponding to CD5, two amino acids introduced by the construction procedure (amino acids DQ), followed by DNA encoding amino acids corresponding to the IgCγ1 hinge region.

Cell Culture and Transfections

COS (monkey kidney cells) were transfected with expression plasmids expressing CD28 and B7 using a-modification of the protocol of Seed and Aruffo (*Proc. Natl. Acad. Sci.* 84:3365 (1987)), incorporated by reference herein. Cells were seeded at 106 per 10 cm diameter culture dish 18–24 h before transfection. Plasmid DNA was added (approximately 15 μg/dish) in a volume of 5 mls of serum-free DMEM containing 0.1 mM chloroquine and 600 μg/ml DEAE Dextran, and cells were incubated for 3–3.5 h at 37° C. Transfected cells were then briefly treated (approximately 2 min) with 10% dimethyl sulfoxide in PBS and incubated at 37° C. for 16–24 h in DMEM containing 10% FCS. At 24 h after transfection, culture medium was removed and replaced with serum-free DMEM (6 ml/dish). Incubation was continued for 3 days at 37° C., at which time the spent medium was collected and fresh serum-free medium was added. After an additional 3 days at 37° C., the spent medium was again collected and cells were discarded.

CHO cells expressing CD28, CD5 or B7 were isolated as described by Linsley et al., (1991) supra, as follows: Briefly, stable transfectants expressing CD28, CDS, or B7, were isolated following cotransfection of dihydrofolate reductase-deficient Chinese hamster ovary (dhfr⁻ CHO) cells with a mixture of the appropriate expression plasmid and the selectable marker, pSV2dhfr (Linsley et al., *Proc. Natl. Acad. Sci. U.S.A.* 87:5031 (1990)), incorporated by reference herein. Transfectants were then grown in increasing concentrations of methotrexate to a final level of 1 μM and were maintained in DMEM supplemented with 10% fetal bovine serum (FBS), 0.2 mM proline and 1 μM methotrexate. CHO lines expressing high levels of CD28 (CD28⁺ CHO) or B7 (B7⁺ CHO) were isolated by multiple rounds of fluorescence-activated cell sorting (FACS®) following indirect immunostaining with mAbs 9.3 or BB-1. Amplified CHO cells negative for surface expression of CD28 or B7 (dhfr⁺ CHO) were also isolated by FACS® from CD28-transfected populations.

Immunostaining and FACS® Analysis

Transfected CHO or COS cells or activated T cells were analyzed by indirect immunostaining. Before staining, CHO cells were removed from their culture vessels by incubation in PBS containing 10 mM EDTA. Cells were first incubated with murine mabs 9.3 (Hansen et al., *Immunogenetics* 10:247 (1980)) or BB-1 (Yokochi et al., *J. Immunol.* 128:823 (1981)), or with Ig fusion proteins (all at 10 μg/ml in DMEM containing 10% FCS) for 1–2 h at 4° C. Cells were then washed, and incubated for an additional 0.5–2 h at 4° C. with a FITC-conjugated second step reagent (goat anti-mouse Ig serum for murine mAbs, or goat anti-human Ig Cγ serum for fusion proteins (Tago, Inc., Burlingame, Calif.)). Fluorescence was analyzed on a FACS IV® cell sorter (Becton Dickinson and CO., Mountain View, Calif.) equipped with a four decade logarithmic amplifier.

Purification of Ig Fusion Proteins

The first, second and third collections of spent serum-free culture media from transfected COS cells were used as sources for the purification of Ig fusion proteins. After removal of cellular debris by low speed centrifugation, medium was applied to a column (approximately 200–400 ml medium/ml packed bed volume) of immobilized protein A (Repligen Corp., Cambridge, Mass.) equilibrated with 0.05M sodium citrate, pH 8.0. After application of the medium, the column was washed with 1M potassium phosphate, pH 8, and bound protein was eluted with 0.05M sodium citrate, pH 3. Fractions were collected and immediately neutralized by addition of 1/10 volume of 2M Tris, pH 8. Fractions containing the peak of $A_{280}$ absorbing material were pooled and dialyzed against PBS before use. Extinction coefficients of 2.4 and 2.8 ml/mg for CD28Ig and B7Ig, respectively, were determined by amino acid analysis of solutions of known absorbance. The recovery of purified CD28Ig and B7Ig binding activities was nearly quantitative as judged by FACS® analysis after indirect fluorescent staining of $B7^+$ and $CD28^+$ CHO cells.

EXAMPLE 2

Preparation of CTLA4Ig Fusion Protein

A soluble genetic fusion encoding CTLA4Ig between the extracellular domain of CTLA4 and an IgCγ1 domain was constructed in a manner similar to that described above for the CD28Ig construct. The extracellular domain of the CTLA4 gene was cloned by PCR using synthetic oligonucleotides corresponding to the published sequence (Dariavach et al., *Eur. Journ. Immunol.* 18:1901–1905 (1988)).

Because a signal peptide for CTLA4 was not identified in the CTLA4 gene, the N-terminus of the predicted sequence of CTLA4 was fused to the signal peptide of oncostatin M (Malik et al., *Mol. and Cell. Biol.* 9:2847 (1989)) in two steps using overlapping oligonucleotides. For the first step, the oligonucleotide, CTCAGTCTGGTCCTTGCACTCCT-GTTTCCAAGCATGGCGAGCATGGCAATG-CACGTGGCCCAGCC (SEQ ID NO:8) (which encoded the C terminal 15 amino acids from the oncostatin M signal peptide fused to the N terminal 7 amino acids of CTLA4) was used as forward primer, and TTTGGGCTCCTGATCA-GAATCTGGGCACGGTTG (SEQ ID NO:9) (encoding amino acid residues 119–125 of the amino acid sequence encoding CTLA4 receptor and containing a Bcl I restriction enzyme site) as reverse primer. The template for this step was cDNA synthesized from 1 μg of total RNA from H38 cells (an HTLV II infected T cell leukemic cell line provided by Drs. Salahudin and Gallo, NCI, Bethesda, Md.). A portion of the PCR product from the first step was reamplified, using an overlapping forward primer, encoding the N terminal portion of the oncostatin M signal peptide and containing a Hind III restriction endonuclease site, CTAGC-CACTGAAGCTTCACCAATGGGTGTACT-GCTCACACAGAGGACGCTGCTCAGTCTG-GTCCTTGCACTC (SEQ ID NO:10) and the same reverse primer. The product of the PCR reaction was digested with Hind III and Bcl I and ligated together with a Bcl 1/Xba I cleaved cDNA fragment encoding the amino acid sequences corresponding to the hinge, CH2 and CH3 regions of IgCγ1 into the Hind III/Xba I cleaved expression vector, CDM8 or Hind III/Xba I cleaved expression vector πLN (provided by Dr. Aruffo).

A map of the resulting CTLA4Ig fusion construct is shown in FIG. 1. Sequences displayed in this figure show the junctions between CTLA4 (upper case letters, unshaded regions) and the signal peptide, SP, of oncostatin M (dark shaded regions), and the hinge, H, of IgCγ1 (stippled regions). The amino acid in parentheses was introduced during construction. Asterisks (*) indicate cysteine to serine mutations introduced in the IgCγ hinge region. The immunoglobulin superfamily V-like domain present in CTLA4 is indicated, as are the CH2 and CH3 domains of IgCγ1.

Expression plasmids, CDM8, containing CTLA4Ig were then transfected into COS cells using DEAE/dextran transfection by modification (Linsley et al., 1991, supra) of the protocol described by Seed and Aruffo, 1987, supra.

Expression plasmid constructs (πLN or CDM8) containing cDNA encoding the amino acid sequence of CTLA4Ig, was transfected by lipofection using standard procedures into dhfr⁻ CHO lines to obtain novel cell lines stably expressing CTLA4Ig.

DNA encoding the amino acid sequence corresponding to CTLA4Ig has been deposited with the ATCC under the Budapest Treaty on May 31, 1991, and has been accorded ATCC accession number 68629.

A preferred stable transfectant, expressing CTLA4Ig, designated Chinese Hamster Ovary Cell Line, CTLA4Ig-24, was made by screening B7 positive CHO cell lines for B7 binding activity in the medium using immunostaining. Transfectants were maintained in DMEM supplemented with 10% fetal bovine serum (FBS), 0.2 mM proline and 1 μM methotrexate.

The CTLA4Ig-24 CHO cell line has been deposited with the ATCC under the Budapest Treaty on May 31, 1991 and has been accorded accession number ATCC 10762.

Figure 2:
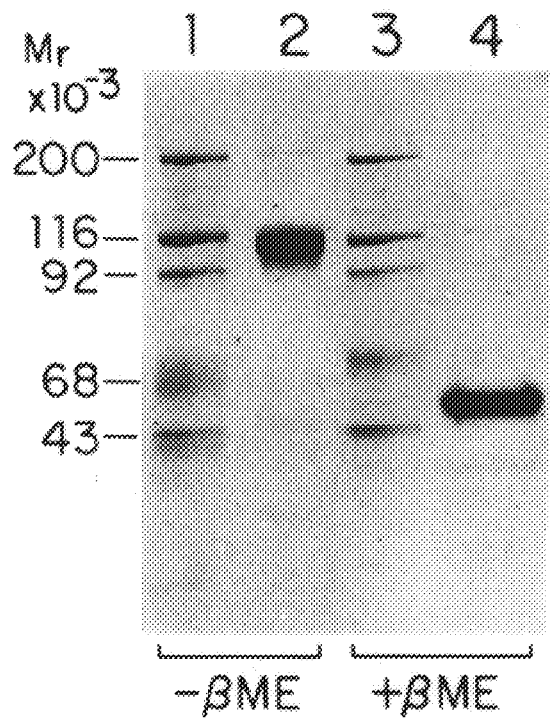
FIG. 2 is a photograph of a gel obtained from SDS-PAGE chromatographic purification of CTLA4Ig as described in Example 2, infra.

CTLA4Ig was purified by protein A chromatography from serum-free conditioned supernatants (FIG. 2). Concentrations of CTLA4Ig were determined assuming an extinction coefficient at 280 nm of 1.6 (experimentally determined by amino acid analysis of a solution of known absorbance). Molecular weight standards (lanes 1 and 3, FIG. 2) and samples (1 μg) of CTLA4Ig (lanes 2 and 4) were subjected to SDS-PAGE (4–12% acrylamide gradient) under non-reducing conditions (–βME, lanes 1 and 2) or reducing conditions (+βME, lanes 3 and 4) Proteins were visualized by staining with Coomassie Brilliant Blue.

Under non-reducing conditions, CTLA4Ig migrated as a $M_r$ approximately 100,000 species, and under reducing conditions, as a $M_r$ approximately 50,000 species (FIG. 2). Because the IgCγ hinge disulfides were eliminated during construction, CTLA4Ig, like CD28Ig, is a dimer presumably joined through a native disulfide linkage.

EXAMPLE 3

CTLA4 Receptor

To reconstruct DNA encoding the amino acid sequence corresponding to the full length human CTLA4 gene, cDNA encoding amino acids corresponding to a fragment of the transmembrane and cytoplasmic domains of CTLA4 was cloned by PCR and then joined with cDNA encoding amino acids corresponding to a fragment from CTLA4Ig that corresponded to the oncostatin M signal peptide fused to the N-terminus of CTLA4. Procedures for PCR, and cell culture and transfections were as described above in Example 1 using COS cells and DEAE-dextran transfection.

Because the expression of CTLA4 receptor protein in human lymphoid cells has not been previously reported, it was necessary to locate a source of CTLA4 mRNA. PCR cDNA reverse transcribed from the total cellular RNA of H38 cells, as noted above, was used for cloning by PCR. For this purpose, the oligonucleotide, GCAATGCACGTGGC-CCAGCCTGCTGTGGTAGTG (SEQ ID NO:11), (encoding the first 11 amino acids in the predicted coding sequence) was used as a forward primer, and TGATGTAA-CATGTCTAGATCAATTGATGG-GAATAAAATAAGGCTG (SEQ ID NO:12) (homologous to the last 8 amino acids in CTLA4 and containing a Xba I site) as reverse primer. The template again was a cDNA synthesized from 1 μg RNA from H38 cells. Products of the PCR reaction were cleaved with the restriction endonucleases Nco I and Xba I and the resulting 316 bp product was gel purified. A 340 bp Hind III/Nco I fragment from the CTLAIg fusion described above was also gel-purified, and both restriction fragments were ligated into Hind III/Xba I cleaved CDM8 to form OMCTLA.

The resulting construct corresponded to full length CTLA4 (SEQ ID NOs: 13 and 14) and the oncostatin M signal peptide. The construct is shown in FIG. 1 and was designated OMCTLA4. The sequence for CTLA4 shown in FIG. 3 differs from the predicted human CTLA4 DNA sequence (Dariavach et al., supra) by a base change such that the previously reported alanine at amino acid position 111 of the amino acid sequence shown, encodes a threonine. This threonine is part of a newly identified N-linked glycosylation site that may be important for successful expression of the fusion protein.

Ligation products were transformed into MC1061/p3 $E.\ coli$ cells and colonies were screened for the appropriate plasmids. Sequences of the resulting constructs were confirmed by DNA sequence analysis.

EXAMPLE 4

Characterization of CTLA4Ig

To characterize the CTLA4Ig constructs, several isolates, CD28Ig, B7Ig, and CD5Ig, were prepared as described above and were transfected into COS cells as described in Examples 2 and 3, and were tested by FACS® analysis for binding of B7Ig. In addition to the above-mentioned constructs, CDM8 plasmids containing cDNAs encoding CD7 as described by Aruffo and Seed, (EMBO Jour. 6:3313–3316 (1987)), incorporated by reference herein, were also used.

mAbs

Murine monoclonal antibodies (mAbs) 9.3 (anti-CD28) and G19-4 (anti-CD3), G3-7 (anti-CD7), BB-1 (anti-B7 antigen) and rat mAb 187.1 (anti-mouse K chain) have been described previously (Ledbetter et al., Proc. Natl. Acad. Sci. 84:1384–1388 (1987); Ledbetter et al., Blood 75:1531 (1990); Yokochi et al., supra) and were purified from ascites before use. The hybridoma producing mAb OKT8 was obtained from the ATCC, Rockville, Md., and the mAb was also purified from ascites before use. mAb 4G9 (anti-CD19) was provided by Dr. E. Engleman, Stanford University, Palo Alto, Calif.). Purified human-mouse chimeric mAb L6 (having human Cγ1 Fc portion) was a gift of Dr. P. Fell and M. Gayle (Bristol-Myers Squibb Pharmaceutical Research Institute, Seattle, Wash.).

Immunostaining and FACS® Analysis

Prior to staining, COS or CHO cells were removed from their culture vessels by incubation in PBS containing 10 mM EDTA. Cells were first incubated with mAbs or Ig fusion proteins at 10 μg/ml in DMEM containing 10% FBS for 1–2 hr at 4° C. Cells were then washed, and incubated for an additional 0.5–2 hrs at 4° C. with FITC-conjugated goat anti-mouse immunoglobulin or with FITC-conjugated goat anti-human Ig C γ serum (both from Tago, Burlingame, Calif.). When binding of both mAbs and Ig fusion proteins were measured in the same experiment, FITC-conjugated anti-mouse and anti-human second step reagents were mixed together before use. Fluorescence on a total of 10,000 cells was then analyzed by FACS®.

Peripheral Blood Lymphocyte Separation and Stimulation

Peripheral blood lymphocytes (PBLs) were isolated by centrifugation through Lymphocyte Separation Medium (Litton Bionetics, Kensington, Md.). Alloreactive T cells were isolated by stimulation of PBL in a primary mixed lymphocyte reaction (MLR) PBL were cultured at $10^6$/ml irradiated (5000 rad) T51 LCL. EBV-transformed lymphoblastoid cell lines (LCL), PM (Bristol-Myers Squibb Co.) and T51 (Bristol-Myers Squibb Co.) were maintained in RPMI supplemented with 10% FBS. After 6 days, alloreactive "blast" cells were cryopreserved. Secondary MLR were conducted by culturing thawed alloreactive blasts together with fresh irradiated T51 LCL in the presence and absence of mAbs and Ig fusion proteins. Cells were cultured in 96 well flat bottom plates ($4\times10^4$ alloreactive blasts and $1\times10^4$ irradiated T51 LCL cells/well, in a volume of 0.2 ml) in RPMI containing 10% FBS. Cellular proliferation of quadruplicate cultures was measured by uptake of [$^3$H]-thymidine during the last 6 hours of a 2–3 day culture.

PHA-activated T cells were prepared by culturing PBLs with 1 μg/ml PHA (Wellcome, Charlotte, N.C.) for five days, and one day in medium lacking PHA. Viable cells were collected by sedimentation through Lymphocyte Separation Medium before use. Cells were stimulated with mAbs or transfected CHO cells for 4–6 hr at 37° C., collected by centrifugation and used to prepare RNA.

CD4$^+$ T cells were isolated from PBLs by separating PBLs from healthy donors into T and non-T cells using sheep erythrocyte rosetting technique and further separating T cells by panning into CD4$^+$ cells as described by Damle et al., J. Immunol. 139:1501 (1987), incorporated by reference herein.

B cells were also purified from peripheral blood by panning as described by Wysocki and Sato, Proc. Natl. Acad. Sci. 75:2844 (1978), incorporated by reference herein, using anti-CD19 mAb 4G9. To measure $T_h$-induced Ig production, $10^6$ CD4$^+$ T cells were mixed with $10^6$ CD19$^+$ B cells in 1 ml of RPMI containing 10% FBS. Following culture for 6 days at 37° C., production of human IgM was measured in the culture supernatants using solid phase ELISA as described by Volkman et al., Proc. Natl. Acad. Sci. USA 78:2528 (1981), incorporated by reference herein.

Briefly, 96-well flat bottom microtiter ELISA plates (Corning, Corning, N.Y.) were coated with 200 μl/well of sodium carbonate buffer (pH 9.6) containing 10 μg/ml of affinity-purified goat anti-human IgG or IgM antibody (Tago, Burlingame, Calif.), incubated overnight at 4° C., and then washed with PBS and wells were further blocked with 2% BSA in PBS (BSA-PBS).

Samples to be assayed were added at appropriate dilution to these wells and incubated with 200 μl/well of 1:1000 dilution of horseradish peroxidase (HRP)-conjugated F(ab')$_2$ fraction of affinity-purified goat anti-human IgG or IgM antibody (Tago). The plates were then washed, and 100 µl/well of o-phenylenediamine (Sigma Chemical Co., St. Louis, Mo.) solution (0.6 mg/ml in citrate-phosphate buffer with pH 5.5 and 0.045% hydrogen peroxide). Color development was stopped with 2N sulfuric acid. Absorbance at 490 nm was measured with an automated ELISA plate reader.

Test and control samples were run in triplicate and the values of absorbance were compared to those obtained with known IgG or IgM standards run simultaneously with the supernatant samples to generate the standard curve using which the concentrations of Ig in the culture supernatant were quantitated. Data are expressed as ng/ml of Ig±SEM of either triplicate or quadruplicate cultures.

Immunoprecipitation Analysis and SDS PAGE

Cells were surface-labeled with $^{125}$I and subjected to immunoprecipitation analysis. Briefly, PHA-activated T cells were surface-labeled with $^{125}$I using lactoperoxidase and H$_2$O$_2$ as described by Vitetta et al., *J. Exp. Med.* 134:242 (1971), incorporated by reference herein. SDS-PAGE chromatography was performed on linear acrylamide gradients gels with stacking gels of 5% acrylamide. Gels were stained with Coomassie Blue, destained, and photographed or dried and exposed to X ray film (Kodak XAR-5).

Binding Assays

B7Ig was labeled with $^{125}$I to a specific activity of approximately $2\times10^6$ cpm/pmole. Ninety-six well plastic dishes were coated for 16–24 hrs with a solution containing CTLA4Ig (0.5 µg in a volume of 0.05 ml of 10 mM Tris, pH 8). Wells were blocked with binding buffer (DMEM containing 50 mM BES (Sigma Chemical Co.), pH 6.8, 0.1 BAS, and 10% FCS) before addition of a solution (0.09 ml) containing $^{125}$I B7Ig (approximately $5\times10^5$ cpm) in the presence or absence of competitor. Following incubation for 2–3 hrs at 23° C., wells were washed once with binding buffer, and four times with PBS. Bound radioactivity was then solubilized by addition of 0.5N NaOH, and quantified by gamma counting.

Binding to B7Ig

Figure 4:
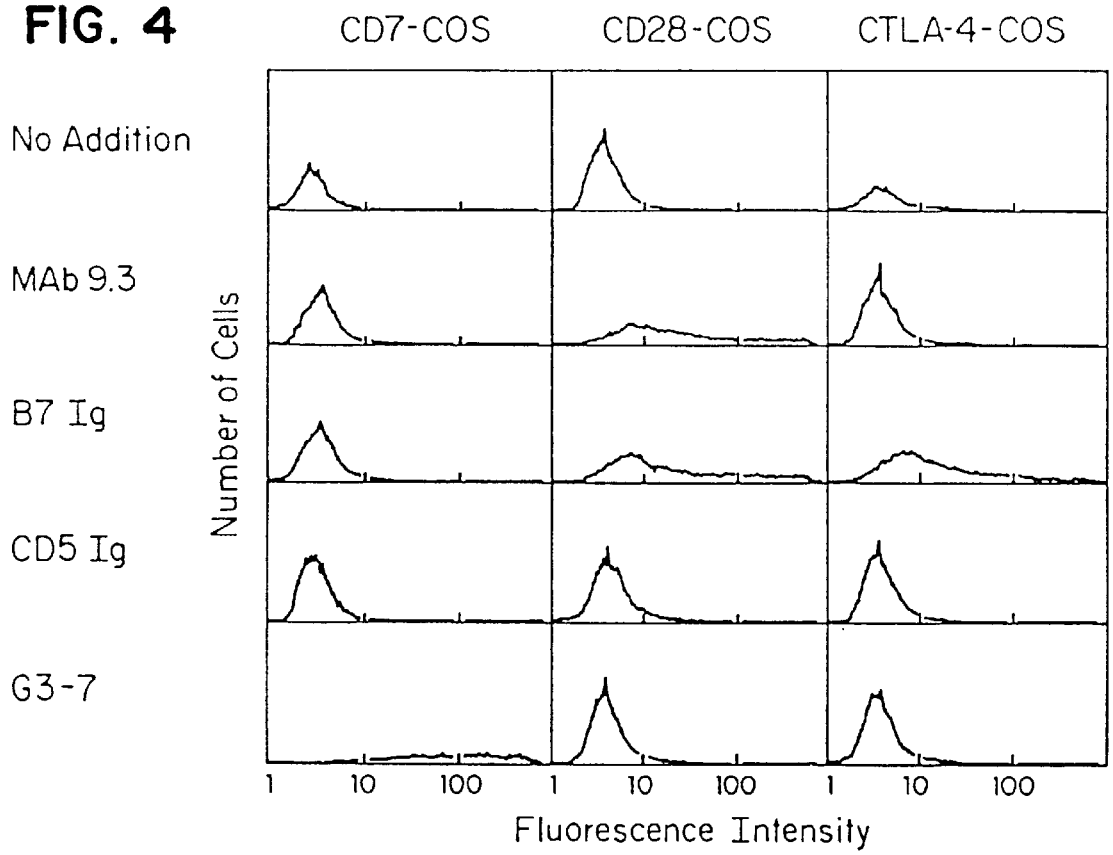
FIG. 4 depicts the results of FACS® analysis of binding of the B7Ig fusion protein to CD28- and CTLA4-transfected COS cells as described in Example 4, infra.

The functional activity of the OMCTLA4 construct encoding the complete human CTLA4 DNA gene, is shown in the experiment shown in FIG. 4. COS cells were transfected with expression plasmids CD7, OMCD28 and OMCTLA4 as described above. Forty-eight hours following transfection, cells were collected and incubated with medium only (no addition) or with mAbs 9.3, B7Ig, CD5Ig or G3-7. Cells were then washed and binding was detected by a mixture of FITC-conjugated goat anti-mouse Ig and FITC-conjugated goat anti-human Ig second step reagents. Transfected cells were tested for expression of the appropriate cell surface markers by indirect immunostaining and fluorescence was measured using FACS® analysis as described above.

As shown in FIG. 4, mAb 9.3 bound to CD28-transfected COS cells, but not to CTLA4-transfected cells. In contrast, the B7Ig fusion protein (but not control CD5Ig fusion protein) bound to both CD28- and CTLA4-transfected cells. CD7-transfected COS cells bound neither mAb 9.3 nor either of the fusion proteins. This indicates that CD28 and CTLA4 both bind the B cell activation antigen, B7. Furthermore, mAb 9.3 did not detectably bind CTLA4.

Binding of CTLA4Ig on B7 Positive CHO cells

Figure 5:
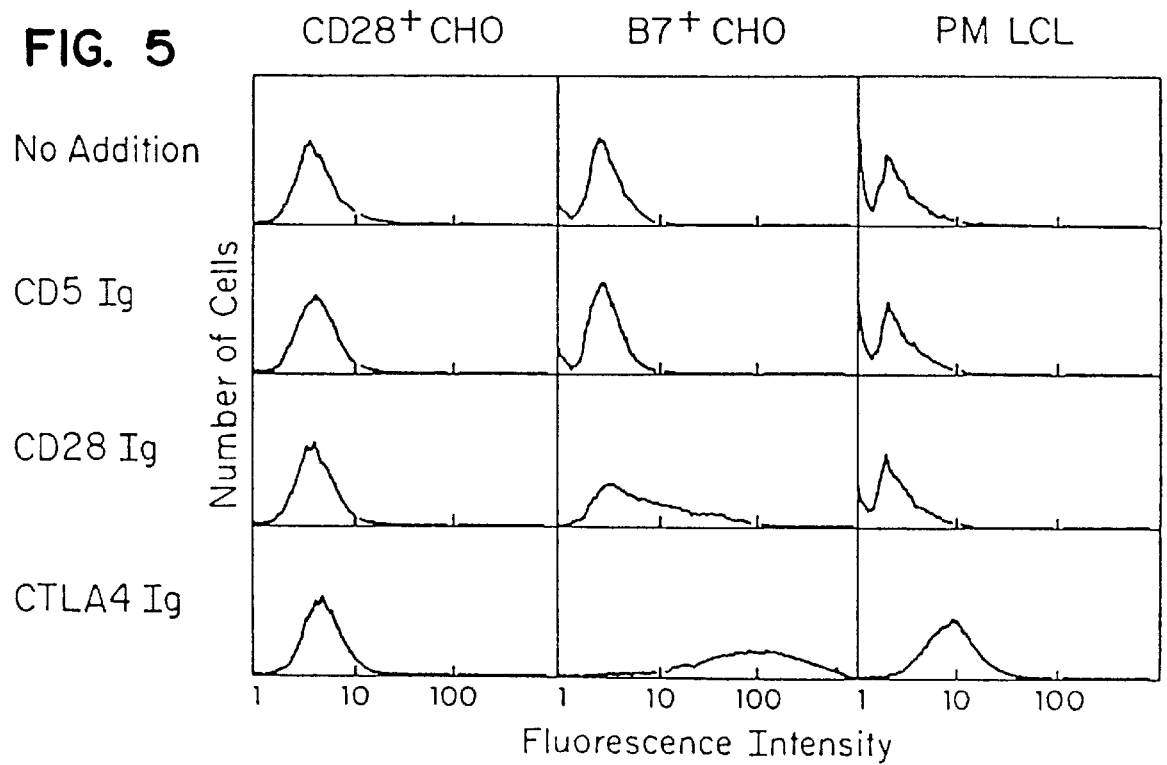
FIG. 5 depicts the results of FACS® analysis of binding of purified CTLA4Ig on B7 antigen-positive (B7$^+$) CHO cells and on a lymphoblastoid cell line (PM LCL) as described in Example 4, infra.

To further characterize the binding of CTLA4Ig and B7, the binding activity of purified CTLA4Ig on B7$^+$ CHO cells and on a lymphoblastoid cell line (PM LCL) was measured in the experiment shown in FIG. 5. Amplified transfected CHO cell lines and PM LCLs were incubated with medium only (no addition) or an equivalent concentration of human Igγ1-containing proteins (10 µg/ml) of CD5Ig, CD28Ig or CTLA4Ig. Binding was detected by FACS® following addition of FITC-conjugated goat anti-human Ig second step reagents. A total of 10,000 stained cells were analyzed by FACS®.

As shown in FIG. 5, CD28Ig bound to B7$^+$ CHO cells but not to PM LCL, a cell line which expresses relatively low levels of the B7 antigen (Linsley et al., supra, 1990). CTLA4Ig bound more strongly to both cell lines than did CD28Ig, suggesting that it bound with higher affinity. Neither CD28Ig nor CTLA4Ig bound to CD28$^+$ CHO cells.

Affinity of Binding of CTLA4Ig and B7Ig

The apparent affinity of interaction between CTLA4Ig and B7Ig was then measured using a solid phase competition binding assay. Ninety-six well plastic dishes were coated with CTLA4Ig as described above. B7Ig was radiolabeled with $^{125}$I ($5\times10^5$ cpm, $2\times10^6$ cpm/pmole), and added to a concentration of 4 nM in the presence of the indicated concentrations (FIG. 6) of unlabeled chimeric mAb L6, mAb 9.3, mAb BB-1 or B7Ig. Plate-bound radioactivity was determined and expressed as a percentage of radioactivity bound to wells treated without competitor (28,300 cpm). Each point represents the mean of duplicate determinations; replicates generally varied from the mean by ≦20%. Concentrations were calculated based on a M$_r$ of 75,000 per binding site for mabs and 51,000 per binding site for B7Ig.

Figure 6:
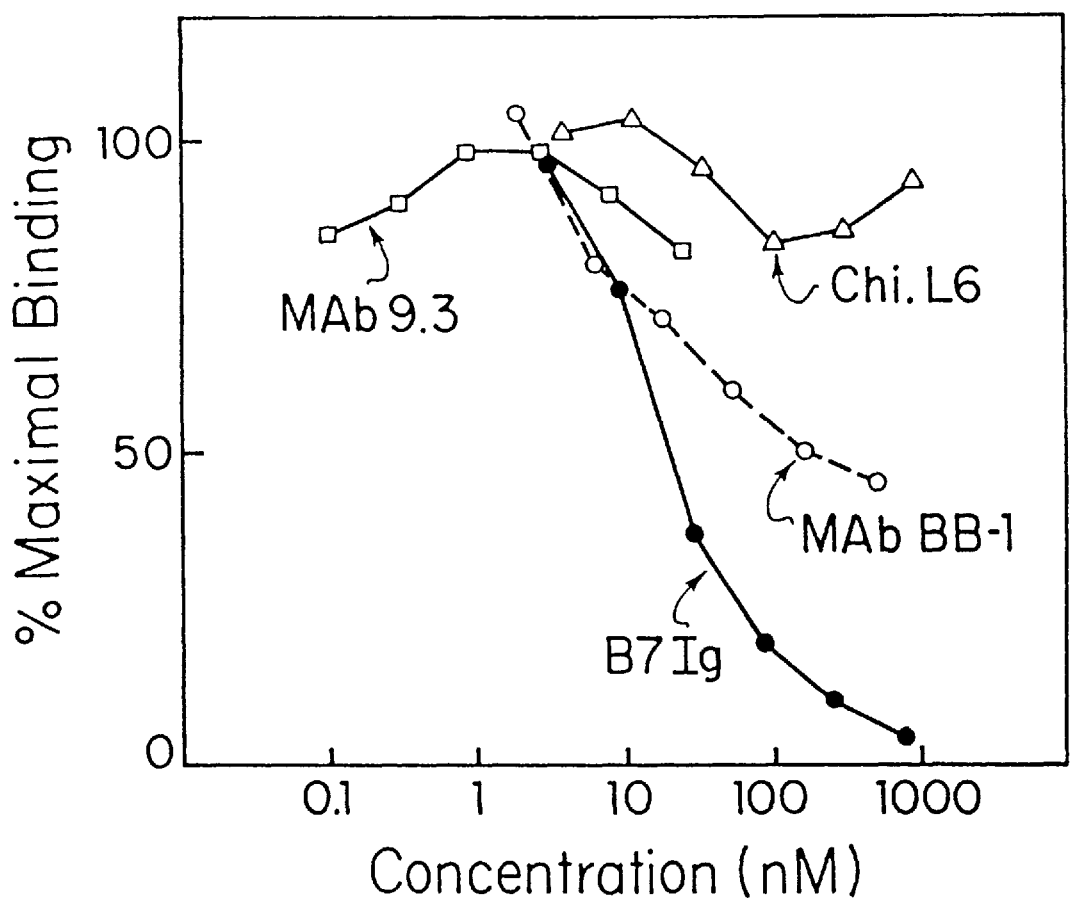
FIG. 6 is a graph illustrating competition binding analysis of $^{125}$I labeled B7Ig to immobilized CTLA4Ig as described in Example 4, infra.

As shown in FIG. 6, only mAb BB-1 and unlabeled B7Ig competed significantly for $^{125}$I-B7Ig binding (half maximal effects at approximately 22 nM and approximately 175 nM, respectively). Neither chimeric mAb L6, nor mAb 9.3 competed effectively at the concentrations tested. In other experiments, the concentrations of mAb 9.3 used were sufficient to inhibit binding of $^{125}$I-B7Ig to immobilized CD28Ig or to cell surface expressed CD28 by ≧90%.

Figure 7:
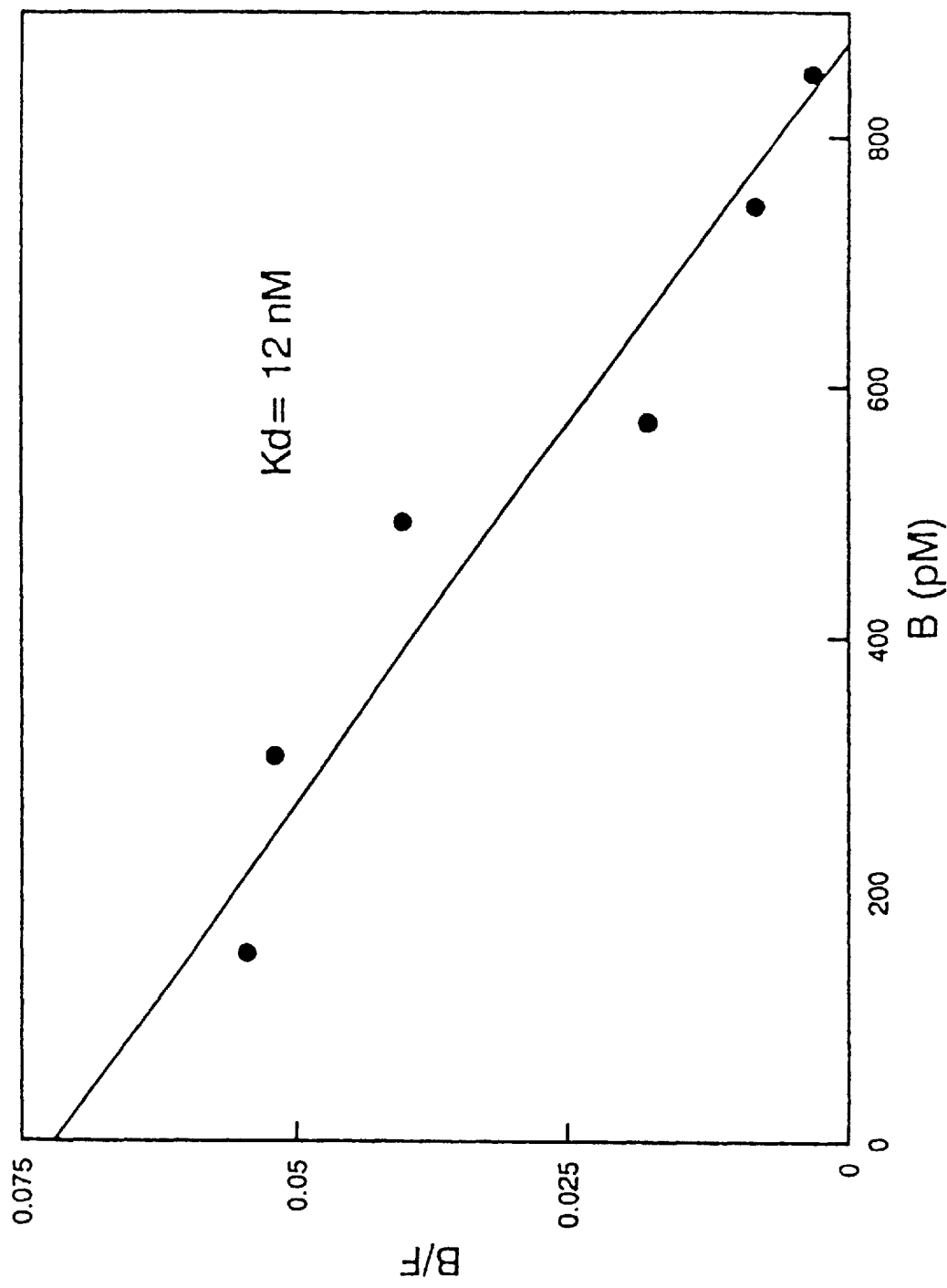
FIG. 7 is a graph showing the results of Scatchard analysis of $^{125}$I-labeled B7Ig binding to immobilized CTLA4Ig as described in Example 4, infra.

When the competition data from FIG. 6 were plotted in a Scatchard representation, a dissociation constant, K$_d$, of approximately 12 nM was calculated for binding of $^{125}$I-B7 to immobilized CTLA4Ig (FIG. 7). This value is approximately 20 fold lower than the previously determined K$_d$ of binding between $^{125}$I-B7Ig and CD28 (approximately 200 nM) (Linsley et al, (1991), supra) indicating that CTLA4 is a higher affinity receptor for the B7 antigen than CD28 receptor.

Figure 8:
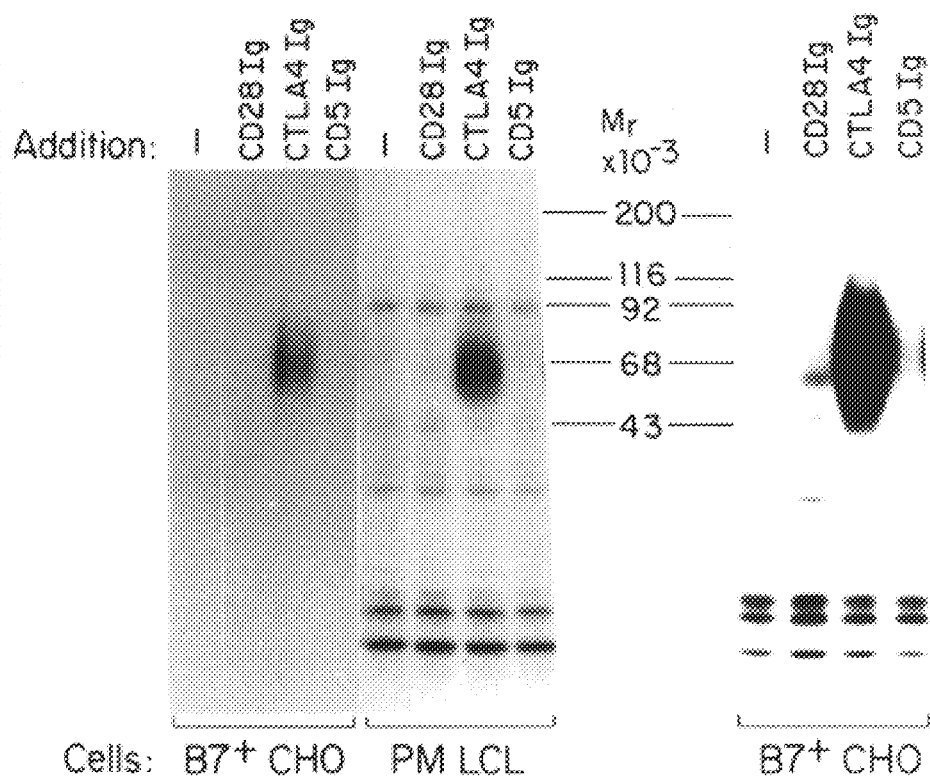
FIG. 8 is a photograph of a gel from SDS-PAGE chromatography of immunoprecipitation analysis of B7 positive CHO cells and PM LCL cells surface-labeled with $^{125}$I as described in Example 4, infra.

To identify the molecule(s) on lymphoblastoid cells which bound CTLA4Ig (FIG. 7), $^{125}$I-surface labeled cells were subjected to immunoprecipitation analysis (FIG. 8). B7$^+$ CHO and PM LCL cells were surface-labeled with $^{125}$I, and extracted with a non-ionic detergent solution as described above. Aliquots of extracts containing approximately 1.5× $10^7$ cpm in a volume of 0.1 ml were subjected to immunoprecipitation analysis as described above with no addition, or 2 µg each of CD28Ig, CTLA4Ig or CD5Ig. Washed immunoprecipitates were then analyzed by SDS-PAGE (10–20% acrylamide gradient) under reducing conditions. The gel was then dried and subjected to autoradiography. The left panel of FIG. 8 shows an autoradiogram obtained after a 1 day exposure. The right panel of FIG. 8 shows an autoradiogram of the same gel after a 10 day exposure. The autoradiogram in the center panel of FIG. 8 was also exposed for 10 days. Positions of molecular weight standard are also indicated in this figure.

As shown by FIG. 8, a diffusely migrating (M$_r$ approximately 50,000–75,000; center at approximately 60,000) radiolabeled protein was immunoprecipitated by CTLA4Ig, but not by CD28Ig or CD5Ig. This molecule co-migrated with B7 immunoprecipitated from B7$^+$ CHO cells by CTLA4Ig, and much more weakly, by CD28Ig. These findings indicate that CTLA4Ig binds a single protein on lymphoblastoid cells which is similar in size to the B7 antigen.

Inhibition of Immune Responses In Vitro by CTLA4Ig

Inhibition of Proliferation

Previous studies have shown that the anti-CD28 mAb, mAb 9.3, and the anti-B7 mAb, mAb BB-1, inhibit proliferation of alloantigen specific $T_h$ cells, as well as immunoglobulin secretion by alloantigen-presenting B Cells (Damle, et al., *Proc. Natl. Acad. Sci.* 78:5096 (1981); Lesslauer et al., *Eur. J. Immunol.* 16:1289 (1986)). Because CTLA4 is a high affinity receptor for the B7 antigen as demonstrated herein, soluble CTLA4Ig was tested for its ability to inhibit these responses. The effects of CTLA4Ig on T cell proliferation were examined in the experiment shown in FIG. 9.

Primary mixed lymphocyte reaction (MLR) blasts were stimulated with irradiated T51 lymphoblastoid cells (LC) in the absence or presence of concentrations of murine mAb 9.3 Fab fragments, or B7Ig, CD28Ig or CTLA4Ig immunoglobulin Cγ fusion proteins.

Figure 9:
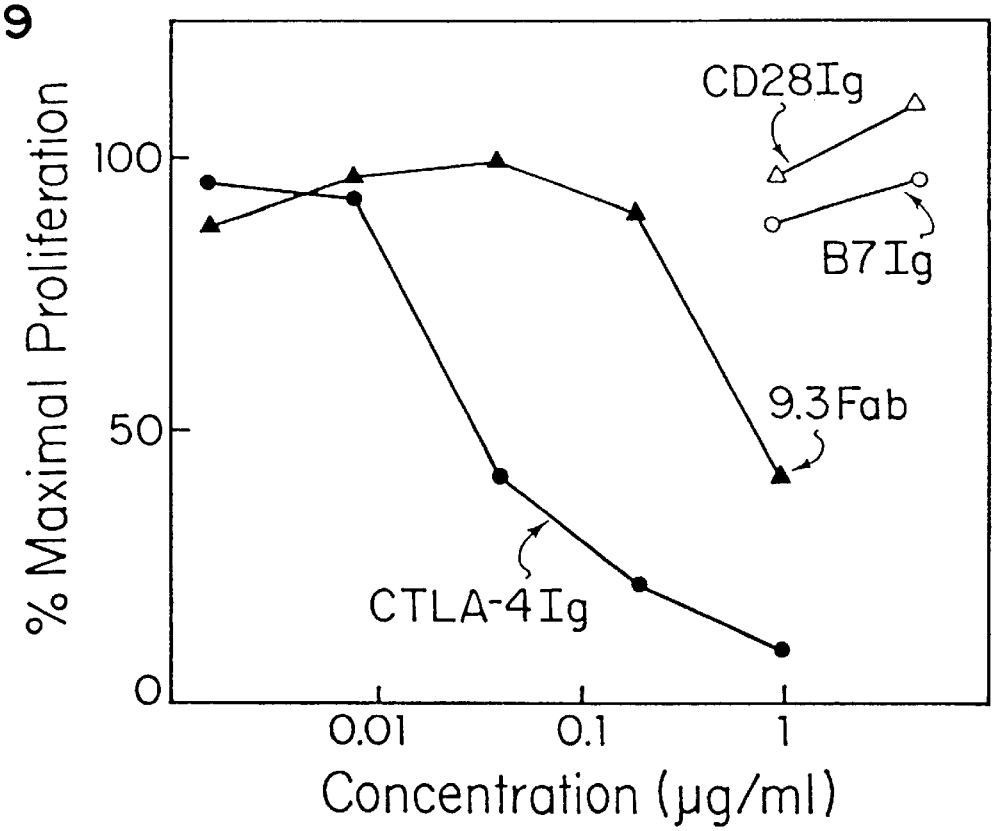
FIG. 9 is a graph depicting the effects on proliferation of T cells of CTLA4Ig as measured by [$^3$H]-thymidine incorporation as described in Example 4, infra.

Cellular proliferation was measured by [$^3$H]-thymidine incorporation after 4 days and is expressed as the percentage of incorporation by untreated cultures (21,000 cpm). FIG. 9 shows the means of quadruplicate determinations (SEM≦10%)

As shown in FIG. 9, CTLA4Ig inhibited the MLR reaction in a dose-dependant fashion by a maximum of >90% with a ½ maximal response at approximately 30 ng/ml (approximately 0.8 nM). The Fab fragment of mAb 9.3, which previously was shown to be a more potent inhibitor of MLR than whole mAb 9.3 (Damle et al., *J. Immunol.* 140:1753–1761 (1988)), also inhibited the MLR, but at higher concentrations (approximately 800 ng/ml or approximately 30 nM for ½ maximal response). B7Ig and CD28Ig did not significantly inhibit the MLR even at higher concentrations. In another experiment, addition of B7Ig together with CTLA4Ig partially overcame the inhibition of MLR by CTLA4Ig, indicating that the inhibition was specifically due to interactions with B7 antigen.

Inhibition of Immunoglobulin Secretion

Figure 10:
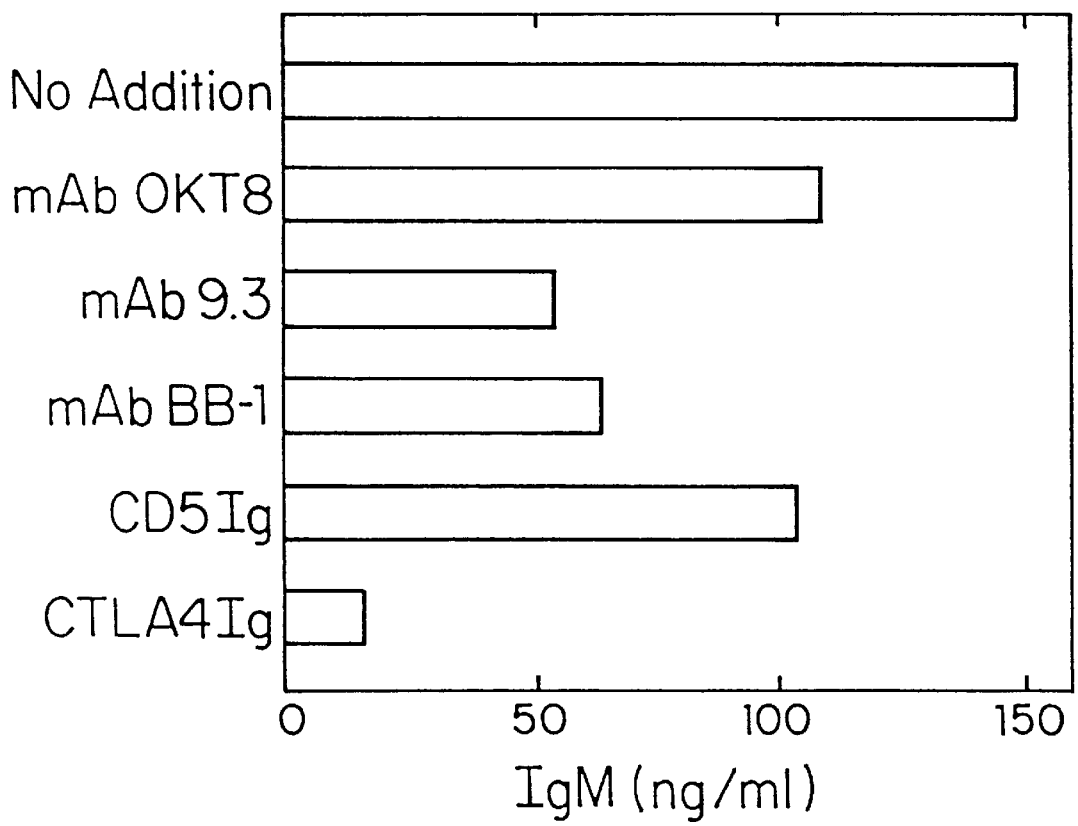
FIG. 10 is a bar graph illustrating the effects of CTLA4Ig on helper T cell (T$_h$)-induced immunoglobulin secretion by human B cells as determined by enzyme immunoassay (ELISA) as described in Example 4, infra.

The effects of CTLA4Ig on helper T cell ($T_h$)-induced immunoglobulin secretion were also examined (FIG. 10). CD4$^+$ T cells were mixed with allogeneic CD19$^+$ B cells in the presence or absence of the indicated immunoglobulin molecules as described above. Murine mAbs OKT8, 9.3 and BB-1 were added at 20 μg/ml, and Ig fusion proteins at 10 μg/ml. After 6 days of culture, concentrations of human IgM (SEM<5%) in culture supernatants were determined by enzyme immunoassay (ELISA) as described above. IgM production by B cells cultured in the absence of CD4$^+$ T cells was 11 ng/ml.

As shown in FIG. 10, CD4$^+$ T cells stimulated IgM production by allogenic CD19$^+$ B Cells (in the absence of CD4$^+$ T cells, IgM levels were reduced by 93%). mAbs 9.3 and BB-1 significantly inhibited $T_h$-induced IgM production (63% and 65% inhibition, respectively). CTLA4Ig was even more effective as an inhibitor (89% inhibition) than were these mAbs. Inhibition by control Ig molecules, mAb OKT8 and CD5Ig, was much less (≦30% inhibition). None of these molecules significantly inhibited Ig production measured in the presence of *Staphylococcal aureus* enterotoxin B. Similar results were obtained with CD4$^+$ T cells and B cells derived from other donors. These results indicate that the inhibition by CTLA4Ig is specific.

The above data also demonstrate that the CTLA4 and CD28 receptors are functionally as well as structurally related. Like CD28, CTLA4 is also a receptor for the B cell activation antigen, B7. CTLA4Ig bound $^{125}$I-B7 with an affinity constant, $K_d$, of approximately 12 nM, a value some 20 fold lower than the affinity between CD28 and B7Ig (approximately 200 nM) indicating higher affinity. Thus, CTLA4 and CD28 may be thought of as high and low affinity receptors, respectively, for the same ligand, the B7 antigen.

The apparent affinity between CD28 and B7 is similar to the affinity reported for binding of soluble alloantigen to the T cell receptor of a murine T cell hybridoma (approximately 100 nM; Schnek et al., *Cell* 56:47 (1989)), and is higher affinity than interactions between CD2 and LFA3 (Recny et al., *J. Biol. Chem.* 265:8542 (1990)), or CD4 and MHC class II molecules (Clayton et al., *Nature* 339:548 (1989)). The apparent affinity constant, $K_d$, between CTLA4 and B7 is even greater, and compares favorably with higher affinity mAbs ($K_d$ 2–10,000 nM; Alzari et al., *Ann. Rev. Immuno.* 6:555 (1988)). The $K_d$ between CTLA4 and B7 is similar to or greater than $K_d$ values of integrin receptors and their ligands (10–2000 nM; Hautanen et al., *J. Biol. Chem.* 264:1437–1442 (1989); Di Minno et al., *Blood* 61:140–148 (1983); Thiagarajan and Kelley, *J. Biol. Chem.* 263:035–3038 (1988)). The affinity of interaction between CTLA4 and B7 is thus among the highest yet reported for lymphoid adhesion systems.

These results demonstrate the first expression of a functional protein product of CTLA4 transcripts. CTLA4Ig, a fusion construct containing the extracellular domain of CTLA4 fused to an IgCγ1 domain, forms a disulfide-linked dimer of $M_r$ approximately 50,000 subunits (FIG. 1). Because no interchain disulfides would be predicted to form in the Ig portion of this fusion, it seems likely that cysteines from CTLA4 are involved in disulfide bond formation. The analogous CD28Ig fusion protein (Linsley et al, supra, 1991) also contains interchain disulfide linkage(s). These results suggest that CTLA4 receptor, like CD28 (Hansen et al., *Immunogenetics* 10:247–260 (1980)), exists on the T cell surface as a disulfide linked homodimer. Although CD28 and CTLA4 are highly homologous proteins, they are immunologically distinct, because the anti-CD28 mAb, mAb 9.3, does not recognize CTLA4 (FIGS. 4 and 5).

It is not known whether CTLA4 can activate T cells by a signalling pathway analogous to CD28. The cytoplasmic domains of murine and human CTLA4 are identical (Dariavach et al., supra 1988), suggesting that this region has important functional properties. The cytoplasmic domains of CD28 and CTLA4 also share homology, although it is unclear if this is sufficient to impart similar signaling properties to the two molecules.

CTLA4Ig is a potent inhibitor of in vitro lymphocyte functions requiring T cell and B cell collaboration (FIGS. 9 and 10). These findings, together with previous studies, indicate the fundamental importance of interactions between B7 antigen and its counter-receptors, CD28 and/or CTLA4, in regulating both T and B lymphocyte responses. CTLA4Ig should be a useful reagent for future investigations on the role of these interactions during immune responses. CTLA4Ig is a more potent inhibitor of in vitro lymphocyte responses than either mAb BB-1 or mAb 9.3 (FIGS. 9 and 10). The greater potency of CTLA4Ig over mAb BB-1 is most likely due to the difference in affinities for B7 between these molecules (FIG. 6). CTLA4Ig is also more potent than mAb 9.3, probably because, unlike the mAb, it does not also have direct stimulatory effects on T cell proliferation (June et al., *Immunology Today* 11:211 (1989)) to counteract its inhibitory effects. The immunosuppressive effects of CTLA4Ig in vitro suggest that future investigations are warranted into possible therapeutic effects of this molecule for treatment of autoimmune disorders involving aberrant T cell activation or Ig production.

EXAMPLE 5

Female BALB/c (H-$2^d$) and C57BL/6 (H-$2^d$)mice, 6 to 8 wk. of age were obtained from The Jackson Laboratory (Bar Harbor, Me.).

Human pancreatic islets cells were purified after collagenase digestion as described (C. Ricordi et al. Transplantation 52:519 (1991); A. G. Tzakis et al. Lancet 336:402 (1990); C. Ricordi, P. E. Lacy, E. H. Finke, B. J. Olack, D. W. Scharp, Diabetes 37:413 (1988)).

B6 or B10 mice, treated with streptozotocin (175 mg per kilogram of body weight) 3 to 5 days before transplant and exhibiting nonfasting plasma glucose levels of greater than 280 mg/dl (with the majority over 300 mg/ml), were used as recipients.

Each animal received approximately 800 fresh human islets of 150 µm in diameter beneath the left renal capsule (D. Faustman and C. Coe, Science 252:1700 (1991); Y. J. Zeng et al. Transplantation 53:277 (1992)). Treatment was started immediately after transplantation.

Control animals were treated with PBS (solid lines) or L6 (dotted lines) at 50 µg every other day for 14 days immediately after transplantation (FIG. 11A). Islet transplants were considered rejected when glucose levels were greater than 250 mg/dl for three consecutive days. Animals treated with PBS (n=14) and L6 (n=8) had mean graft survivals of 5.6 and 6.4 days, respectively.

Animals were treated with 10 µg of CTLA4Ig for 14 consecutive days immediately after transplant (n=7) (FIG. 11B). Three out of seven animals maintained their grafts for >80 days. The remaining four animals had a mean graft survival of 12.75 days.

Animals were treated with 50 µg of CTLA4Ig every other day for 14 days immediately after human islet transplantation (FIG. 11C). All animals (n=12) treated with this dose maintained grafts throughout the analysis (FIG. 11C). Selected mice were nephrectomized on days 21 and 29 after the transplant to assess the graft's function (FIG. 11C).

Histology was performed on kidneys transplanted with human islet cells (FIGS. 12A, 12B, 12C, and 12D). The slides were analyzed blindly.

Figure 12A:
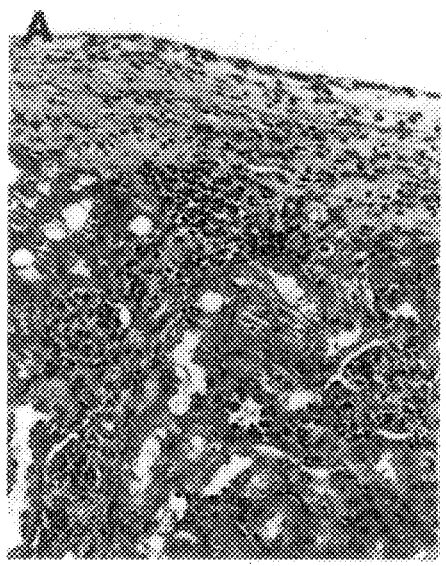
FIGS. 12A, 12B, 12C, and 12D are photographs of histopathology slides of human islets transplanted under the kidney capsule of B10 mice.
Figure 12B:

Hematoxylin and eosin staining of a control human islet grafted mouse 29 days after transplantation showed a massive lymphocyte infiltration (FIG. 12A). The same tissue, stained for insulin, showed no detectable insulin production (FIG. 12B).

Figure 12C:
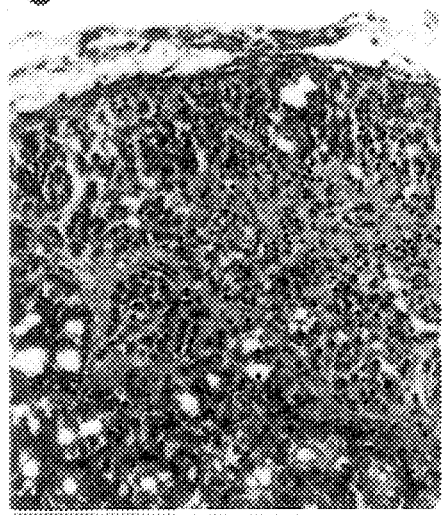
Figure 12D:

Histological examination of tissue from a CTLA4Ig-treated mouse 21 days after transplant showed intact islets under the kidney capsule with very few lymphocytes infiltrating the transplanted tissue (FIG. 12C). The tissue was stained with hematoxylin and eosin. The same tissue from the CTLA4Ig-treated mouse, stained for insulin, showed the production of insulin by the grafted islets (FIG. 12D). Similar results were observed in graft tissue examined at later time points. The upper, middle, and lower arrowheads identify the kidney capsule, islet transplant, and kidney parenchyma, respectively.

In the histopathology assay all tissues were fixed in 10% buffered formalin and processed, and 5-µm sections were stained either with hematoxylin and eosin or for insulin with the avidin-biotin-peroxidase method (S. M. Hsu, L. Raine, H. Fanger, J. Histochem, Cytochem, 29:577 (1981)). Magnification was ×122.

Figure 13:
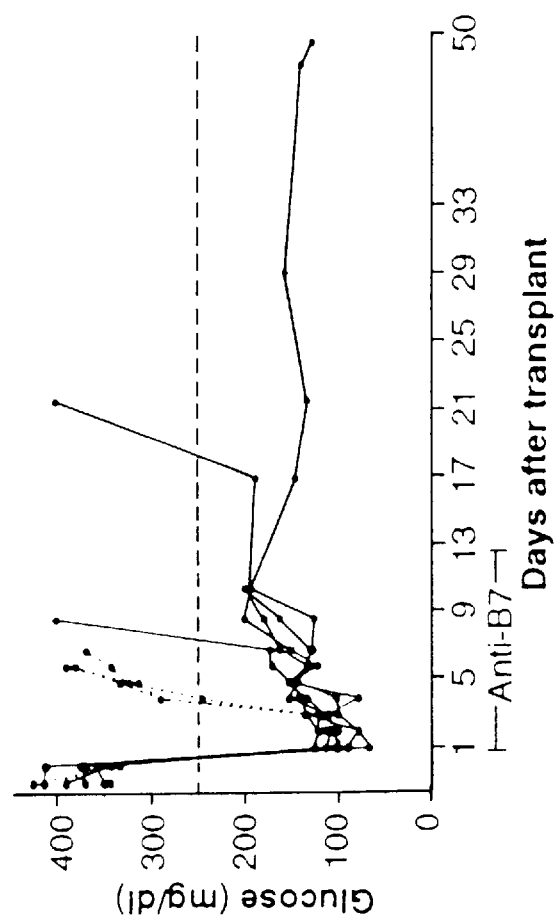
FIG. 13 is a line graph showing the prolongation of islet graft survival with MAb to human B7.

In FIG. 13 streptozotocin-treated animals were transplanted as described hereinabove for FIG. 11. The mice were treated either with PBS (dotted lines) or with MAb to human B7 (solid lines) at a dose of 50 µg every other day for 14 days (FIG. 13). Control animals (treated with PBS) (n=3) had a mean graft survival of 3.5 days, whereas anti-B7-treated animals (n=5) maintained grafts from 9 to >50 days (FIG. 13).

Figure 14:
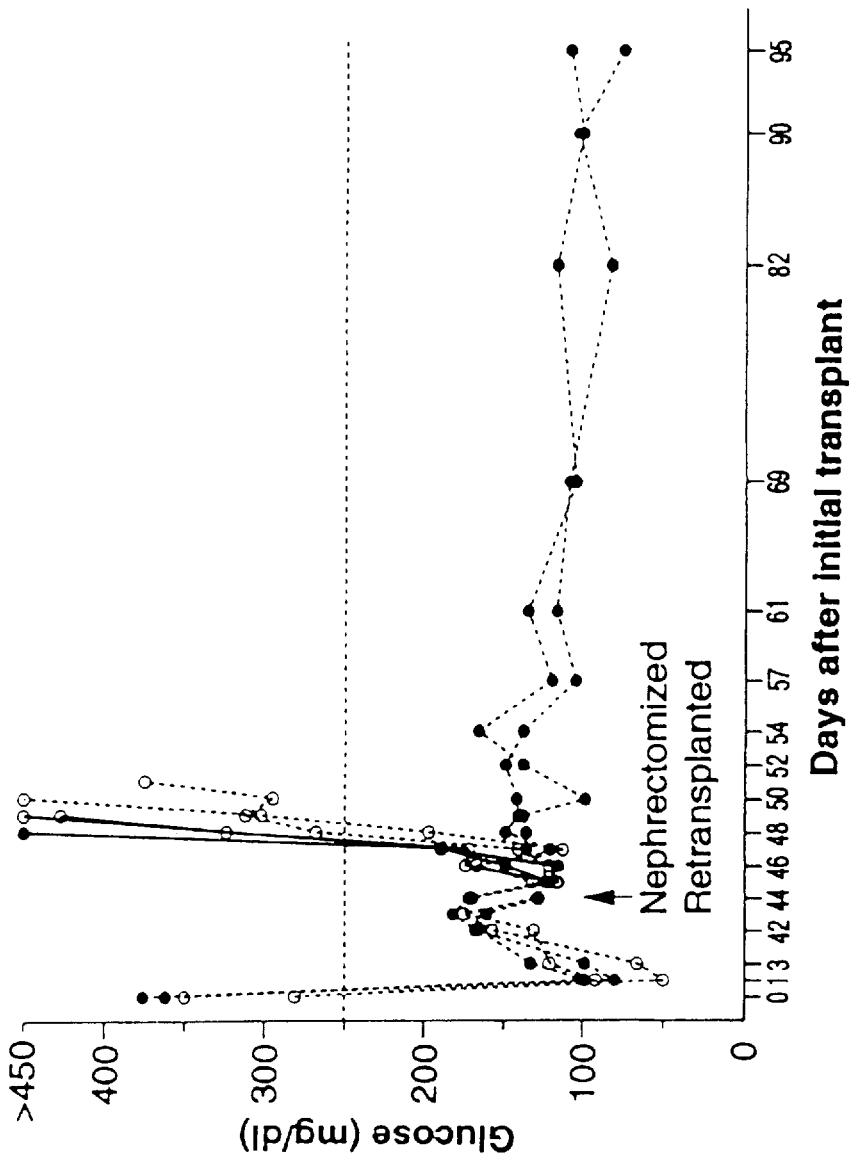
FIG. 14 is a line graph showing induction of donor-specific unresponsiveness to islet graft antigens by CTLA4Ig.
Figure 16:
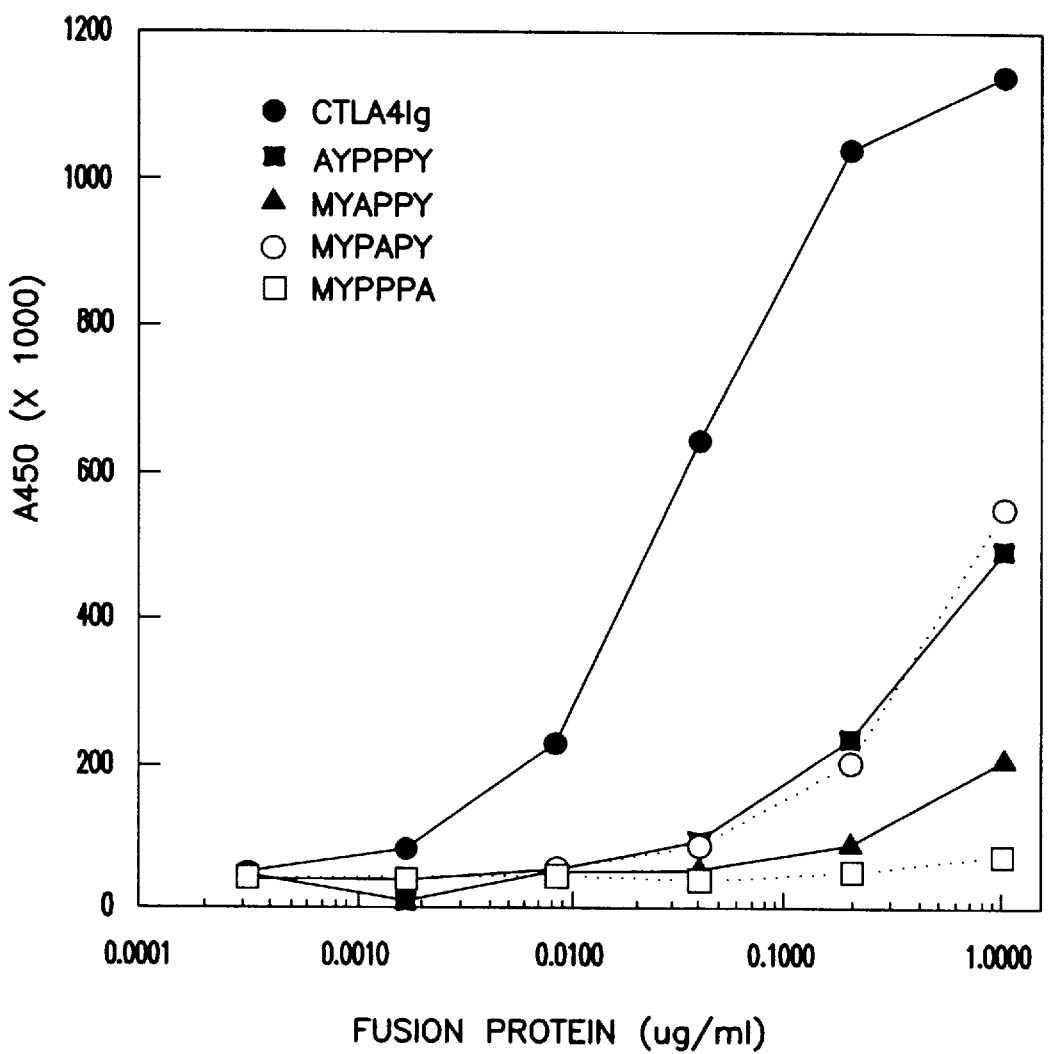
FIG. 16 is a line graph showing CTLA4Ig and CD28Ig mutants bind B7-1.

In FIG. 14 normal glycemic, CTLA4Ig-treated, transplanted mice (dotted lines) were nephrectomized on day 44 after transplant and immediately retransplafirst party ther 1000 first party donor islets (dotted lines, solid circles) or 1000 second party islets (dotted lines, open circles) beneath the remaining kidney capsule.

These islets, frozen at the time of the first transplant, were thawed and cultured for 3 days before transplant to ensure islet function. B10 mice that had been treated with streptozotocin and exhibited nonfasting glucose levels of greater than 280 mg/dl were used as controls (solid lines) (FIG. 14). No treatment was given after transplantation.

Control animals rejected both the first party (solid lines, closed circles) and the second party (solid lines, open circles) islet grafts by day 4 after transplant (FIG. 14). The CTLA4Ig-treated mice retransplanted with second party islets had a mean graft survival of 4.5 days, whereas animals retransplanted with first party donor islets maintained grafts for as long as analyzed (>80 days) (FIG. 14).

CTLA4Ig significantly prolongs human islet graft survival in mice in a donor-specific manner thereby providing an approach to immunosuppression C57BL/6 (B6) or C57BL/10 (B10) mice were treated with streptozotocin to eliminate mouse pancreatic islet B cell function. Diabetic animals were grafted under the kidney capsule, and treatment was started immediately after surgery. Survival of the islet grafts was monitored by the analysis of blood glucose concentrations.

Transplanted control animals, treated with either phosphate-buffered saline (PBS) (n=14) or L6 (a human IgG1 chimeric MAb; n=8), had a mean graft survival of 5.6 and 6.4 days, respectively (FIG. 11A).

In contrast, islet rejection was delayed in animals treated with CTLA4Ig (10 µg per day for 14 days), with four out of the seven animals exhibiting moderately prolonged mean graft survival (12.75 days), whereas the remaining three animals maintained normal glucose levels for >80 days (FIG. 11B). This eventual increase in glucose concentration may be a result of islet exhaustion because no evidence of active cellular rejection was observed.

In the three mice that maintained long-term islet grafts, the transient increase in glucose concentrations around day 21 after the transplant may have represented a self-limited rejection episode consistent with the pharmacokinetics of CTLA4Ig clearance after therapy (P. S. Linsley et al., Science 257:792 (1992)).

In subsequent experiments, the dose of CTLA4Ig was increased to 50 µg per animal every other day for about 14 days. This treatment resulted in 100% of the animals maintaining normal islet function throughout the experiment with no signs of a rejection crisis (FIG. 11C).

In order to confirm that insulin production originated from the transplanted islets and not from the native mouse pancreas, we nephrectomized selected animals at days 21 and 29 to remove the islet grafts (FIG. 11C). In these animals, glucose concentrations increased to above 350 mg/dl within 24 hours, which indicated that the islet xenograft was responsible for maintaining normal glucose levels. It appears that the blocking of the CD28-B7 interaction inhibits xenogenic islet graft rejection.

The effects of treatment with the soluble receptor, namely CTLAIg fusion protein, were not a result of Fc binding (L6 did not effect graft rejection) or general effects on T cell or B cell function in vivo.

Historical analyses of islet xenograft from control (PBS treated) and CTLA4Ig treated mice were done (FIGS. 12A, 12B, 12C, 12D). The islet tissue from the control animal demonstrated evidence of immune rejection, with a marked lymphocytic infiltrate into the graft and few remaining islets (FIG. 12A).

Immunohistochemical staining showed that insulin-positive cells were present only rarely, and no somatostatin-positive cells were present at all (FIG. 12B). In contrast, transplant tissue from the CTLA4Ig-treated mice was devoid of any lymphocytic infiltrate (FIG. 12C).

The grafts were intact, with many islets visible. In addition, the B cells observed in the human islet tissue produced human insulin (FIG. 12D) and somatostatin.

The human CTLA4Ig used in this study reacts with both murine is and human B7. One advantage of the xenogeneic transplant model is the availability of a MAb to human B7 that does not react with mouse B7 (T. Yokochi, R. D. Holly, E. A. Clark, J. Immunol. 128:823 (1982)). Thus, the role of human B7-bearing antigen-presenting cells (APCs) could be directly examined.

The mice were transplanted as described and then treated with 50 μg of MAb to human B7 every other day for 14 days after transplant. This treatment prolonged graft survival in treated mice (9 to >50 days) in comparison to that for control mice (FIG. 13). The anti-B7 MAb is unable to block rejection as effectively as CTLA4Ig.

The CTLA4Ig therapy resulted in graft acceptance in the majority of mice. However, the animals may not be tolerant. Transient immunosuppression can lead to permanent islet graft acceptance because of graft adaptation (the loss of immunogenicity as a result of the loss of APC function) (L. Hao, Y. Wang, R. G. Gill, K. J. Lafferty, J. Immunol. 139:4022 (1987); K. J. Lafferty, S. J. Prowse, M. Simeonovic, Annu. Rev. Immunol. 1:143 (1983)).

In order to differentiate between these possibilities, we nephrectomized selected xenografted, CTLA4Ig-treated mice (day 40) and retransplanted them under the remaining kidney capsule with either the original donor islets (first party) or unrelated second party human islets (FIG. 14).

Streptozotocin-treated control animals, having never received an islet graft, were also transplanted with either first or second party islets. No treatment after the transplant was given. Control animals rejected the first and second party islets by day 4. The CTLA4Ig-treated animals that had received the second party islets rejected these islets by day 5, whereas animals receiving first party donor islets maintained the grafts for >80 days (FIG. 14).

These results suggest that the CTLA4Ig treatment resulted in prolonged donor-specific unresponsiveness to the xenogeneic islets. The ability of the murine immune response to distinguish differences among the human islet donors also supports the direct recognition of the polymorphic MHC products expressed on the human islet cells.

EXAMPLE 6

By site-specific and homolog mutagenesis, we have identified regions in CTLA4Ig which are required for its high avidity binding to B7-1. The following is a description of how to make soluble CTLA4/CD28 hybrid fusion proteins which bind B7.

MATERIALS AND METHODS

Monoclonal antibodies (mabs). Murine mAb's specific for CTLA4 were prepared and characterized as previously described (Linsley et al. J. Ex. Med., (1992) 176:1595–1604). Antibody 9.3 (anti-CD28) has been described previously ((Hansen et al., *Immunogenetics* 10:247–260 (1980)).

Cell Culture. The preparation of stably transfected B7-1 positive CHO cells has been previously described (Linsley et al., in *J. Exp. Med.* 173:721–730 (1991); P. S. Linsley et al., J. Exp. Med. 174:561 (1991)).

Cells were maintained in DMEM supplemented with 10% fetal bovine serum (FBS), 0.2 mM proline, and 1 μM methotrexate. Cos cells were grown in DMEM supplemented with 10% FBS. CTLA4Ig was prepared in CHO cells as previously described (Example 2).

CTLA4Ig and CD28Ig site-directed mutant expression plasmids. Site-directed mutagenesis was performed on a vector encoding soluble chimeric form of CTLA4 (CTLA4Ig) in which the extracellular domain of CTLA4 was genetically fused to the hinge and constant regions of a human IgG heavy chain (Example 2). CTLA4Ig site-directed mutants were prepared by encoding the desired mutation in overlapping oligonucleotide primers and generating the mutants by PCR (Ho et al., 1989, supra) using the CTLA4Ig plasmid construct as a template.

Six mutants were prepared which encoded substitutions to alanine in the highly conserved hexapeptide 98MYPPPY103 forming part of the putative CDR3-like domain (FIGS. 15 and 19) (Ho et al., 1989, supra). These mutants are described in Table II.

In addition, two mutants encoding the residues P103A and Y104A (MYPPAY and MYPPPA, respectively) from the CD28Ig 99MYPPPY104 hexapeptide using CD28Ig as a template were also prepared by the same method. These mutants are also described in Table II.

Primers required for PCR reactions but not for introducing mutations included (1) a CDM8 forward (CDM8FP) primer encoding a complementary sequence upstream of the HindIII restriction site at the 5' end of the CDM8 stuffer region, and (2) a reverse primer (CDM8RP) encoding a complementary sequence downstream of the XbaI site at the 3' end of the CDM8 stuffer region.

These primers encoded the following sequences:

CDM8FP:5'-AATACGACTCACTATAGG (SEQ ID NO:15)

CDM8RP:5'-CACCACACTGTATTAACC (SEQ ID NO:16)

PCR conditions consisted of 6 min at 94° C. followed by 25 cycles of 1 min at 94° C., 2 min at 55° C. and 3 min at 72° C. Taq polymerase and reaction conditions were used as suggested by the vendor (Perkin Elmer Cetus, Emeryville, Calif.). PCR products were digested with HindIII and XbaI and ligated to HindIII/XbaI-cut CDM8 expression vector.

Plasmids were transfected into COS cells (Aruffo et al., *Cell* 61:1303 (1990)) and the conditioned media was used as a source for the resulting Ig mutant fusion proteins.

CTLA4/CD28Ig hybrid expression plasmids. CTLA4/CD28Ig hybrid scan plasmids encoding the constructs HS2, HS4, HS4-A, HS4-B, and HS5 (FIG. 17 and Table I) were prepared by PCR using overlapping oligonucleotide primers designed to introduce CTLA4 sequences into CD28Ig while, at the same time, deleting the equivalent region from CD28. The same CDM8 forward and reverse PCR primers described above were also used.

The following is a list of the CTLA4/CD28 hybrid fusion proteins which were made.

| DESIGNATION | FRAMEWORK | MODIFICATIONS |
|---|---|---|
| HS1 | CTLA4 | 1–24 OF CD28 |
|  |  | 97–125 OF CD28 |
| HS2 | CD28 | 1–22 OF CTLA4 |
|  |  | 96–125 OF CTLA4 |
| HS3 | CTLA4 | 96–125 OF CD28 |
| HS4 | CD28 | 96–123 OF CTLA4 |
| HS4A | CD28 | 96–113 OF CTLA4 |
| HS4B | CD28 | 114–123 OF CTLA4 |
| HS5 | CD28 | 25–32 OF CTLA4 |
| HS6 | CTLA4 | 25–32 OF CD28 |
| HS7 | CD28 | 96–123 OF CTLA4 |
|  |  | 25–32 OF CTLA4 |
| HS8 | CD28 | 25–32 OF CTLA4 |
|  |  | 96–113 OF CTLA4 |
| HS9 | CD28 | 25–32 OF CTLA4 |
|  |  | 114–123 OF CTLA4 |
| HS10 | CD28 | 96–123 OF CTLA4 |
|  |  | 51–58 OF CTLA4 |
| HS11 | CD28 | 25–32 OF CTLA4 |
|  |  | 51–58 OF CTLA4 |
|  |  | 96–123 OF CTLA4 |
| HS12 | CD28 | 51–58 OF CTLA4 |
|  |  | 96–113 OF CTLA4 |
| HS13 | CD28 | 25–32 OF CTLA4 |
|  |  | 51–58 OF CTLA4 |
|  |  | 96–113 OF CTLA4 |
| HS14 | CD28 | 51–58 OF CTLA4 |

Each cDNA construct was genetically linked to cDNA encoding the hinge and constant regions of a human IgG1 in order to make soluble chimeras.

A HS6 hybrid was prepared in a similar manner to that described above except that the CDR1-like region in CTLA4Ig was replaced with the equivalent region from CD28Ig.

HS7, HS8, and HS9 constructs were prepared by replacing a ≈350 base-pair HindIII/HpaI 5' fragment of HS4, HS4-A, and HS4-B, respectively, with the equivalent cDNA fragment similarly digested from HS5 thus introducing the CDR1-like loop of CTLA4 into those hybrids already containing the CTLA4 CDR3-like region.

HS10–HS13 constructs are domain homolog mutants which were prepared by introducing the CDR2-like loop of CTLA4Ig into previously constructed homolog mutants. This was done by overlapping PCR mutagenesis whereby primers were designed to introduce CTLA4 CDR2-like sequences into homolog templates while at the same time deleting the equivalent CD28 CDR2-like region from the molecule.

Figure 17:
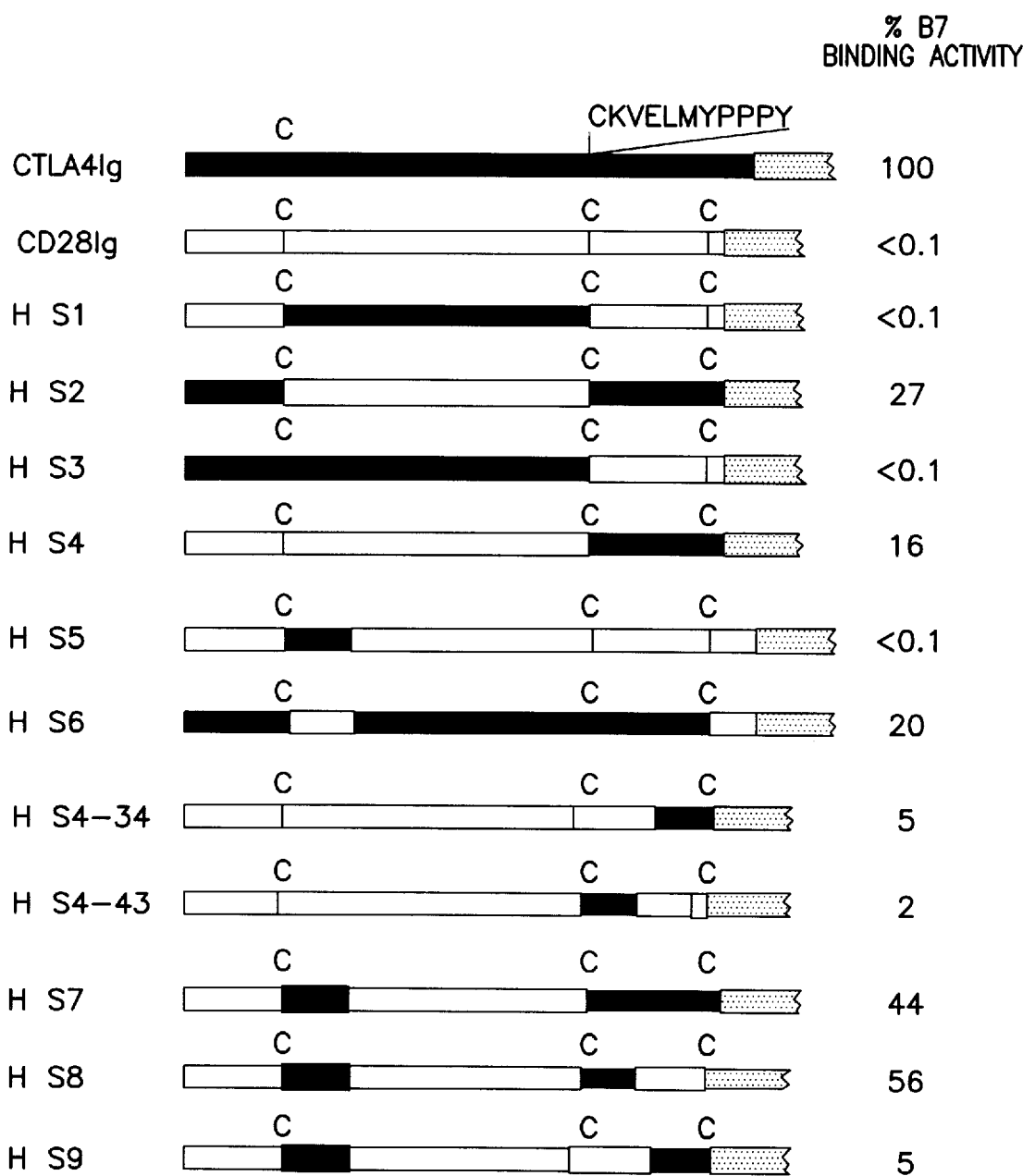
FIG. 17 is a schematic map of CTLA4/CD28Ig hybrid fusion proteins. Open areas represent CD28 sequence; filled areas represent CTLA4 sequence; cross-hatched areas represent beginning of IgG Fc (also refer to Table I).

Accordingly, HS4 served as a template to make HS10; HS7 served as a template to make HS11; HS4-A served as a template to make HS12; and HS8 served as a template to make HS13 (FIG. 17 and Table I). The CDM8 primers described above were also used in these constructions.

The HS14 hybrid construct was prepared by replacing the CDR2-like loop of CD28 with the equivalent loop from CTLA4Ig (FIG. 17 and Table I).

Oligonucleotide primers designed to introduce these changes were used in overlapping PCR mutagenesis identical to that described for other mutants.

PCR reactions and subcloning into CDM8 were performed as described above. Again all mutants were sequenced by the dideoxy chain termination/extension reaction.

Plasmids encoding each of the mutants were transfected into COS cells and the resulting soluble Ig fusion proteins were quantitated in culture media and visualized by Western blot as described in following sections.

Quantitation of the resulting Ig fusion proteins in culture media. Soluble mutant fusion proteins were quantitated in an enzyme immunoassay by determining the amount of Ig present in serum-free COS cell culture media.

Microtiter plates (Immulon2; Dynatech Labs., Chantilly, Va.) were coated with 0.5µg/ml goat anti-human IgG (Jackson Immunoresearch Labs., West Chester, Pa.) for 16–24 h at 4° C. Wells were blocked for 1 h with specimen diluent (Genetic Systems, Seattle, Wash.), then washed with PBS containing 0.05% Tween 20 (PBS-Tw).

COS cell culture media containing fusion proteins was added at various dilutions and incubated for 1 h at 22° C. Known concentrations of CTLA4Ig were also added to separate wells on each plate for a standard curve.

After washing, horseradish peroxidase (HRP)-conjugated goat anti-human IgG (Tago, Burlingame, Calif.) diluted 1:12,000 was added and incubated for 1 h at 22° C. Wells were then washed and incubated with 3,3',5,5' tetramethyl-benzidine (TMB) substrate (Genetic Systems) for 15 min before stopping the reaction by the addition of 1N $H_2SO_4$. Optical density was measured at dual wavelengths of 450 and 630 nm on a microtiter plate reader (Genetic Systems).

Concentration of mutant Ig fusion protein was determined by comparison with a standard curve of known concentrations of CTLA4 Ig.

Immunoprecipitation and Western blot analysis. CTLA4/CD28Ig hybrid fusion proteins present in culture media were adsorbed to protein A-Sepharose by overnight incubation at 4° C. The beads were washed with PBS containing 0.1 Nonidet-P40 (NP40) then SDS PAGE sample buffer was added and the eluted protein was loaded onto an SDS polyacrylamide gel.

Western blot transfer of protein onto nitrocellulose was done by standard procedures. Nitrocellulose membranes were then blocked with PBS containing 0.1% NP40 and 1% non-fat dry milk powder.

After washing in PBS-Tw membranes were incubated with alkaline phosphatase-conjugated goat anti-human IgG (Boehringer Mannheim, Indianapolis, Ind.) diluted 1:1,000 and incubated for 1 h at 22° C. Blots were then washed and developed using standard procedures.

B7 positive CHO cell enzyme immunoassay. The ability of CTLA4Ig mutant fusion proteins, and CTLA4/CD28Ig hybrid fusion proteins to bind B7-1 stably expressed on CHO cells was determined by an enzyme immunoassay.

Round bottom tissue culture treated 96 well microtiter plates (Corning, Corning, N.Y.) were seeded with B7-1 positive CHO cells at $10^3$ cells/well. Two days later the confluent cells were fixed in 95% ethanol for 15 min.

After washing with PBS-Tw, mutant Ig fusion proteins were added at various concentrations and incubated for 1 h at 4° C. After washing, HRP-conjugated goat anti-human IgG (Tago) diluted 1:10,000 was added and incubated for 1 h at 22° C.

Wells were then washed and TMB substrate added as above and allowed to react for 30 min before stopping the reaction with 1N $H_2SO_4$. Absorbance of the wells was measured at 450 nm.

CD28Ig site-directed mutant fusion protein binding assay. Site-directed mutant fusion proteins of CD28Ig were assayed for their ability to bind to B7-1 by an indirect enzyme immunoassay.

Wells of ELISA plates were coated with a chimeric fusion protein containing the extracellular domain of human B7-1 fused to a mouse IgGl Fc region, at 5 µg/ml for 16 h at 4° C. Wells were blocked for 1 h with specimen diluent (Genetic Systems) then washed with PBS-Tw. COS cell culture media containing known concentrations of mutant fusion protein was added at various concentrations and incubated for 1 h at 22° C.

Known concentrations of CD28Ig were also added to separate wells on each plate. After washing, HRP-conjugated goat anti-human IgG (Tago) diluted 1:10,000 was added and incubated for 1 h at 22° C. TMB substrate was added and optical densities read as described for quantitation of Ig fusion proteins in culture media.

mAb binding to Ig fusion proteins. The ability of anti-CTLA4 mab's and the anti-CD28 mAb 9.3 to bind CTLA4/CD28Ig hybrid fusion proteins and CTLA4Ig mutant fusion proteins was assessed by an enzyme immunoassay.

Wells of microtiter plates (Immulon 2) were coated with 0.5 μg/ml of goat anti-human IgG (Jackson) for 16–24 h at 4° C. Plates were blocked for 1 h with specimen diluent (Genetic Systems), washed with PBS-Tw, then incubated with the Ig fusion proteins for 1 h at 22° C. After washing, wells were incubated with mAb at 1 μg/ml for 1 h at 22° C.

After further washing, HRP-conjugated goat anti-mouse Ig (Tago) diluted 1:10,000 was added and incubated for 1 h at 22° C. TMB substrate was added and optical density measured as described above.

CTLA4 molecular model. An approximate three-dimensional model of the CTLA4 extracellular domain was generated based on the conservation of consensus residues of IGSF variable-like domains.

Figure 19:
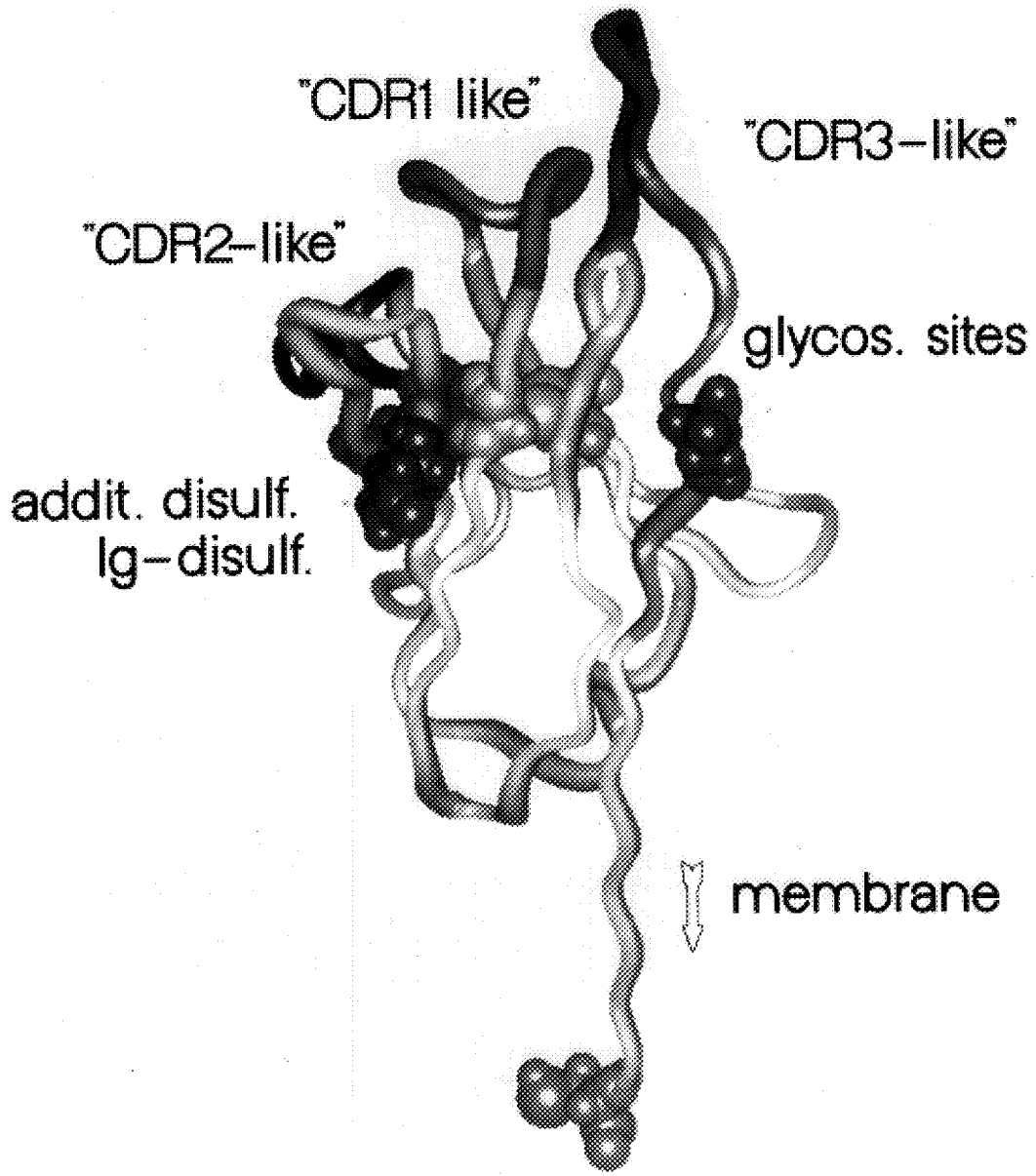
FIG. 19 is a depiction of a molecular model of monomeric CTLA4Ig v-like extracellular domain.

Using such IGSF consensus residues as "anchor points" for sequence alignments, CTLA4 residues were assigned to the A, B, C, C', C", D, E, F, G strands of an Ig variable fold (Williams/Barclay, 1988, supra) and the connecting loop regions (FIG. 19).

The CTLA4 model was built (InsightII, Discover, Molecular Modeling and Mechanics Programs, respectively, Biosym Technologies, Inc., San Diego) using the variable heavy chain of HyHEL-5 (Sheriff et al., 1987 PNAS 84:8075–8079) as template structure. Side-chain replacements and loop conformations were approximated using conformational searching (Bruccoleri et al., 1988 335:564–568).

Several versions of the model with modified assignments of some residues to β-strands or loops were tested using 3D-profile analysis (Luthy et al., 1992, Nature 336:83–85) in order to improve the initial alignment of the CTLA4 extracellular region sequence with an IGSF variable fold.

RESULTS

Construction and binding activity of CTLA4Ig and CD28Ig mutant fusion proteins. A sequence alignment of various homologues of CD28 and CTLA4 is demonstrated in FIG. 15. In FIG. 15, sequences of human (H), mouse (M), rat (R), and chicken (Ch) CD28 are aligned with human and mouse CTLA4. Residues are numbered from the mature protein N-terminus with the signal peptides and transmembrane domains underlined and the CDR-analogous regions noted. Dark shaded areas highlight complete conservation of residues while light shaded areas highlight conservative amino acid substitutions in all family members.

Regions of sequence conservation are scattered throughout the extracellular domains of these proteins with the most rigorous conservation seen in the hexapeptide MYPPPY motif located in the CDR3-like loop of both CTLA4 and CD28 (FIG. 15). This suggests a probable role for this region in the interaction with a B7 antigen, e.g., B7-1 and B7-2.

To test this possibility, site-directed alanine scanning mutations were introduced into this region of CTLA4Ig using PCR oligonucleotide primer-directed mutagenesis thereby resulting in CTLA4Ig mutant fusion proteins. Similarly two alanine mutations were introduced into the CD28Ig MYPPPY motif thereby resulting in CD28Ig mutant fusion proteins.

All cDNA constructs were sequenced to confirm the desired mutations before transfection into COS cells. The concentrations of mutant Ig fusion proteins in serum-free COS cell culture media were determined by an Ig quantitation assay.

The ability of each CTLA4Ig mutant fusion protein to bind to B7-1 expressed on stably transfected CHO cells was then determined by an indirect cell binding immunoassay. Binding of CD28Ig mutant fusion proteins to B7-1 was assessed by an indirect enzyme immunoassay. Each of these assays are described in Materials and Methods.

Mutagenesis of each residue of the CTLA4Ig MYPPPY motif to Ala had a profound effect on binding to B7-1 as shown in FIG. 16. FIG. 16 shows that mutations in the MYPPPY motif of CTLA4Ig and CD28Ig disrupt binding to B7-1. Site-directed mutant Ig fusion proteins were produced in transiently transfected COS cells, quantitated and tested for their ability to bind to B7-1.

In FIG. 16 fusion protein quantitations were repeated at least twice with replicate determinations. Specifically, FIG. 16 shows that CTLA4Ig mutants bind to stably transfected, ethanol-fixed B7-1+ CHO cells grown to confluency in ELISA tissue culture plates. Binding data is expressed as the average of duplicate wells and is representative of at least two experiments.

Y99A and P101A mutants bound to B7-1 but with considerably reduced ability relative to wild-type CTLA4Ig. In contrast, the mutants M98A, P100A, P102A and Y103A showed an almost complete loss of binding. Furthermore, the CD28Ig MYPPPY mutants P103A and Y104A did not display detectable binding to B7-1 immobilized on wells of ELISA plates (FIG. **18*b***).

B7-1 transfected CHO cells which were incubated with CTLA4Ig mutant fusion protein, labeled with anti-human FITC, and assayed using a FACSCAN showed equivalent results. These results clearly demonstrate a critical role for the MYPPPY motif in both CTLA4Ig and CD28Ig binding to B7-1.

Characterization of CTLA4/CD28Ig hybrid fusion proteins. Since the MYPPPY motif is common to both CTLA4Ig and CD28Ig, it alone cannot account for the observed differences in binding to B7-1 seen with CTLA4Ig and CD28Ig. The contribution of less well conserved residues to high avidity binding B7-1 was assessed using a series of homolog mutants.

The three CDR-like regions of CD28 were replaced in various combinations with the equivalent regions from the CTLA4 extracellular domain (FIG. 17 and Table I). FIG. 17 is a map of CTLA4/CD28Ig mutant fusion proteins showing % binding activity to B7-1+ CHO cells relative to CTLA4Ig. Conserved cysteine residues (C) are shown at positions 22, 93 and 121 respectively (CTLA4 numbering). Also shown is the position of the MYPPPY motif. Open areas represent CD28 sequence; filled areas represent CTLA4 sequence; cross-hatched areas represent beginning of IgG Fc (also refer to Table I). Percent binding activities were determined by comparing binding curves (FIGS. **18*a* and 18*b***) relative to CTLA4Ig and finding the concentration of a mutant required to give the same O.D. as that found for CTLA4Ig. The ratio of mutant protein to CTLA4Ig concentration at a particular O.D. was then expressed as % binding activity. At least two A450 readings were taken from the linear part of the CTLA4Ig binding curve and the average % binding activity determined.

A total of 14 hybrid cDNA constructs were prepared, sequenced, and transfected into COS cells. Concentrations of Ig fusion proteins in serum-free culture media were determined and their electrophoretic mobility compared by SDS-PAGE including Western blotting analysis.

Under reducing conditions each chimeric protein migrated with a relative molecular mass ranging between that of CTLA4Ig (Mr-50 kDa) and CD28Ig (Mr-70 kDa) depending on the size of the exchanged region.

Under non-reducing conditions the proteins migrated primarily between 100–140 kDa indicating that these fusion proteins existed as disulfide-linked dimers despite mutagenesis of the cysteine residues in the hinge region of the Fc.

Since four of the five conserved cysteine residues in CTLA4 and CD28 are thought to be involved in intrachain disulfide bonds, dimerization of the fusion proteins was therefore most likely attributable to the fifth conserved cysteine residue at position 121 in CTLA4 (position 123 in CD28).

Binding of CTLA4/CD28Ig hybrid fusion proteins to B7-1. The hybrid fusion proteins were tested for their ability to bind to B7-1 by the same indirect cell binding immunoassay used to assay the site-specific CTLA4Ig and CD28Ig mutant fusion proteins.

Figure 18A:
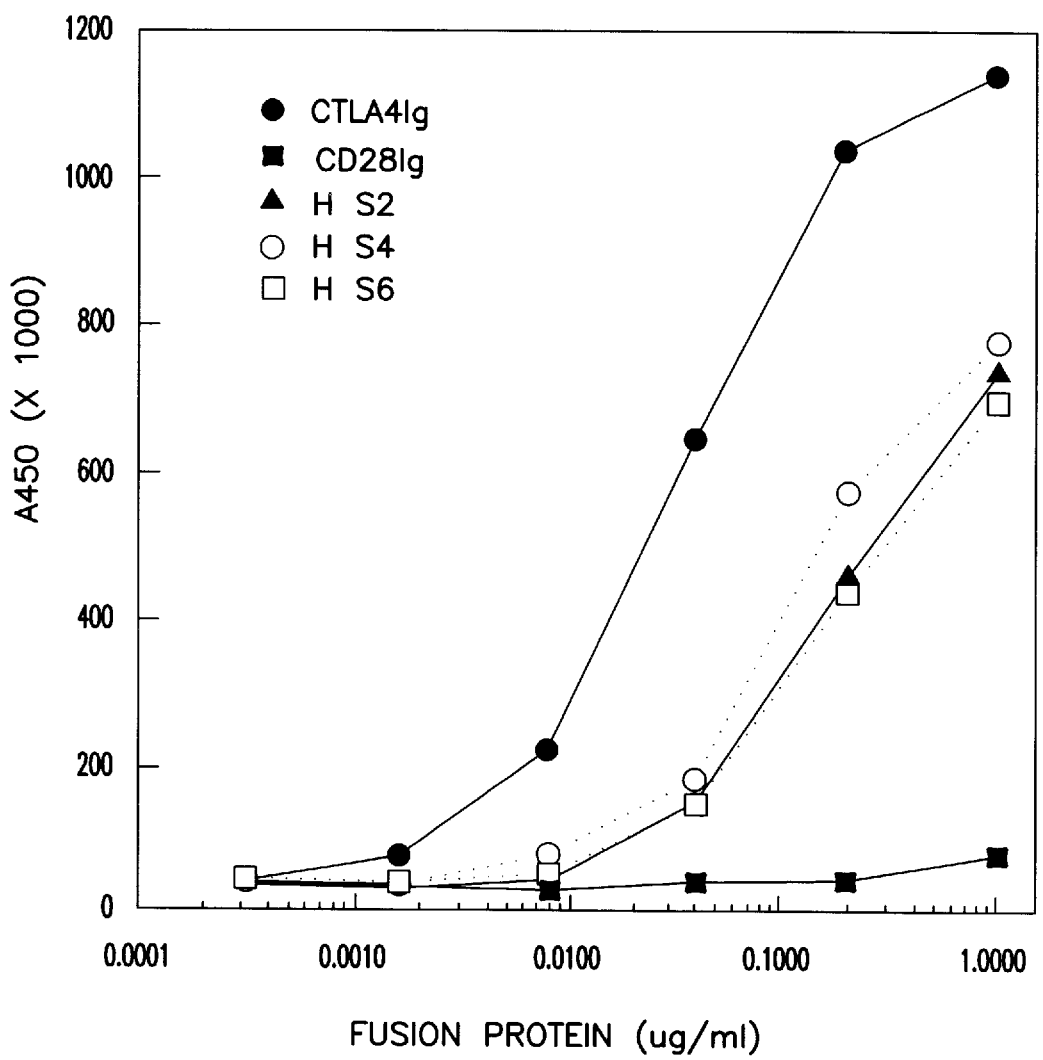
FIGS. 18A and B are line graphs showing that CTLA4/ CD28Ig hybrid fusion proteins bind with high avidity to B7-1 CHO cells.
Figure 18B:
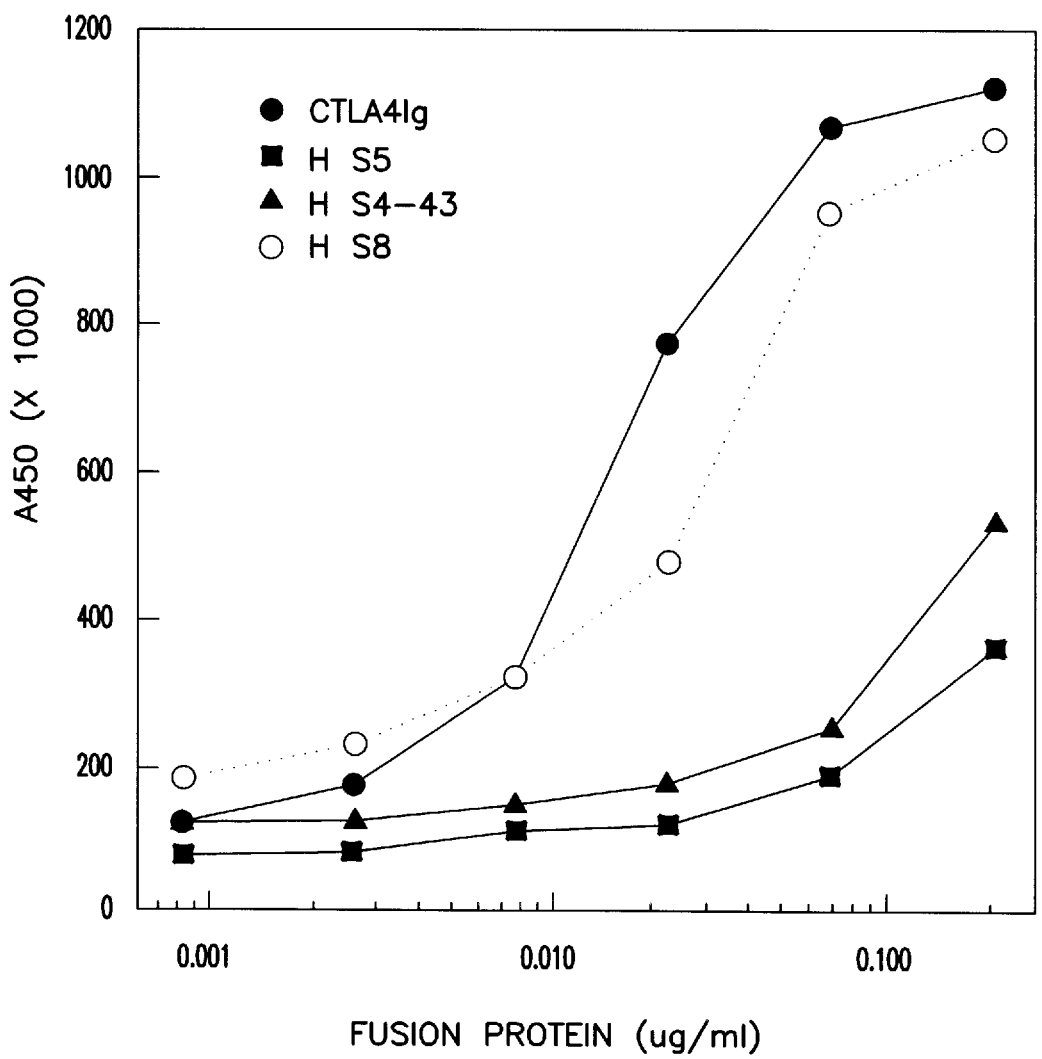

Under these conditions the binding between CD28Ig and B7-1 is barely detectable (FIGS. 18a and 18b). However, replacing residues 97 to 125 (the CDR3-like extended region) of CD28 with the corresponding residues of CTLA4 resulted in an approximately two and a half orders of magnitude increase in binding of the CD28Ig analog to B7-1 (FIGS. 18a and 18b). FIGS. 18a and 18b show that CTLA4/CD28Ig mutant fusion proteins demonstrate involvement of CDR-analogous regions in high avidity binding to B7-1 CHO cells. Mutants were assayed as described in FIG. 2. Data is expressed as the average of duplicate wells and is representative of at least three experiments. From these curves % binding activity relative to CTLA4Ig was determined as explained and shown in FIG. 17.

Binding to B7-1 by this construct, termed HS4 (FIG. 17), is approximately five fold less than wild type CTLA4Ig. The HS2 hybrid which includes additional N-terminal residues of CTLA4 (amino acids 1–22), did not improve the ability of the hybrid molecule to bind to B7-1 relative to HS4.

The HS6 construct which represents the CTLA4Ig sequence except that it contains the CDR1-like region of CD28 (residues 25–32), bound similarly. However, the additional inclusion of the CTLA4 CDR1-like region (residues 25–32) into the HS4 construct (termed HS7), showed further improved binding so that the binding affinity is approximately 44% of CTLA4Ig (FIG. 17).

In contrast, inclusion of the CDR2-like region of CTLA4 (residues 51–58) into HS4 (construct HS10), did not further increase binding (FIG. 17). A similar result was found for construct HS11 which had all three CDR-like region sequences of CTLA4 included into CD28Ig. The HS5 hybrid which contained only the CDR1-like domain of CTLA4 bound at very low levels.

The CTLA4/CD28Ig hybrid HS4-A encoded CTLA4Ig residues 96–113 in the C-terminally extended CDR3-like region; nine CTLA4 derived residues fewer than HS4 (FIG. 17 and Table I). HS4-A bound B7-1 CHO cells less well than HS4 (FIGS. 17 and 20b). However, addition of the CTLA4 CDR1-like loop (HS8 hybrid), increased B7-1 binding from about 2% to nearly 60% of wild type binding.

On the other hand, addition of the CTLA4 CDR2-like loop into HS4-A (HS12) did not increase binding relative to HS4-A; neither did addition of all three CTLA4 CDR-like regions (HS13, FIG. 17).

Another hybrid called HS4-B, encoded the CD28 CDR3-like region including the MYPPPY motif followed by CTLA4 residues 114–122 (Table I and FIG. 17).

HS4-B and HS4-A displayed similar binding to B7-1. Unlike HS4-A, however, the inclusion of the CTLA4 CDR1-like loop into HS4-B (HS9) did not improve binding (FIG. 17), suggesting that residues immediately adjacent to the CTLA4Ig MYPPPY motif were important determinants in high avidity binding.

Monoclonal antibody binding to CTLA4/CD28Ig hybrid fusion proteins. The structural integrity of each hybrid fusion protein was examined by assessing their ability to bind mAb's specific for CTLA4 or CD28 in an enzyme immunoassay. The CTLA4 specific mab's 7F8, 11D4 and 10A8 block ligand binding (Linsley et al. (1992) supra)

These antibodies bound to each of the CTLA4Ig mutant fusion proteins except 11D4 which failed to bind to P100A and P102A (Table II). Since 7F8 and 10A8 bound to these mutants, the lack of binding by 11D4 can probably be attributed to mutagenesis perturbing the epitope recognized by 11D4.

Conversely, each antibody failed to bind to any of the homolog scan hybrid fusion proteins except 7F8 which bound to HS6, and 11D4 which bound weakly to HS8. As many of these homolog hybrid fusion proteins were, to some extent, able to bind to B7-1, it is likely that lack of binding by the antibodies was due to disruption of conformational epitopes formed by spatially adjacent but non-linear sequences.

The CD28 specific mAb 9.3 (Linsley et al. (1992) supra) failed to bind to either of the CD28 site-directed mutant fusion proteins but bound to the hybrid fusion proteins HS4, HS4-A, HS7 and HS8. With HS2, weaker binding was observed. No binding was seen with the HS5 and HS6 constructs.

CTLA4 model. FIG. 19 shows a schematic representation of the CTLA4 model. The assignment of CTLA4 resides to CDR-like regions is shown in FIG. 15. The CTLA4 model suggests the presence of an additional (non-Ig) disulfide bond between residues Cys49 and Cys67 which supports the similarity of CTLA4 and the Ig variable fold.

The two possible N-linked glycosylation sites in CTLA4 map to solvent exposed positions of the Ig β-strand framework regions. 3D-profile analysis indicated that the CTLA4 sequence is overall compatible with an Ig V-fold, albeit more distantly related.

Residue Val115S represents the last residue of the CTLA4Ig-like domain. The conformation of the region between Val115 and the membrane-proximal Cys121 which is thought to form the CTLA4 homodimer is highly variable in the CD28 family. The picture that emerges is that CD28 family members mainly utilize residues in two of three CDR-like regions for binding to B7-1.

The MYPPPY motif represents a conserved scaffold for binding which appears to be augmented by its C-terminal extension and which is specifically modulated by the highly variable CDR1-like region. CDR3 and CDR1-like regions are spatially contiguous in Ig-variable folds. The CDR2 like region is spatially distant and does not, in the case of the CD28 family, significantly contribute to the binding to B7-1.

TABLE I

CTLA4/CD28Ig homolog mutant junction sequences.

| MUTANT | | | | | | | |
|---|---|---|---|---|---|---|---|
| HS1 | -22CKYasp27- | | | | -93ckvEVM99- | | -123CPSDQE- |
| HS2 | -20fvcKYS25- | | | | -94CKIelm98- | | -121cpdDQE- |
| HS3 | | | | | -93ckvEVM99- | | -123CPSDQE- |
| HS4 | | | | | -94CKIelm98- | | -121cpdDQE- |
| HS5 | -22CKYasp27- | -30ateFRA3S- | | | | | -123CPSDQE- |
| HS6 | -22ceySYN27- | -30SREvrv35- | | | | | -121cpdDQE- |
| HS4-A | | | | | -94CKIelm98- | -111tqiHVK118- | -123CPSDQE- |
| HS4-B | | | | | | -113TIIyvi116- | -121cpdDQE- |
| HS7 | -22CKYasp27- | -30ateFRA35- | | | -94CKIelm98- | | -121cpdDQE- |
| HS8 | -22CKYasp27- | -30ateFRA35- | | | -94CKIelm98- | -111tqiHVK118- | -123CPSDQE- |
| HS9 | -22CKYasp27- | -30ateFRA35- | | | | -113TIIyvi116- | -121cpdDQE- |
| HS10 | | | -47VCVaty53- | -56gneLQV60- | -94CKIelm98- | | -121cpdDQE- |
| HS11 | -22CKYasp27- | -30ateFRA35- | -47VCVaty53- | -56gneLQV60- | -94CKLelm98- | | -121cpdDQE- |
| HS12 | | | -47VCVaty53- | -56gneLQV60- | -94CKLeml98- | -111tqiHVK118- | -123CPSDQE- |
| HS13 | -22CKYasp27- | -30ateFRA35- | -47VCVaty53- | -56gneLQV60- | -94CKLelm98- | -111tqiHVK118- | -123CPSDQE- |
| HS14 | | | -47VCVaty53- | -56gneLQV60- | | | -123CPSDQE- |

Junction sequences of the CTLA4/CD28Ig hybrid fusion proteins. Amino acids are denoted by their single letter code with those in upper case being CD28 residues, those in lower case being CTLA4 residues and those in bold upper case being human IgG1 residues. Numbering is from the mature N-terminal of the respective proteins and refer to the adjacent amino acid in the table.

TABLE II

Binding of CTLA4 and CD28 monoclonal antibodies to CTLA4Ig and CD28Ig mutant fusion proteins and to CTLA4/CD28Ig hybrid fusion proteins.

| | anti-CTLA4 mAbs | | | anti-CD28 mAb |
|---|---|---|---|---|
| | 7F8 | 11D4 | 10A8 | 9.3 |
| CTLA4Ig MUTANT FUSION PROTEIN | | | | |
| AYPPPY | +++ | +++ | +++ | - |
| MAPPPY | ++ | + | ++ | - |
| MYAPPY | + | - | + | - |
| MYPAPY | +++ | +++ | +++ | - |
| MYPPAY | +++ | - | + | - |
| MYPPPA | +++ | ++ | +++ | - |
| AAPPPY | + | ++ | +++ | - |
| CD28Ig MUTANT FUSION PROTEIN | | | | |
| MYPPAY | - | - | - | - |
| MYPPPA | - | - | - | + |
| CTLA4/CD28Ig KYBRID FUSION PROTEINS | | | | |
| HS1 | - | - | - | - |
| HS2 | - | - | - | + |
| HS3 | - | - | - | - |
| HS4 | - | - | - | +++ |
| HS5 | - | - | - | - |
| HS6 | + | - | - | - |
| HS4-A | - | - | - | ++ |
| HS4-B | - | - | - | ++ |
| HS7 | - | - | - | +++ |
| HS8 | - | + | - | +++ |
| HS9 | - | + | - | - |
| HS10 | - | - | - | - |
| HS11 | - | - | - | + |
| HS12 | - | - | - | - |
| HS13 | - | - | - | - |
| HS14 | - | - | - | - |
| CTLA4Ig | +++ | +++ | +++ | - |
| CD28Ig | - | - | - | +++ |

Antibody binding was rated from that seen for wild type protein (+++) to above background (+), and no detectable binding (-).

EXAMPLE 7

Dariavach, supra, describes a partial nucleotide sequence of the human CTLA4 gene and sequence of the predicted protein. The sequence is different from the sequence disclosed herein.

The difference lies at amino acid position 111. Dariavach discloses the amino acid alanine having the codon, GCC. In contrast, we disclose the amino acid threonine having the codon ACC. This difference is important because the predicted protein of Dariavach having the sequence disclosed is non-functional, i.e., it does not recognize and bind the B7 antigen.

We determined this fact as follows. A clone comprising the sequence published in Dariavach was made and designated mutant T111A. Mutant T111A was generated by PCR site-directed mutagenesis using CTLA4Ig as template. The DNA containing the single nucleotide mutation at nucleotide position 331 (i.e., guanine instead of adenine) was then cloned into the plasmid vector IILN and subsequently transformed into *E. coli* (strain Mc1061/p3).

The purified DNA was then sequenced to confirm mutation and transfected into COS-7 cells which transiently expressed the secreted protein. The protein was purified over a protein A column and tested for activity in a B7-CHO binding ELISA.

Figure 20:
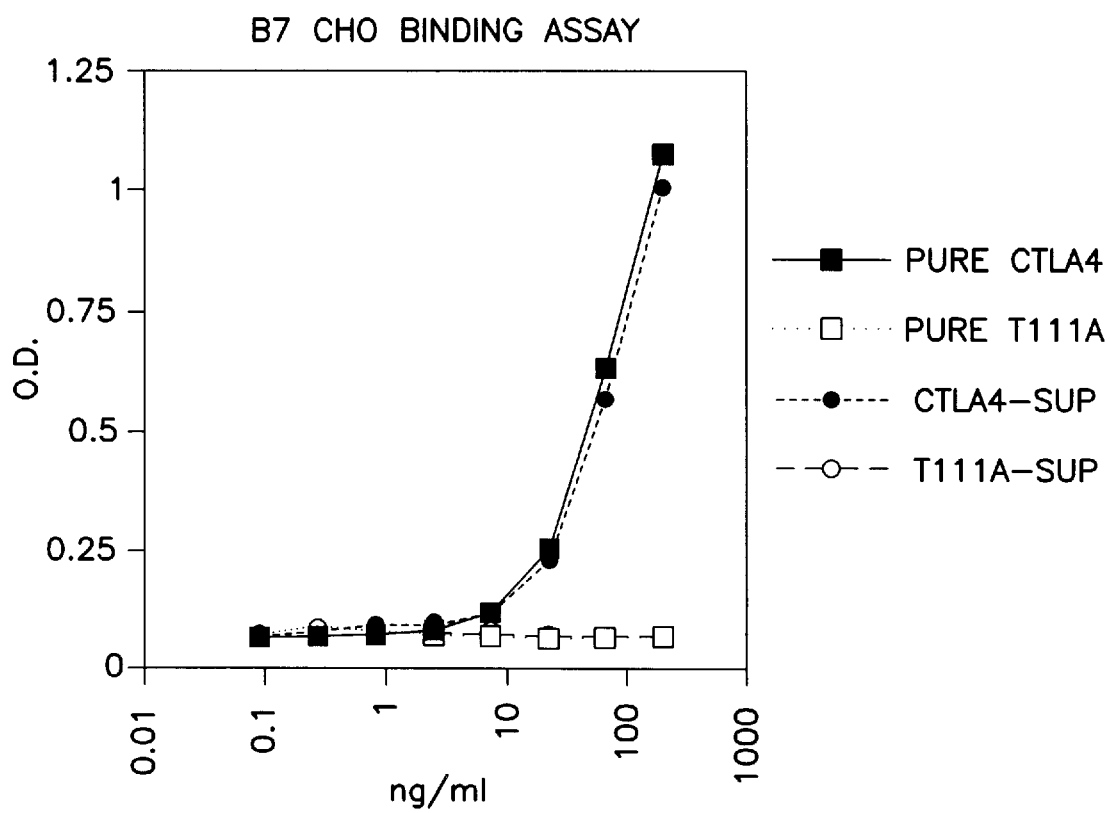
FIG. 20 is a line graph showing that mutant T111A which includes the CTLA4 sequence of Dariavach et al., 1988, supra, does not bind B7. The CTLA4 of the invention (FIG. 3) does bind B7.

B7-1 expressing CHO cells were seeded into a 96-well microtiter plate, fixed and washed. Samples were added starting at 200 ng/ml followed by serial 3 fold dilutions. Binding was detected by goat anti-human Ig-HRP plus chromogenic substrate. The plates were then read in an ELISA reader at 450/630 nm. The result is set forth in FIG. 20. FIG. 20 shows that our CTLA4 protein binds B7, Dariavach's CTLA4 embodied in T111A did not bind B7.

EXAMPLE 8

Construction and Expression of soluble CTLA4 fusion proteins

The appropriate DNA fragments of CTLA4 and the protein partners or tags (e.g., biologically or chemically active molecules such as ovalbumin, p97, E7, and env gp120) were isolated from the cDNA by PCR ((U.S. Pat. Nos. 4,683,195 and 4,683,202 to Mullis et al. and Mullis & Faloona, *Methods Enzymol.* 154:335–350 (1987)).

DNA for the fusion proteins of CTLA4 was then prepared by ligating DNA of CTLA4 with that of the various protein tags. In ELISA and FACS assays, the binding and expression of the soluble CTLA4 fusion protein was detected using antibodies directed against the tag, e.g., ovalbumin, env gp120, HPV E7, and p97.

The DNA sequence of the ovalbumin gene was known (Schweers et al. J. Biol. Chem. (1990) 265(13):7590–5); the DNA sequence of the E7 papillovirus oncogene was known (Tindle et al. J. Gen. Vir. (1990) 71:1347–54; the DNA sequence of the melanoma-asociated antigen p97 was known (Kahn et al. J. Immunol. (1991) 146(9):3235–41); the DNA sequence of env gp120 was known (Wain-Hobson et al. "Nucleotide sequence of aids virus LAV" Cell (1985) 40:9–17; Ratner et al. "Complete nucleotide sequence of the the aids virus HTLV3" Nature 313:277–284 (1985)). The identity of the resulting genes for each of the soluble molecules (i.e., fusion proteins) was confirmed by DNA sequencing.

The cDNA of the fusion proteins were then expressed either in mammalian (cos, DEAE dextran transfection) or insect (baculovirus transfection) cell lines (Jones et al. Nature (1986) 523:346). The supernatants of the transfected cell lines were harvested, assayed and the fusion proteins then purified by affinity chromatography.

Bifunctional Assays for soluble CTLA4 molecules

Soluble CTLA4 molecules were evaluated for their ability to bind to B7 by two independent assay protocols. The binding of the fusion proteins to cells expressing B7 was measured by FACS analysis (FIGS. 28–31), and the binding of the proteins to immobilized B7-Ig was followed by ELISA (FIGS. 32–35).

In the FACS assays, the binding of the fusion proteins to a B cell line, B414, that expresses B7-1, was determined following incubation of the cells with either cell supernatants or purified fusion protein. Bound fusion protein was detected with an antibody to the C-terminus region of the fusion protein (FIGS. 28–31).

Specifically, in the ELISA and FACS assays, when detecting the binding of the CTLA4-E7 fusion protein, antibodies which recognize and bind the E7 portion of the fusion protein were used (L. P. Chen et al. PNAS U.S.A. (1991) 88(1):110–4; L. Chen et al. PNAS U.S.A. (1993) 90(14):6523–7; G. W. Demers et al. Virology (1994) 198(1):169–74).

When detecting the binding of the CTLA4-ova fusion protein, antibodies which recognize and bind the ovalbumin portion of the fusion protein were used (Cappell).

When detecting the binding of the CTLA4-env gp120 fusion protein, antibodies (110.4 mAb) which recognize and bind the env gp120 portion of the fusion protein were used (J. D. Oram et al. Aids Research and Human Retroviruses (1991) 7(4):417–21.

When detecting the binding of the CTLA4-p97 fusion protein, antibodies which recognize and bind the p97 portion of the fusion protein were used (M. Kahn et al. J. Immunol. (1991) 146(9):3235–41).

The soluble CTLA4 fusion protein/antibody complex was in turn visualized with a FITC-labelled second antibody. Binding of all the different fusion proteins to the B cells was competitively inhibited by soluble CTLA4Ig.

In the ELISA assays, B7-1 (2.5 µg/ml) was immobilized to 96 well microtiter plates, samples were blocked with sample diluent, and the fusion proteins were then serially diluted down the plates. After 2 h incubation the plates were washed and then treated with the appropriate antibodies to the carboxy terminus of the fusion protein (specific protocol in Example 4, supra). Following an incubation of 1 h the plates were washed and then treated with an HRP-conjugated second antibody for an additional 1 h. The plates were developed with HRP substrate and then quantitated in an ELISA plate reader. The results are presented as Optical Density at 450 nm plotted against serial dilution of the fusion protein.

The results obtained from both the FACS analysis and the ELISA indicate that the fusion proteins bind to B7 via the CTLA4 region at the amino terminus, and have a free carboxy terminus that can be detected with specific anti-protein antibodies. Moreover binding of the fusion proteins to B7, either on the surface of cells or immobilized on a plate can be inhibited by CTLA4Ig. Therefore, CTLA4 can be expressed in a soluble form with a variety of different protein partners (protein "tags") at the carboxy terminus and retain specific binding to B7.

EXAMPLE 9

Studies were conducted to evaluate CTLA4Ig-mediated immunosuppression in non-human primates. Cynomolgus monkeys were administered with 0, 0.67, 2.0 or 6.0 mg/kg CTLA4Ig intravenously, two-times per week for three weeks.

On Day 1 (first day of dosing) and Day 102 animals were immunized with sheep red blood cells (SRBC: iv, 1.7 ml/kg of a 10% mixture). Serum and whole blood samples were obtained pre-dose and at least 4 weeks following primary and secondary immunization for assessment of anti-SRBC antibodies, serum gamma globulin levels, pharmacokinetics, clinical hematology and lymphocyte subpopulations ($CD2^+$, $CD4^+$, $CD8^+$, and $CD20^+$).

Figure 21:
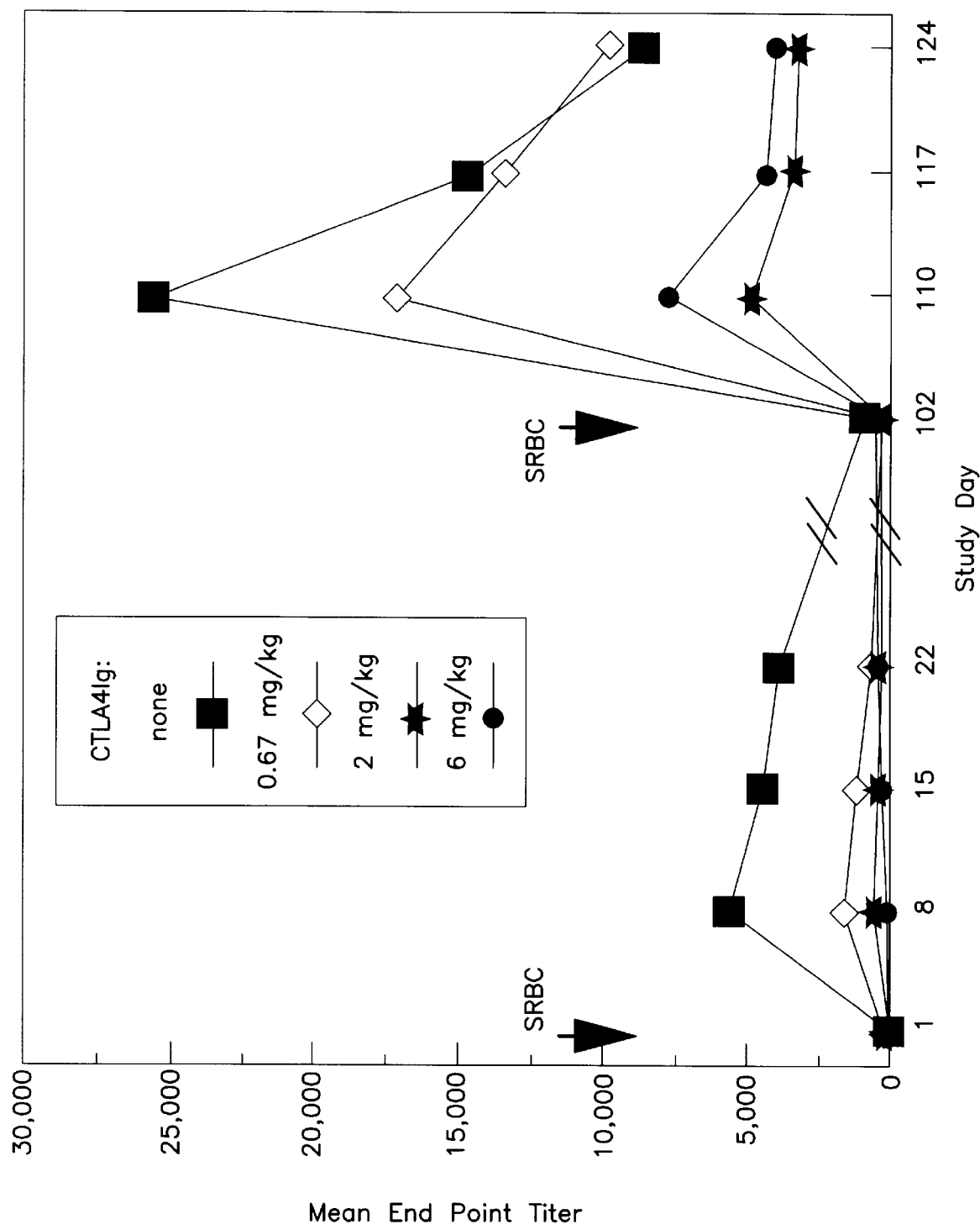
FIG. 21 is a line graph showing that CTLA4Ig significantly suppresses the immune response directed against SRBCs in cynomolgus monkeys (primary versus secondary response).
Figure 22:
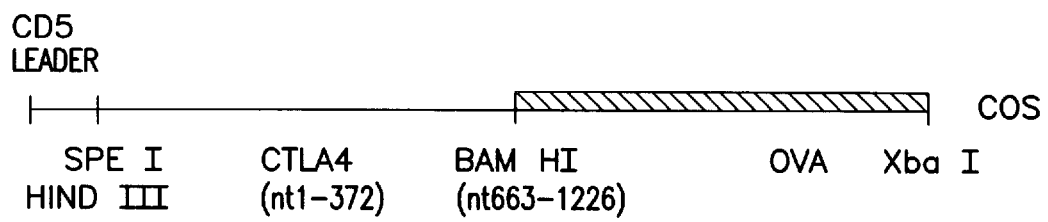
FIG. 22 is a schematic diagram of the vector construct of soluble CTLA4-ova having CD5 as the leader sequence. The portion of the ovalbumin (ova) gene (nucleotide positions 663–1226) was recombined to be located 3' of the CTLA4 sequence.
Figure 23:
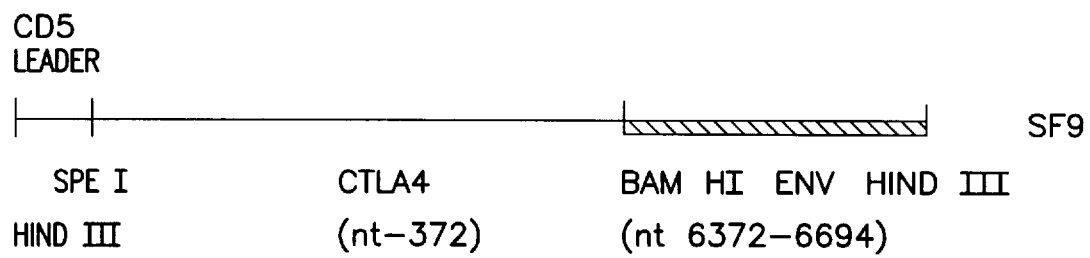
FIG. 23 is a schematic diagram of the vector construct of soluble CTLA4-env gp120 having CDS as the leader sequence. The portion of the envelope (env) gene (nucleotide positions 6372–6694) was recombined to be located 3' of the CTLA4 sequence.
Figure 24:
FIG. 24 is a schematic diagram of the vector construct of soluble CTLA4-p97 having CD5 as the leader sequence. The portion of the p97 gene (nucleotide positions 19–1097) was recombined to be located 3' of the CTLA4 sequence.
Figure 25:
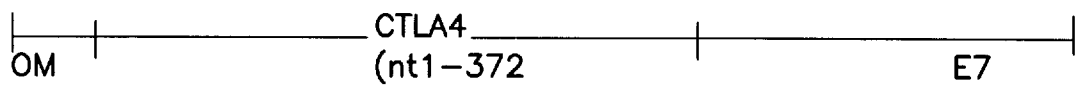
FIG. 25 is a schematic diagram of the vector construct of soluble CTLA4-E7 having CD5 as the leader sequence. A portion of the E7 gene was recombined to be located 3' of the CTLA4 sequence.
Figure 32:
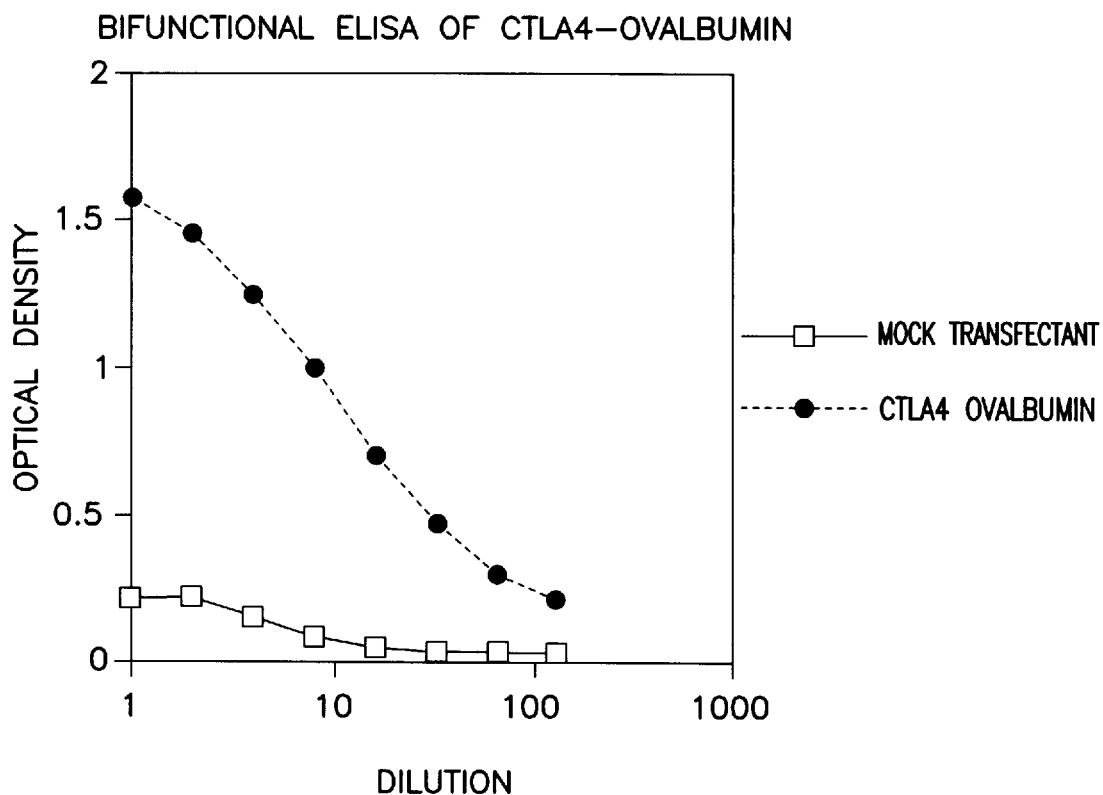
FIG. 32 is a line graph showing that soluble CTLA4-ova (closed circle) binds immobilized B7 in an ELISA assay. The antibody in the ELISA assay recognizes and binds the ovalbumin portion of soluble CTLA4-ova.
Figure 34:
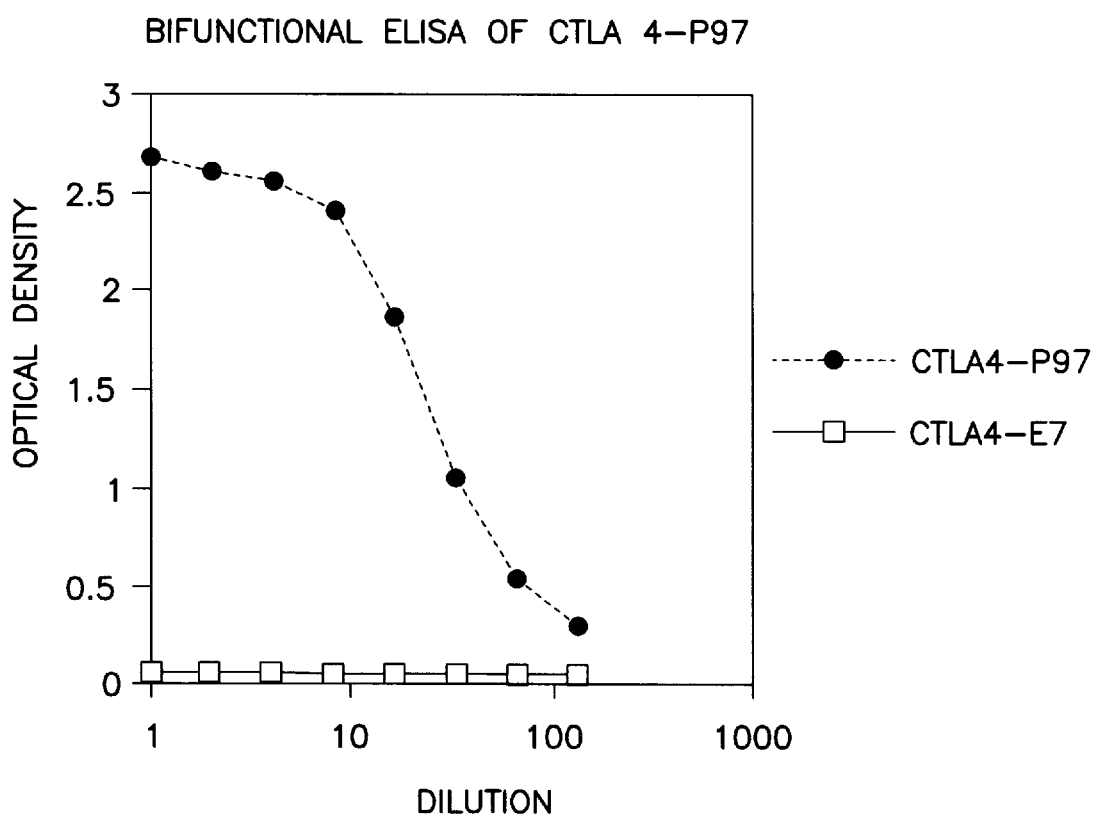
FIG. 34 is a line graph showing that CTLA4-p97 (closed circle) binds immobilized B7 in an ELISA assay. The antibody in the ELISA assay recognizes and binds the p97 portion of soluble CTLA4-p97.
Figure 35:
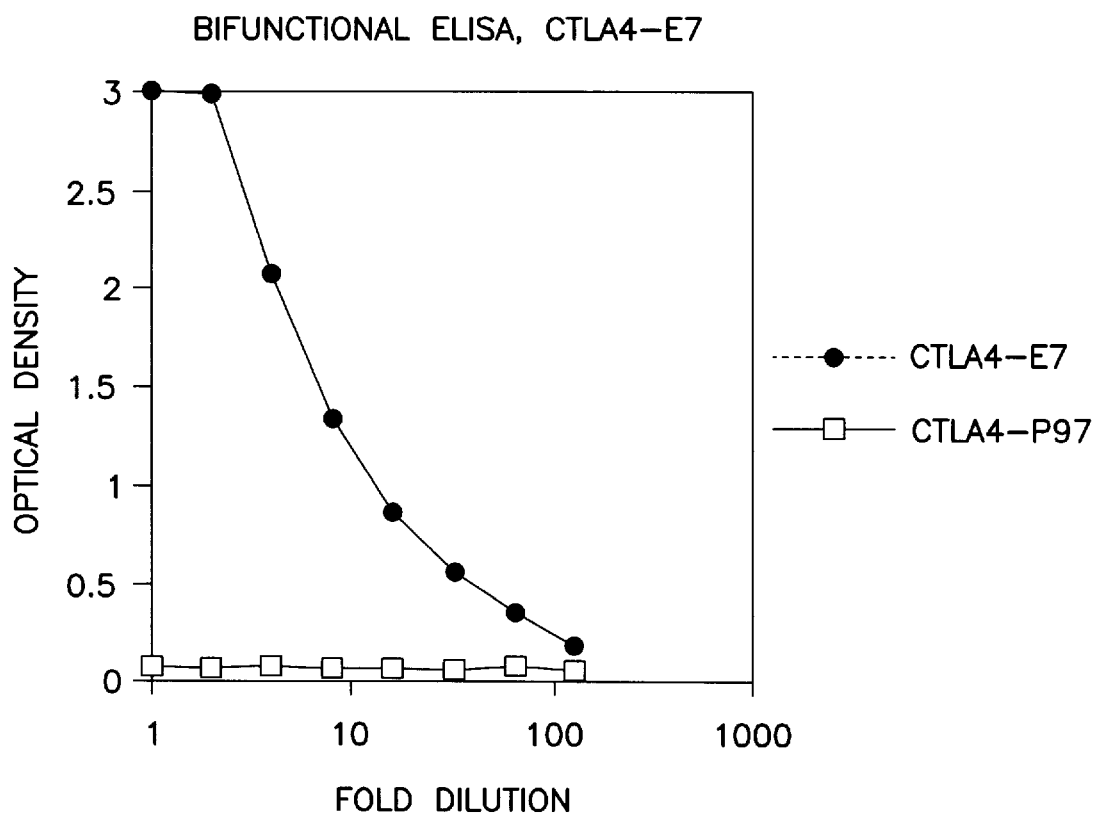
FIG. 35 is a line graph showing that CTLA4-E7 (closed circle) binds immobilized B7 in an ELISA assay. The antibody in the ELISA assay recognizes and binds the E7 portion of soluble CTLA4-E7.

A dose dependent decrease in anti-SRBC antibodies was observed following primary immunization, with maximal suppression of >95% (FIG. 21). Monkeys treated with CTLA4Ig were able to respond to a secondary challenge with SRBCs (Day 102, no circulating levels of CTLA4Ig), The response in the high dose monkeys was similar to the primary response observed in control monkeys following a single immunization with SRBCs. No treatment-related changes were noted in the frequency of T-cells, or subpopulations of T-cells.

Pharmacokinetic analysis suggests linearity between dose and serum levels of CTLA4Ig ($C_{max}$ and AUC), with a T½ of between 106 and 161 hours. These results indicate that CTLA4Ig inhibits the antibody response directed against SRBCs in cynomolgus monkeys.

EXAMPLE 10

Studies of the rejection process and modification thereof are reported using the recombinant soluble CTLA4Ig. CTLA4Ig should bind tightly to rat B7/BB1 on APCS, blocking binding of B7/BB1 to CD28/CTLA-4 on T cells. This interaction interrupts the costimulatory pathway crucial for T cells activation and cytokine production.

These studies were done to see whether CTLA4Ig blocks T cell-dependent immune reactions, including acute rejection, as in BN to LEW rat heart transplants.

The left single lung transplantations were performed BN to LEW (RT1n to RT1l). This model shows florid acute rejection with all grafts completely destroyed by day 7 post-transplant. Graft pathology is characterized by massive lymphocytic infiltrates and hemorrhagic necrosis.

Experimental groups received 250 µg CTLA4Ig daily intraperitoneally (ip) after transplantation. Control groups received 250 µg of chimeric monoclonal antibody L6.

Five lung allograft recipients in each group were sacrificed on days 2, 4 and 7 post-transplant. Lung allografts were graded histologically (stage I–IV) and several pathological categories of inflammation were examined and scored (0–4), with a score of 0=0% involvement; 1=1–25% involvement; 2=26–50% involvement, 3=51–75% involvement, 4=76–100% involvement.

Intragraft levels of key cytokine transcripts are detected by RT-PCR and RNA electroblots. The mean and S.D. scores were obtained for all animals in the treatment groups mentioned above, and compared to L6 treated controls.

The results are as follows. On days 2 and 4, control and treated grafts had the same pathological staging (day 2, 1.2±0.447 vs 1±0; day 4, 2± vs 2±0). However by day 7, clear differences were seen in staging: (4±0 vs 3±0, $p<0.01$).

Differences were specifically seen in scores for edema (3.6±0.894 vs 1.8±0.837, $p<0.05$), vasculitis (2.6±0.548 vs 1±0.707, $p<0.05$), necrosis (2.4±0.548 vs 0±0, $p<0.005$) and interalveolar hemorrhage (3.2±0.447 vs 0.4±0.548, $p<0.01$).

The scores for cellular infiltrations in treated grafts were higher than controls; as manifest by perivascular infiltration (2.6±0.548 vs 4±0, $p<0.01$), peribronchial infiltration (2.2±0.447 vs 4±0, $p<0.01$) and peribronchiolar infiltration (2±0.707 vs 3.6±0.548, $p<0.05$).

Intragraft transcript levels of IL-2, IFN-gamma and TNF-alpha were similar in control and treated groups on days 4 and 7, measured by RT-PCR. IL-2 was clearly detected on electroblots on day 7 in the treated group.

Although the intensity of cellular infiltration was not prevented by CTLA4Ig therapy, soluble CTLA4Ig prevents hemorrhagic necrosis in transplanted rat lungs. CTLA4Ig blocks graft destruction without inhibiting intragraft mRNA levels for cytokines (IL-2, IFN-gamma and TNF-alpha) important in the allograft rejection process.

---

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTAGCCACTG AAGCTTCACC ATGGGTGTAC TGCTCACAC 39

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TGGCATGGGC TCCTGATCAG GCTTAGAAGG TCCGGGAAA 39

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TTTGGGCTCC TGATCAGGAA AATGCTCTTG CTTGGTTGT 39

( 2 ) INFORMATION FOR SEQ ID NO:4:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear -continued ( i i ) MOLECULE TYPE: DNA (genomic)

( x i ) SEQUENCE DESCRIPTION: SEQ ID NO:4:

AAGCAAGAGC ATTTTCCTGA TCAGGAGCCC AAATCTTCTG ACAAAACTCA CACATCCCCA    60

CCGTCCCCAG CACCTGAACT CCTG    84

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CTTCGACCAG TCTAGAAGCA TCCTCGTGCG ACCGCGAGAG C    41

( 2 ) INFORMATION FOR SEQ ID NO:6:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CATTGCACAG TCAAGCTTCC ATGCCCATGG GTTCTCTGGC CACCTTG    47

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATCCACAGTG CAGTGATCAT TTGGATCCTG GCATGTGAC    39

( 2 ) INFORMATION FOR SEQ ID NO:8:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CTCAGTCTGG TCCTTGCACT CCTGTTTCCA AGCATGGCGA GCATGGCAAT GCACGTGGCC    60

CAGCC    65

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TTTGGGCTCC TGATCAGAAT CTGGGCACGG TTG 33

( 2 ) INFORMATION FOR SEQ ID NO:10:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CTAGCCACTG AAGCTTCACC AATGGGTGTA CTGCTCACAC AGAGGACGCT GCTCAGTCTG 60

GTCCTTGCAC TC 72

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GCAATGCACG TGGCCCAGCC TGCTGTGGTA GTG 33

( 2 ) INFORMATION FOR SEQ ID NO:12:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TGATGTAACA TGTCTAGATC AATTGATGGG AATAAAATAA GGCTG 45

( 2 ) INFORMATION FOR SEQ ID NO:13:

( i ) SEQUENCE CHARACTERISTICS:
        ( A ) LENGTH: 561 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..561

( x i ) SEQUENCE DESCRIPTION: SEQ ID NO:13:

```
GCA  ATG  CAC  GTG  GCC  CAG  CCT  GCT  GTG  GTA  CTG  GCC  AGC  AGC  CGA  GGC        48
Ala  Met  His  Val  Ala  Gln  Pro  Ala  Val  Val  Leu  Ala  Ser  Ser  Arg  Gly
 1              5                        10                       15

ATC  GCC  AGC  TTT  GTG  TGT  GAG  TAT  GCA  TCT  CCA  GGC  AAA  GCC  ACT  GAG        96
Ile  Ala  Ser  Phe  Val  Cys  Glu  Tyr  Ala  Ser  Pro  Gly  Lys  Ala  Thr  Glu
              20                        25                       30

GTC  CGG  GTG  ACA  GTG  CTT  CGG  CAG  GCT  GAC  AGC  CAG  GTG  ACT  GAA  GTC       144
Val  Arg  Val  Thr  Val  Leu  Arg  Gln  Ala  Asp  Ser  Gln  Val  Thr  Glu  Val
         35                        40                       45
```

| | | | | | | | | | | | | | | | | |
|---|---|---|---|---|---|---|---|---|---|---|---|---|---|---|---|---|
| TGT | GCG | GCA | ACC | TAC | ATG | ATG | GGG | AAT | GAG | TTG | ACC | TTC | CTA | GAT | GAT | 192 |
| Cys | Ala | Ala | Thr | Tyr | Met | Met | Gly | Asn | Glu | Leu | Thr | Phe | Leu | Asp | Asp | |
| | 50 | | | | | 55 | | | | | 60 | | | | | |
| TCC | ATC | TGC | ACG | GGC | ACC | TCC | AGT | GGA | AAT | CAA | GTG | AAC | CTC | ACT | ATC | 240 |
| Ser | Ile | Cys | Thr | Gly | Thr | Ser | Ser | Gly | Asn | Gln | Val | Asn | Leu | Thr | Ile | |
| 65 | | | | | 70 | | | | | 75 | | | | | 80 | |
| CAA | GGA | CTG | AGG | GCC | ATG | GAC | ACG | GGA | CTC | TAC | ATC | TGC | AAG | GTG | GAG | 288 |
| Gln | Gly | Leu | Arg | Ala | Met | Asp | Thr | Gly | Leu | Tyr | Ile | Cys | Lys | Val | Glu | |
| | | | | 85 | | | | | 90 | | | | | 95 | | |
| CTC | ATG | TAC | CCA | CCG | CCA | TAC | TAC | CTG | GGC | ATA | GGC | AAC | GGA | ACC | CAG | 336 |
| Leu | Met | Tyr | Pro | Pro | Pro | Tyr | Tyr | Leu | Gly | Ile | Gly | Asn | Gly | Thr | Gln | |
| | | | 100 | | | | | 105 | | | | | 110 | | | |
| ATT | TAT | GTA | ATT | GAT | CCA | GAA | CCG | TGC | CCA | GAT | TCT | GAC | TTC | CTC | CTC | 384 |
| Ile | Tyr | Val | Ile | Asp | Pro | Glu | Pro | Cys | Pro | Asp | Ser | Asp | Phe | Leu | Leu | |
| | | 115 | | | | | 120 | | | | | 125 | | | | |
| TGG | ATC | CTT | GCA | GCA | GTT | AGT | TCG | GGG | TTG | TTT | TTT | TAT | AGC | TTT | CTC | 432 |
| Trp | Ile | Leu | Ala | Ala | Val | Ser | Ser | Gly | Leu | Phe | Phe | Tyr | Ser | Phe | Leu | |
| | | 130 | | | | | 135 | | | | | 140 | | | | |
| CTC | ACA | GCT | GTT | TCT | TTG | AGC | AAA | ATG | CTA | AAG | AAA | AGA | AGC | CCT | CTT | 480 |
| Leu | Thr | Ala | Val | Ser | Leu | Ser | Lys | Met | Leu | Lys | Lys | Arg | Ser | Pro | Leu | |
| 145 | | | | | 150 | | | | | 155 | | | | | 160 | |
| ACA | ACA | GGG | GTC | TAT | GTG | AAA | ATG | CCC | CCA | ACA | GAG | CCA | GAA | TGT | GAA | 528 |
| Thr | Thr | Gly | Val | Tyr | Val | Lys | Met | Pro | Pro | Thr | Glu | Pro | Glu | Cys | Glu | |
| | | | | 165 | | | | | 170 | | | | | 175 | | |
| AAG | CAA | TTT | CAG | CCT | TAT | TTT | ATT | CCC | ATC | AAT | | | | | | 561 |
| Lys | Gln | Phe | Gln | Pro | Tyr | Phe | Ile | Pro | Ile | Asn | | | | | | |
| | | | 180 | | | | | 185 | | | | | | | | |

(2) INFORMATION FOR SEQ ID NO:14:

(i) SEQUENCE CHARACTERISTICS:
        (A) LENGTH: 187 amino acids
        (B) TYPE: amino acid
        (D) TOPOLOGY: linear (ii) MOLECULE TYPE: protein (xi) SEQUENCE DESCRIPTION: SEQ ID NO:14:

| | | | | | | | | | | | | | | |
|---|---|---|---|---|---|---|---|---|---|---|---|---|---|---|
| Ala | Met | His | Val | Ala | Gln | Pro | Ala | Val | Val | Leu | Ala | Ser | Ser | Arg | Gly |
| 1 | | | | 5 | | | | | 10 | | | | | 15 | |
| Ile | Ala | Ser | Phe | Val | Cys | Glu | Tyr | Ala | Ser | Pro | Gly | Lys | Ala | Thr | Glu |
| | | | 20 | | | | | 25 | | | | | 30 | | |
| Val | Arg | Val | Thr | Val | Leu | Arg | Gln | Ala | Asp | Ser | Gln | Val | Thr | Glu | Val |
| | | 35 | | | | | 40 | | | | | 45 | | | |
| Cys | Ala | Ala | Thr | Tyr | Met | Met | Gly | Asn | Glu | Leu | Thr | Phe | Leu | Asp | Asp |
| | 50 | | | | | 55 | | | | | 60 | | | | |
| Ser | Ile | Cys | Thr | Gly | Thr | Ser | Ser | Gly | Asn | Gln | Val | Asn | Leu | Thr | Ile |
| 65 | | | | | 70 | | | | | 75 | | | | | 80 |
| Gln | Gly | Leu | Arg | Ala | Met | Asp | Thr | Gly | Leu | Tyr | Ile | Cys | Lys | Val | Glu |
| | | | | 85 | | | | | 90 | | | | | 95 | |
| Leu | Met | Tyr | Pro | Pro | Pro | Tyr | Tyr | Leu | Gly | Ile | Gly | Asn | Gly | Thr | Gln |
| | | | 100 | | | | | 105 | | | | | 110 | | |
| Ile | Tyr | Val | Ile | Asp | Pro | Glu | Pro | Cys | Pro | Asp | Ser | Asp | Phe | Leu | Leu |
| | | 115 | | | | | 120 | | | | | 125 | | | |
| Trp | Ile | Leu | Ala | Ala | Val | Ser | Ser | Gly | Leu | Phe | Phe | Tyr | Ser | Phe | Leu |
| | | 130 | | | | | 135 | | | | | 140 | | | |
| Leu | Thr | Ala | Val | Ser | Leu | Ser | Lys | Met | Leu | Lys | Lys | Arg | Ser | Pro | Leu |
| 145 | | | | | 150 | | | | | 155 | | | | | 160 |
| Thr | Thr | Gly | Val | Tyr | Val | Lys | Met | Pro | Pro | Thr | Glu | Pro | Glu | Cys | Glu |

```
                                  165                           170                           175
Lys Gln Phe Gln Pro Tyr Phe Ile Pro Ile Asn
                180                           185

( 2 ) INFORMATION FOR SEQ ID NO:15:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:15:

AATACGACTC ACTATAGG                                                                                    1 8

( 2 ) INFORMATION FOR SEQ ID NO:16:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:16:

CACCACACTG TATTAACC                                                                                    1 8

( 2 ) INFORMATION FOR SEQ ID NO:17:

( i ) SEQUENCE CHARACTERISTICS:
                ( A ) LENGTH: 1021 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:17:

ATGCCCATGG GGTCTCTGCA ACCGCTGGCC ACCTTGTACC TGCTCCCCAT CCTCCTCGCT          6 0
TCCTGCCTCG GACTAGTCAG CAATGCACGT GGCCCAGCCT GCTGTGGTAC TGGCCAGCAG         1 2 0
CGGAGGCATC AGCTTTGTGT GTGAGTATGC ATCTCCAGGC AAAGCCACTG AGGTCCGGGT         1 8 0
GACAGTGCTT CGGCAGGCTG ACAGCCAGGT GACTGAAGTC TGTGCGGCAA CCTACATGAT         2 4 0
GGGGAATGAG TTGACCTTCC TAGATGATTC CATCTGCACG GGCACCTCCA GTGGAAATCA         3 0 0
AGTGAACCTC ACTATCCAAG GACTGAGGGC CATGGACACG GGACTCTACA TCTGCAAGGT         3 6 0
GGAGCTCATG TACCCACCGC CATACTACCT GGGCATAGGC AACGGAGCCC AGATTTATGT         4 2 0
AATTGATCCA GAACCGTGCC CAGTATCTGG ATCCAGAGTG ACTGAGCAAG AAAGCAAACC         4 8 0
TGTGCAGATG ATGTACCAGA TTGGTTTATT TAGAGTGGCA TCAATGGCTT CTGAGAAAAT         5 4 0
GAAGATCCTG GAGCTTCCAT TTGCCAGTGG ACAATGAGC ATGTTGGTGC TGTTGCCTGA         6 0 0
TGAAGTCTCA GGCCTTGAGC AGCTTGAGAG TATAATCAAC TTTGAAAAAC TGACTGAATG         6 6 0
GACCAGTTCT AATGTTATGG AAGAGAGGAA GATCAAAGTG TACTTACCTC GCATGAAGAT         7 2 0
GGAGGAAAAA TACAACCTCA CATCTGTCTT AATGGCTATG GGCATTACTG ACGTGTTTAG         7 8 0
CTCTTCAGCC AATCTGTCTG GCATCTCCTC AGCAGAGAGC CTGAAGATAT CTCAAGCTGT         8 4 0
CCATGCAGCA CATGCAGAAA TCAATGAAGC AGGCAGAGAG GTGGTAGGGT CAGCAGAGGC         9 0 0
TGGAGTGGAT GCTGCAAGCG TCTCTGAAGA ATTTAGGGCT GACCATCCAT TCCTCTTCTG         9 6 0
```

| | | | | | |
|---|---|---|---|---|---|
| TATCAAGCAC ATCGCAACCA ACGCCGTTCT CTTCTTTGGC AGATGTGTTT GATAGAAGGT | | | | | 1020 |
| T | | | | | 1021 |

( 2 ) INFORMATION FOR SEQ ID NO:18:

( i ) SEQUENCE CHARACTERISTICS:
        ( A ) LENGTH: 781 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

| | | | | | |
|---|---|---|---|---|---|
| ATGCCCATGG GGTCTCTGCA ACCGCTGGCC ACCTTGTACC TGCTCCCCAT CCTCCTCGCT | | | | | 60 |
| TCCTGCCTCG GACTAGTCAG CAATGCACGT GGCCCAGCCT GCTGTGGTAC TGGCCAGCAG | | | | | 120 |
| CCGAGGCATC AGCTTTGTGT GTGAGTATGC ATCTCCAGGC AAAGCCACTG AGGTCCGGGT | | | | | 180 |
| GACAGTGCTT CGGCAGGCTG ACAGCCAGGT GACTGAAGTC TGTGCGGCAA CCTACATGAT | | | | | 240 |
| GGGGAATGAG TTGACCTTCC TAGATGATTC CATCTGCACG GGCACCTCCA GTGGAAATCA | | | | | 300 |
| AGTGAACCTC ACTATCCAAG GACTGAGGGC CATGGACACG GGACTCTACA TCTGCAAGGT | | | | | 360 |
| GGAGCTCATG TACCCACCGC CATACTACCT GGGGATAGGC AACGGAGCCC AGATTTATGT | | | | | 420 |
| AATTGATCCA GAACCGTGCC CAGTATCTGG ATCCCTGTTG AATGGCAGTC TAGCAGAAGA | | | | | 480 |
| AGAGGTAGTA ATTAGATCTG CCAATTTCAC AGACAATGCT AAAACCATAA TAGTACAGCT | | | | | 540 |
| GAACCAATCT GTAGAAATTA ATTGTACAAG ACCCAACAAC AATACAAGAA AAAGTATCCG | | | | | 600 |
| TATCCAGAGG GGACCAGGGA GAGCATTTGT TACAATAGGA AAATAGGAA ATATGAGACA | | | | | 660 |
| AGCACATTGT AACATTAGTA GAGCAAAATG GAATGCCACT TTAAAACAGA TAGCTAGCAA | | | | | 720 |
| ATTAAGAGAA CAATTTGGAA ATAATAAAAC AATAATCTTT AAGCAATCCT GAGGAAAGCT | | | | | 780 |
| T | | | | | 781 |

( 2 ) INFORMATION FOR SEQ ID NO:19:

( i ) SEQUENCE CHARACTERISTICS:
        ( A ) LENGTH: 502 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:19:

```
Gln Ala Ser Pro Met Gly Val Leu Leu Thr Gln Arg Thr Leu Leu Ser
 1               5                  10                  15

Leu Val Leu Ala Leu Leu Phe Pro Ser Met Ala Ser Met Ala Met His
            20                  25                  30

Val Ala Gln Pro Ala Val Val Leu Ala Ser Ser Arg Gly Ile Ala Ser
        35                  40                  45

Phe Val Cys Glu Tyr Ala Ser Pro Gly Lys Ala Thr Glu Val Arg Val
    50                  55                  60

Thr Val Leu Arg Gln Ala Asp Ser Gln Val Thr Glu Val Cys Ala Ala
65                  70                  75                  80

Thr Tyr Met Met Gly Asn Glu Leu Thr Phe Leu Asp Asp Ser Ile Cys
                85                  90                  95

Thr Gly Thr Ser Ser Gly Asn Gln Val Asn Leu Thr Ile Gln Leu Arg
            100                 105                 110

Ala Met Asp Thr Gly Leu Tyr Ile Cys Lys Val Glu Leu Met Tyr Pro
```

```
                    115                         120                         125
    Pro  Pro  Tyr  Tyr  Leu  Gly  Ile  Gly  Asn  Gly  Thr  Gln  Ile  Tyr  Val  Ile
         130                      135                     140

Asp  Pro  Glu  Pro  Cys  Pro  Asp  Ser  Arg  Asp  Pro  Gly  Met  Glu  Val  Arg
    145                      150                     155                          160

Trp  Cys  Ala  Thr  Ser  Asp  Pro  Glu  Gln  His  Lys  Cys  Gly  Asn  Met  Ser
                        165                     170                     175

Glu  Ala  Phe  Arg  Glu  Ala  Gly  Ile  Gln  Pro  Ser  Leu  Leu  Cys  Val  Arg
                   180                     185                          190

Gly  Thr  Ser  Ala  Asp  His  Cys  Val  Gln  Leu  Ile  Ala  Ala  Gln  Glu  Ala
              195                     200                     205

Asp  Ala  Ile  Thr  Leu  Asp  Gly  Ala  Ile  Tyr  Glu  Ala  Gly  Lys  Glu
         210                     215                     220

His  Gly  Leu  Lys  Pro  Val  Val  Gly  Glu  Val  Tyr  Asp  Gln  Glu  Val  Gly
    225                      230                     235                          240

Thr  Ser  Tyr  Tyr  Ala  Val  Ala  Val  Val  Arg  Arg  Ser  Ser  His  Val  Thr
                        245                     250                     255

Ile  Asp  Thr  Leu  Lys  Gly  Val  Lys  Ser  Cys  His  Thr  Gly  Ile  Asn  Arg
                   260                     265                     270

Thr  Val  Gly  Trp  Asn  Val  Pro  Val  Gly  Tyr  Leu  Val  Glu  Ser  Gly  Arg
              275                     280                     285

Leu  Ser  Val  Met  Gly  Cys  Asp  Val  Leu  Lys  Ala  Val  Ser  Asp  Tyr  Phe
         290                     295                     300

Gly  Gly  Ser  Cys  Val  Pro  Gly  Ala  Gly  Glu  Thr  Ser  Tyr  Ser  Glu  Ser
    305                      310                     315                          320

Leu  Cys  Arg  Leu  Cys  Arg  Gly  Asp  Ser  Ser  Gly  Glu  Gly  Val  Cys  Asp
                        325                     330                          335

Lys  Ser  Pro  Leu  Glu  Arg  Tyr  Tyr  Asp  Tyr  Ser  Gly  Ala  Phe  Arg  Cys
                   340                     345                     350

Leu  Ala  Glu  Gly  Ala  Gly  Asp  Val  Ala  Phe  Val  Lys  His  Ser  Thr  Val
              355                     360                     365

Leu  Glu  Asn  Thr  Asp  Gly  Lys  Thr  Leu  Pro  Ser  Trp  Gly  Gln  Ala  Leu
         370                     375                     380

Leu  Ser  Gln  Asp  Phe  Glu  Leu  Leu  Cys  Arg  Asp  Gly  Ser  Arg  Ala  Asp
    385                      390                     395                          400

Val  Thr  Glu  Trp  Arg  Gln  Cys  His  Leu  Ala  Arg  Val  Pro  Ala  His  Ala
                        405                     410                     415

Val  Val  Val  Arg  Ala  Asp  Thr  Asp  Gly  Gly  Leu  Ile  Phe  Arg  Leu  Leu
                   420                     425                     430

Asn  Glu  Gly  Gln  Arg  Leu  Phe  Ser  His  Glu  Gly  Ser  Ser  Phe  Gln  Met
              435                     440                     445

Phe  Ser  Ser  Glu  Ala  Tyr  Gly  Gln  Lys  Asp  Leu  Leu  Phe  Lys  Asp  Ser
    450                      455                     460

Thr  Ser  Glu  Leu  Val  Pro  Ile  Ala  Thr  Gln  Thr  Tyr  Glu  Ala  Trp  Leu
    465                      470                     475                          480

Gly  His  Glu  Tyr  Leu  His  Ala  Met  Lys  Gly  Leu  Leu  Cys  Asp  Pro  Asn
                        485                     490                          495

Arg  Leu  Pro  Pro  Tyr  Leu
                   500
```

( 2 ) INFORMATION FOR SEQ ID NO:20:

( i ) SEQUENCE CHARACTERISTICS:
        ( A ) LENGTH: 253 amino acids
        ( B ) TYPE: amino acid ( C ) STRANDEDNESS:
( D ) TOPOLOGY: linear ( i i ) MOLECULE TYPE: protein ( x i ) SEQUENCE DESCRIPTION: SEQ ID NO:20:

```
Gln  Ala  Ser  Pro  Met  Gly  Val  Leu  Leu  Thr  Gln  Arg  Thr  Leu  Leu  Ser
1                   5                        10                       15
Leu  Val  Leu  Ala  Leu  Leu  Phe  Pro  Ser  Met  Ala  Ser  Met  Ala  Met  His
               20                       25                       30
Val  Ala  Gln  Pro  Ala  Val  Val  Leu  Ala  Ser  Ser  Arg  Gly  Ile  Ala  Ser
          35                       40                       45
Phe  Val  Cys  Glu  Tyr  Ala  Ser  Pro  Gly  Lys  Ala  Thr  Glu  Val  Arg  Val
     50                       55                       60
Thr  Val  Leu  Arg  Gln  Ala  Asp  Ser  Gln  Val  Thr  Glu  Val  Cys  Ala  Ala
65                       70                       75                       80
Thr  Tyr  Met  Met  Gly  Asn  Glu  Leu  Thr  Phe  Leu  Asp  Asp  Ser  Ile  Cys
                    85                       90                       95
Thr  Gly  Thr  Ser  Ser  Gly  Asn  Gln  Val  Asn  Leu  Thr  Ile  Gln  Leu  Arg
               100                      105                      110
Ala  Met  Asp  Thr  Gly  Leu  Tyr  Ile  Cys  Lys  Val  Glu  Leu  Met  Tyr  Pro
          115                      120                      125
Pro  Pro  Tyr  Tyr  Leu  Gly  Ile  Gly  Asn  Gly  Thr  Gln  Ile  Tyr  Val  Ile
     130                      135                      140
Asp  Pro  Glu  Pro  Cys  Pro  Asp  Ser  Arg  Asp  Pro  Met  His  Gly  Asp  Thr
145                      150                      155                      160
Pro  Thr  Leu  His  Glu  Tyr  Met  Leu  Asp  Leu  Gln  Pro  Glu  Thr  Thr  Asp
                    165                      170                      175
Leu  Tyr  Cys  Tyr  Glu  Gln  Leu  Asn  Asp  Ser  Ser  Glu  Glu  Glu  Asp  Glu
               180                      185                      190
Ile  Asp  Gly  Pro  Ala  Gly  Gln  Ala  Glu  Pro  Asp  Arg  Ala  His  Tyr  Asn
          195                      200                      205
Ile  Val  Thr  Phe  Cys  Cys  Lys  Cys  Asp  Ser  Thr  Leu  Arg  Leu  Cys  Val
     210                      215                      220
Gln  Ser  Thr  His  Val  Asp  Ile  Arg  Thr  Leu  Glu  Asp  Leu  Leu  Met  Gly
225                      230                      235                      240
Thr  Leu  Gly  Ile  Val  Cys  Pro  Ile  Cys  Ser  Gln  Lys  Pro
                    245                      250
```

( 2 ) INFORMATION FOR SEQ ID NO:21:

( i ) SEQUENCE CHARACTERISTICS:
( A ) LENGTH: 234 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:21:

```
Met  Ala  Cys  Leu  Gly  Phe  Gln  Arg  His  Lys  Ala  Gln  Leu  Asn  Leu  Ala
1                   5                        10                       15
Ala  Arg  Thr  Trp  Pro  Cys  Thr  Leu  Leu  Phe  Phe  Leu  Leu  Phe  Ile  Pro
               20                       25                       30
Val  Phe  Cys  Lys  Ala  Met  His  Val  Ala  Gln  Pro  Ala  Val  Val  Leu  Ala
          35                       40                       45
Ser  Ser  Arg  Gly  Ile  Ala  Ser  Phe  Val  Cys  Glu  Tyr  Ala  Ser  Pro  Gly
     50                       55                       60
```

| | | | | | | | | | | | | | | |
|---|---|---|---|---|---|---|---|---|---|---|---|---|---|---|
| Lys<br>65 | Ala | Thr | Glu | Val | Arg<br>70 | Val | Thr | Val | Leu | Arg<br>75 | Gln | Ala | Asp | Ser | Gln<br>80 |
| Val | Thr | Glu | Val | Cys<br>85 | Ala | Ala | Thr | Tyr | Met<br>90 | Thr | Gly | Asn | Glu | Leu<br>95 | Thr |
| Phe | Leu | Asp | Asp<br>100 | Ser | Xaa | Xaa | Ile | Cys<br>105 | Thr | Gly | Thr | Ser | Ser<br>110 | Gly | Asn |
| Gln | Val | Asn<br>115 | Leu | Thr | Ile | Gln | Gly<br>120 | Leu | Arg | Ala | Met | Asp<br>125 | Thr | Gly | Leu |
| Tyr | Ile<br>130 | Cys | Lys | Val | Glu | Leu<br>135 | Met | Tyr | Pro | Pro | Pro<br>140 | Tyr | Tyr | Leu | Xaa |
| Gly<br>145 | Ile | Gly | Asn | Gly | Thr<br>150 | Gln | Ile | Tyr | Val | Ile<br>155 | Asp | Pro | Glu | Pro | Cys<br>160 |
| Xaa | Xaa | Xaa | Xaa | Xaa<br>165 | Pro | Asp | Ser | Asp | Phe<br>170 | Leu | Leu | Trp | Ile | Leu<br>175 | Ala |
| Ala | Val | Ser | Ser<br>180 | Gly | Leu | Phe | Phe | Tyr<br>185 | Ser | Phe | Leu | Leu | Thr<br>190 | Xaa | Ala |
| Val | Ser | Leu | Ser<br>195 | Lys | Met | Leu | Lys<br>200 | Lys | Arg | Ser | Pro | Leu<br>205 | Thr | Thr | Gly |
| Val | Tyr<br>210 | Val | Lys | Met | Pro | Pro<br>215 | Thr | Glu | Pro | Glu | Cys<br>220 | Glu | Xaa | Xaa | Lys |
| Gln<br>225 | Phe | Gln | Pro | Tyr | Phe<br>230 | Ile | Pro | Ile | Asn | | | | | | |

(2) INFORMATION FOR SEQ ID NO:22:

(i) SEQUENCE CHARACTERISTICS:
        (A) LENGTH: 234 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

| | | | | | | | | | | | | | | |
|---|---|---|---|---|---|---|---|---|---|---|---|---|---|---|
| Met<br>1 | Ala | Cys | Leu | Gly<br>5 | Leu | Arg | Arg | Tyr | Lys<br>10 | Ala | Gln | Leu | Gln | Leu<br>15 | Pro |
| Ser | Arg | Thr | Trp<br>20 | Pro | Phe | Val | Ala | Leu<br>25 | Leu | Thr | Leu | Leu | Phe<br>30 | Ile | Pro |
| Val | Phe | Ser<br>35 | Glu | Ala | Ile | Gln | Val<br>40 | Thr | Gln | Pro | Ser | Val<br>45 | Tyr | Leu | Ala |
| Ser | Ser<br>50 | His | Gly | Tyr | Ala | Ser<br>55 | Phe | Pro | Cys | Glu | Tyr<br>60 | Ser | Pro | Ser | His |
| Asn<br>65 | Thr | Asp | Glu | Tyr | Arg<br>70 | Val | Thr | Val | Leu | Arg<br>75 | Gln | Thr | Asn | Asp | Gln<br>80 |
| Met | Thr | Glu | Val | Cys<br>85 | Ala | Thr | Thr | Phe | Thr<br>90 | Glu | Lys | Asn | Thr | Val<br>95 | Gly |
| Phe | Leu | Asp | Tyr<br>100 | Pro | Xaa | Xaa | Phe | Cys<br>105 | Ser | Gly | Thr | Phe | Asn<br>110 | Glu | Ser |
| Arg | Val | Asn<br>115 | Leu | Thr | Ile | Gln | Gly<br>120 | Leu | Arg | Ala | Val | Asp<br>125 | Thr | Gly | Leu |
| Tyr | Leu<br>130 | Cys | Lys | Val | Glu | Leu<br>135 | Met | Tyr | Pro | Pro | Pro<br>140 | Tyr | Phe | Val | Xaa |
| Gly<br>145 | Met | Gly | Asn | Gly | Thr<br>150 | Gln | Ile | Tyr | Tyr | Ile<br>155 | Asp | Pro | Glu | Pro | Cys<br>160 |
| Xaa | Xaa | Xaa | Xaa | Xaa<br>165 | Pro | Asp | Ser | Asp | Phe<br>170 | Leu | Leu | Trp | Ile | Leu<br>175 | Tyr |
| Ala | Val | Ser | Leu | Gly<br>180 | Leu | Phe | Phe | Tyr | Ser<br>185 | Phe | Leu | Val | Ser | Xaa<br>190 | Ala |

|   |   |   | 180 |   |   |   |   | 185 |   |   |   |   | 190 |   |
|---|---|---|---|---|---|---|---|---|---|---|---|---|---|---|
| Val | Ser | Leu | Ser | Lys | Met | Leu | Lys | Lys | Arg | Ser | Pro | Leu | Thr | Thr | Gly |
|   |   |   | 195 |   |   |   |   | 200 |   |   |   |   | 205 |   |   |
| Val | Tyr | Val | Lys | Met | Pro | Pro | Thr | Glu | Pro | Glu | Cys | Glu | Xaa | Xaa | Lys |
|   |   |   | 210 |   |   |   |   | 215 |   |   |   |   | 220 |   |   |
| Gln | Phe | Gln | Pro | Tyr | Phe | Ile | Pro | Ile | Asn |   |   |   |   |   |   |
| 225 |   |   |   |   | 230 |   |   |   |   |   |   |   |   |   |   |

(2) INFORMATION FOR SEQ ID NO:23:

(i) SEQUENCE CHARACTERISTICS:
       (A) LENGTH: 225 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:23:

| Met | Thr | Leu | Arg | Leu | Leu | Phe | Leu | Ala | Leu | Asn | Phe | Phe | Xaa | Ser | Val |
|---|---|---|---|---|---|---|---|---|---|---|---|---|---|---|---|
| 1 |   |   |   | 5 |   |   |   |   | 10 |   |   |   |   | 15 |   |
| Gln | Val | Thr | Glu | Asn | Lys | Ile | Leu | Val | Lys | Gln | Ser | Pro | Leu | Leu | Tyr |
|   |   |   | 20 |   |   |   |   | 25 |   |   |   |   | 30 |   |   |
| Val | Asp | Ser | Asn | Glu | Val | Xaa | Ser | Leu | Ser | Cys | Arg | Tyr | Ser | Tyr | Asn |
|   |   |   | 35 |   |   |   |   | 40 |   |   |   |   | 45 |   |   |
| Leu | Leu | Ala | Lys | Glu | Phe | Arg | Ala | Ser | Leu | Tyr | Lys | Gly | Val | Asn | Ser |
|   |   |   | 50 |   |   |   |   | 55 |   |   |   |   | 60 |   |   |
| Asp | Val | Xaa | Glu | Val | Cys | Val | Gly | Asn | Gly | Asn | Phe | Thr | Tyr | Gln | Pro |
| 65 |   |   |   |   | 70 |   |   |   |   | 75 |   |   |   |   | 80 |
| Gln | Phe | Arg | Ser | Asn | Ala | Glu | Phe | Asn | Cys | Asp | Gly | Asp | Phe | Asp | Asn |
|   |   |   | 85 |   |   |   |   | 90 |   |   |   |   | 95 |   |   |
| Glu | Thr | Val | Thr | Phe | Arg | Leu | Trp | Asn | Leu | His | Val | Asn | His | Thr | Asp |
|   |   |   | 100 |   |   |   |   | 105 |   |   |   |   | 110 |   |   |
| Ile | Tyr | Phe | Cys | Lys | Ile | Glu | Phe | Met | Tyr | Pro | Pro | Pro | Tyr | Leu | Asp |
|   |   |   | 115 |   |   |   |   | 120 |   |   |   |   | 125 |   |   |
| Asn | Glu | Arg | Ser | Asn | Gly | Thr | Ile | Ile | His | Ile | Lys | Glu | Lys | His | Leu |
|   |   |   | 130 |   |   |   |   | 135 |   |   |   |   | 140 |   |   |
| Cys | His | Thr | Xaa | Xaa | Xaa | Gln | Ser | Ser | Pro | Lys | Leu | Phe | Trp | Ala | Leu |
| 145 |   |   |   |   | 150 |   |   |   |   | 155 |   |   |   |   | 160 |
| Tyr | Val | Val | Ala | Gly | Val | Leu | Phe | Cys | Tyr | Gly | Leu | Leu | Val | Thr | Val |
|   |   |   | 165 |   |   |   |   | 170 |   |   |   |   | 175 |   |   |
| Ala | Leu | Cys | Val | Ile | Trp | Thr | Asn | Ser | Arg | Arg | Asn | Arg | Leu | Leu | Gln |
|   |   |   | 180 |   |   |   |   | 185 |   |   |   |   | 190 |   |   |
| Val | Thr | Tyr | Met | Asn | Met | Thr | Pro | Arg | Arg | Pro | Gly | Leu | Thr | Arg | Xaa |
|   |   |   | 195 |   |   |   |   | 200 |   |   |   |   | 205 |   |   |
| Lys | Pro | Tyr | Gln | Pro | Tyr | Ala | Pro | Ala | Arg | Asp | Phe | Ala | Ala | Tyr | Arg |
|   |   |   | 210 |   |   |   |   | 215 |   |   |   |   | 220 |   |   |
| Pro |   |   |   |   |   |   |   |   |   |   |   |   |   |   |   |
| 225 |   |   |   |   |   |   |   |   |   |   |   |   |   |   |   |

(2) INFORMATION FOR SEQ ID NO:24:

(i) SEQUENCE CHARACTERISTICS:
       (A) LENGTH: 225 amino acids
       (B) TYPE: amino acid
       (C) STRANDEDNESS:
       (D) TOPOLOGY: linear (ii) MOLECULE TYPE: protein (xi) SEQUENCE DESCRIPTION: SEQ ID NO:24:

| Met | Thr | Leu | Arg | Leu | Leu | Phe | Leu | Ala | Leu | Ser | Phe | Phe | Xaa | Ser | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Val | Thr | Glu | Asn | Lys | Ile | Leu | Val | Lys | Gln | Ser | Pro | Leu | Leu | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Tyr | Asp | Asn | Asn | Glu | Val | Xaa | Ser | Leu | Ser | Cys | Arg | Tyr | Ser | Tyr | Asn |
|-----|-----|-----|-----|-----|-----|-----|-----|-----|-----|-----|-----|-----|-----|-----|-----|
|     |     | 35  |     |     |     | 40  |     |     |     |     |     | 45  |     |     |     |

| Leu | Leu | Ala | Lys | Glu | Phe | Arg | Ala | Ser | Leu | Tyr | Lys | Gly | Val | Asn | Ser |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asp | Val | Xaa | Glu | Val | Cys | Val | Gly | Asn | Gly | Asn | Phe | Thr | Tyr | Gln | Pro |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Phe | Arg | Pro | Asn | Val | Gly | Phe | Asn | Cys | Asp | Gly | Asn | Phe | Asp | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Thr | Val | Thr | Phe | Arg | Leu | Trp | Asn | Leu | Asp | Val | Asn | His | Thr | Asp |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ile | Tyr | Phe | Cys | Lys | Ile | Glu | Val | Met | Tyr | Pro | Pro | Pro | Tyr | Leu | Asp |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Asn | Glu | Lys | Ser | Asn | Gly | Thr | Ile | Ile | His | Ile | Lys | Glu | Lys | His | Leu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Cys | His | Ala | Xaa | Xaa | Xaa | Gln | Thr | Ser | Pro | Lys | Leu | Phe | Trp | Pro | Leu |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Val | Val | Val | Ala | Gly | Val | Leu | Leu | Cys | Tyr | Gly | Leu | Leu | Tyr | Thr | Val |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Thr | Leu | Cys | Ile | Ile | Trp | Thr | Asn | Ser | Arg | Arg | Asn | Arg | Leu | Leu | Gln |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ser | Asp | Tyr | Met | Asn | Met | Thr | Pro | Arg | Arg | Leu | Gly | Pro | Thr | Arg | Xaa |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Lys | His | Tyr | Gln | Pro | Tyr | Ala | Pro | Ala | Arg | Asp | Phe | Ala | Ala | Tyr | Arg |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Pro |
|-----|
| 225 |

(2) INFORMATION FOR SEQ ID NO:25:

(i) SEQUENCE CHARACTERISTICS:
(A) LENGTH: 223 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:25:

| Met | Leu | Arg | Leu | Leu | Leu | Ala | Leu | Asn | Leu | Phe | Pro | Ser | Ile | Gln | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Gly | Asn | Lys | Ile | Leu | Val | Lys | Gln | Ser | Pro | Met | Leu | Val | Ala | Tyr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Asn | Ala | Tyr | Xaa | Asn | Leu | Ser | Cys | Lys | Tyr | Ser | Tyr | Asn | Leu | Phe |
|-----|-----|-----|-----|-----|-----|-----|-----|-----|-----|-----|-----|-----|-----|-----|-----|
|     |     | 35  |     |     |     | 40  |     |     |     |     |     | 45  |     |     |     |

| Ser | Arg | Glu | Phe | Arg | Ala | Ser | Leu | His | Lys | Gly | Leu | Asp | Ser | Ala | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Xaa | Glu | Val | Cys | Val | Val | Tyr | Gly | Asn | Tyr | Ser | Gln | Gln | Leu | Gln | Val |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Tyr | Ser | Lys | Thr | Gly | Phe | Asn | Cys | Asp | Gly | Lys | Leu | Gly | Asn | Glu | Ser |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Val | Thr | Phe | Tyr | Leu | Gln | Asn | Leu | Tyr | Val | Asn | Gln | Thr | Asp | Ile | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

5,885,796

67

68

-continued

| Phe | Cys | Lys | Ile | Glu | Val | Met | Tyr | Pro | Pro | Pro | Tyr | Leu | Asp | Asn | Glu |
|     | 115 |     |     |     |     | 120 |     |     |     |     | 125 |     |     |     |     |

| Lys | Ser | Asn | Gly | Thr | Ile | Ile | His | Val | Lys | Gly | Lys | His | Leu | Cys | Pro |
|     | 130 |     |     |     |     | 135 |     |     |     |     | 140 |     |     |     |     |

| Ser | Pro | Leu | Phe | Pro | Gly | Pro | Ser | Lys | Pro | Phe | Trp | Val | Leu | Val | Val |
| 145 |     |     |     |     | 150 |     |     |     |     | 155 |     |     |     |     | 160 |

| Val | Gly | Gly | Val | Leu | Ala | Cys | Tyr | Ser | Leu | Leu | Tyr | Thr | Val | Ala | Phe |
|     |     |     |     | 165 |     |     |     |     | 170 |     |     |     |     | 175 |     |

| Ile | Ile | Phe | Trp | Val | Arg | Ser | Lys | Arg | Ser | Arg | Leu | Leu | His | Ser | Asp |
|     |     |     | 180 |     |     |     |     | 185 |     |     |     |     | 190 |     |     |

| Tyr | Met | Asn | Met | Thr | Pro | Arg | Arg | Pro | Gly | Pro | Thr | Arg | Xaa | Lys | His |
|     |     | 195 |     |     |     |     | 200 |     |     |     |     | 205 |     |     |     |

| Tyr | Gln | Pro | Tyr | Ala | Pro | Pro | Arg | Asp | Phe | Ala | Ala | Tyr | Arg | Ser |
|     | 210 |     |     |     |     | 215 |     |     |     |     | 220 |     |     |     |

( 2 ) INFORMATION FOR SEQ ID NO:26:

( i ) SEQUENCE CHARACTERISTICS:
        ( A ) LENGTH: 226 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:26:

| Met | Leu | Gly | Ile | Leu | Val | Val | Leu | Cys | Leu | Ile | Pro | Ala | Ala | Asp | Val |
| 1   |     |     |     | 5   |     |     |     |     | 10  |     |     |     |     | 15  |     |

| Thr | Glu | Asn | Lys | Ile | Leu | Val | Ala | Gln | Arg | Pro | Leu | Leu | Ile | Val | Ala |
|     |     |     | 20  |     |     |     |     | 25  |     |     |     |     | 30  |     |     |

| Asn | Arg | Thr | Ala | Xaa | Thr | Leu | Val | Cys | Asn | Tyr | Thr | Tyr | Asn | Gly | Thr |
|     |     | 35  |     |     |     |     | 40  |     |     |     |     | 45  |     |     |     |

| Gly | Lys | Glu | Phe | Arg | Ala | Ser | Leu | His | Lys | Gly | Thr | Asp | Ser | Ala | Val |
|     | 50  |     |     |     |     | 55  |     |     |     |     | 60  |     |     |     |     |

| Xaa | Glu | Val | Cys | Phe | Ile | Ser | Trp | Asn | Met | Thr | Xaa | Lys | Ile | Asn | Ser |
| 65  |     |     |     |     | 70  |     |     |     |     | 75  |     |     |     |     | 80  |

| Asn | Ser | Asn | Lys | Glu | Phe | Asn | Cys | Arg | Gly | Ile | His | Asp | Lys | Asp | Lys |
|     |     |     |     | 85  |     |     |     |     | 90  |     |     |     |     | 95  |     |

| Val | Ile | Phe | Asn | Leu | Trp | Asn | Met | Ser | Ala | Ser | Gln | Thr | Asp | Ile | Tyr |
|     |     |     | 100 |     |     |     |     | 105 |     |     |     |     | 110 |     |     |

| Phe | Cys | Lys | Ile | Glu | Ala | Met | Tyr | Pro | Pro | Pro | Tyr | Val | Tyr | Asn | Glu |
|     |     | 115 |     |     |     |     | 120 |     |     |     |     | 125 |     |     |     |

| Lys | Ser | Asn | Gly | Thr | Val | Ile | His | Tyr | Arg | Glu | Thr | Pro | Ile | Xaa | Xaa |
|     | 130 |     |     |     |     | 135 |     |     |     |     | 140 |     |     |     |     |

| Gln | Thr | Gln | Glu | Pro | Glu | Ser | Ala | Thr | Ser | Tyr | Trp | Val | Met | Tyr | Ala |
| 145 |     |     |     |     | 150 |     |     |     |     | 155 |     |     |     |     | 160 |

| Val | Thr | Gly | Leu | Leu | Gly | Phe | Tyr | Ser | Met | Leu | Ile | Thr | Ala | Val | Phe |
|     |     |     |     | 165 |     |     |     |     | 170 |     |     |     |     | 175 |     |

| Ile | Ile | Tyr | Arg | Gln | Lys | Ser | Lys | Arg | Asn | Arg | Tyr | Arg | Gln | Ser | Asp |
|     |     |     | 180 |     |     |     |     | 185 |     |     |     |     | 190 |     |     |

| Tyr | Met | Asn | Met | Thr | Pro | Arg | His | Pro | Pro | His | Gln | Lys | Asn | Lys | Gly |
|     |     | 195 |     |     |     |     | 200 |     |     |     |     | 205 |     |     |     |

| Tyr | Pro | Ser | Tyr | Ala | Pro | Thr | Arg | Asp | Tyr | Thr | Ala | Tyr | Arg | Ser | Trp |
|     | 210 |     |     |     |     | 215 |     |     |     |     | 220 |     |     |     |     |

| Gln | Pro |
| 225 |     |

What is claimed is:

1. An isolated CTLA4 receptor protein having the amino acid sequence depicted in FIG. 3 (SEQ ID NO: 14).

2. A DNA sequence encoding the amino acid sequence corresponding to CTLA4Ig fusion protein reactive with B7 antigen and having ATCC No. 68629.

3. A purified soluble CTLA4 protein comprising the 125 amino acids shown in SEQ ID NO: 14 beginning with alanine at position 1 and ending with asparagine at position 125 of the amino acid sequence of the extracellular domain of the CTLA4 protein.

4. A purified, soluble CTLA4 protein which binds a B7 antigen expressed on activated B cells, comprising the 187 amino acids shown in SEQ ID NO: 14 beginning with alanine at position 1 and ending with asparagine at position 187.

5. An isolated nucleic acid molecule encoding the protein of claim 4 or 3.

6. The nucleic acid molecule of claim 5 which is a cDNA having the sequence of SEQ ID NO: 13.

7. The cDNA of claim 6 shown in SEQ ID NO: 13 beginning with guanine at position 1 and ending with adenosine at position 374.

8. A plasmid which comprises the nucleic acid molecule of claim 5.

9. A host vector system comprising a plasmid of claim 8 in a suitable host cell.

10. The host vector system of claim 9, wherein the suitable host cell is a bacterial cell.

11. The host vector system of claim 9, wherein the suitable host cell is a eucaryotic cell.

12. A method for producing a soluble CTLA4 protein comprising growing the host vector system of claim 9 so as to produce the soluble CTLA4 protein in the host and recovering the soluble CTLA4 protein so produced.

* * * * *

UNITED STATES PATENT AND TRADEMARK OFFICE
CERTIFICATE OF CORRECTION

PATENT NO. : 5,885,796 Page 1 of 1
APPLICATION NO. : 08/465078
DATED : March 23, 1999
INVENTOR(S) : Linsley et al.

It is certified that error appears in the above-identified patent and that said Letters Patent is hereby corrected as shown below:

Col. 8, line 57, replace "7%" with -- 70% --

Signed and Sealed this

Eleventh Day of March, 2008

JON W. DUDAS
*Director of the United States Patent and Trademark Office*